United States Patent
Bergmann et al.

(10) Patent No.: US 11,773,130 B2
(45) Date of Patent: *Oct. 3, 2023

(54) 3' PROTECTED NUCLEOTIDES

(71) Applicant: Roche Sequencing Solutions, Inc., Pleasanton, CA (US)

(72) Inventors: Frank Bergmann, Iffeldorf (DE); Peter Crisalli, Mountain View, CA (US); Dieter Heindl, Munich (DE); Omid Khakshoor, Lathrop, CA (US); Meng Taing, Hayward, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,099

(22) Filed: Jul. 6, 2022

(65) Prior Publication Data

US 2022/0348604 A1 Nov. 3, 2022

Related U.S. Application Data

(63) Continuation of application No. 17/416,186, filed as application No. PCT/US2019/066670 on Dec. 16, 2019, now Pat. No. 11,440,933.

(60) Provisional application No. 62/781,638, filed on Dec. 19, 2018.

(51) Int. Cl.
*C07H 19/06* (2006.01)
*C07H 19/048* (2006.01)

(52) U.S. Cl.
CPC .......... *C07H 19/06* (2013.01); *C07H 19/048* (2013.01)

(58) Field of Classification Search
None
See application file for complete search history.

(56) References Cited

FOREIGN PATENT DOCUMENTS

| WO | 2012162429 A2 | 11/2012 |
| WO | 2013154999 A2 | 10/2013 |
| WO | 2013191793 A1 | 12/2013 |
| WO | 2015148402 A1 | 10/2015 |
| WO | 2017058953 A1 | 4/2017 |

OTHER PUBLICATIONS

Angelika C. Keller et al, "Synthesis of 3'-O-(2-cyanoethyl)-2'-deoxythymidine-5'-phosphate as a model compound for evaluation of cyanoethyl cleavage", Collection Symposium Series (XIIITH Symposium on Chemistry of Nucleic Acid Components Spindleruv MLYN, Czech Republic; Sep. 3-9, 2005), vol. 74, No. 4, Jan. 1, 2009 (Jan. 1, 2009), p. 515-534.

Diana C. Knapp et al, "Fluoride-Cleavable, Fluorescently Labelled Reversible Terminators: Synthesis and Use in Primer Extension", Chemistry—A European Journal, vol. 17, No. 10, Feb. 3, 2011 (Feb. 3, 2011), p. 2903-2915.

Jia Guo et al, "An Integrated System for DNA Sequencing by Synthesis Using Novel Nucleotide Analogues", Accounts of Chemical Research, vol. 43, No. 4, Apr. 20, 2010 (Apr. 20, 2010), p. 551-563.

International Search Report and Written Opinion Issued for PCT/US2019/066670, dated Jun. 25, 2000.

International Preliminary Report on Patentability for PCT/US2019/066670, dated Nov. 18, 2020.

*Primary Examiner* — Layla D Berry
(74) *Attorney, Agent, or Firm* — CHARNEY IP LAW LLC; Thomas M. Finetti

(57) ABSTRACT

The present disclosure provides 3' protected nucleotides, including those 3' protected nucleotides having a detectable tag. Systems and methods of sequencing nucleic acids using the 3' protected nucleotides are also disclosed, such as the sequencing of a nucleic acid using a nanopore or the sequencing of a nucleic acid via sequencing-by-synthesis.

23 Claims, 8 Drawing Sheets

3' PROTECTED NUCLEOTIDES

CROSS REFERENCE TO RELATED APPLICATIONS

The present application is a continuation of U.S. patent application Ser. No. 17/416,186, filed on Jun. 18, 2021, which application is a national stage application, filed under 35 U.S.C. Section 371, of International Patent Application No. PCT/US2019/066670, filed on Dec. 16, 2019, which application claims the benefit of the filing date of U.S. Provisional Application No. 62/781,638 filed on Dec. 19, 2018, the disclosures of which are hereby incorporated by reference herein in their entireties.

FIELD OF THE DISCLOSURE

The present disclosure generally relates to 3' protected nucleotides suitable for use in sequencing.

BACKGROUND OF THE DISCLOSURE

The importance of DNA sequencing has increased dramatically from its inception four decades ago. It is recognized as a crucial technology for most areas of biology and medicine and as the underpinning for the new paradigm of personalized and precision medicine. Information on individuals' genomes and epigenomes can help reveal their propensity for disease, clinical prognosis, and response to therapeutics, but routine application of genome sequencing in medicine will require comprehensive data delivered in a timely and cost-effective manner.

Nanopore-based nucleic acid sequencing is an approach that has been widely studied. In the last two decades, there has been great interest in taking advantage of nanopores for polymer characterization and for distinguishing nucleotides in a low-cost, rapid, single-molecule manner. For example, Kasianowicz et. al. characterized single-stranded polynucleotides as they were electrically translocated through an alpha hemolysin nanopore embedded in a lipid bilayer (see, e.g., Kasianowicz, J. (1996), Characterization of Individual Polynucleotide Molecules using a Membrane Channel. Proc. Natl. Acad. Sci., 93, 13770-3). It was demonstrated that during polynucleotide translocation partial blockage of the nanopore aperture could be measured as a decrease in ionic current. Similarly, Gundlach et. al. demonstrated a method of sequencing DNA that used a low noise nanopore derived from *Mycobacterium smegmatis* ("MspA") in conjunction with a process called duplex interrupted sequencing (see, e.g., Derrington, I. et al. (2010), Nanopore DNA Sequencing with MspA. Proc. Natl. Acad. Sci., 107(37), 16060-16065). Here, a double strand duplex was used to temporarily hold the single-stranded portion of the nucleic acid in the MspA constriction. Akeson et. al. (see, e.g., PCT Publication No. WO/20150344945) disclose methods for characterizing polynucleotides in a nanopore that utilize an adjacently positioned molecular motor to control the translocation rate of the polynucleotide through or adjacent to the nanopore aperture.

In general, three nanopore sequencing approaches have been pursued: strand sequencing in which the bases of DNA are identified as they pass sequentially through a nanopore, exonuclease-based nanopore sequencing in which nucleotides are enzymatically cleaved one-by-one from a DNA molecule and monitored as they are captured by and pass through the nanopore, and a nanopore sequencing by synthesis (SBS) approach in which identifiable polymer tags are attached to nucleotides and registered in nanopores during enzyme-catalyzed DNA synthesis. Common to all these methods is the need for precise control of the reaction rates so that each base is determined in order. Strand sequencing requires a method for slowing down the passage of the DNA through the nanopore and decoding a plurality of bases within the channel; ratcheting approaches, taking advantage of molecular motors, have been developed for this purpose. Exonuclease-based sequencing requires the release of each nucleotide close enough to the pore to guarantee its capture and its transit through the pore at a rate slow enough to obtain a valid ionic current signal. In addition, both of these methods rely on distinctions among the four natural bases, two relatively similar purines and two similar pyrimidines. The nanopore SBS approach utilizes synthetic polymer tags attached to the nucleotides that are designed specifically to produce unique and readily distinguishable ionic current blockade signatures for sequence determination.

BRIEF SUMMARY OF THE DISCLOSURE

In one aspect of the present disclosure are nucleotides or salts thereof having Formula (IIIA):

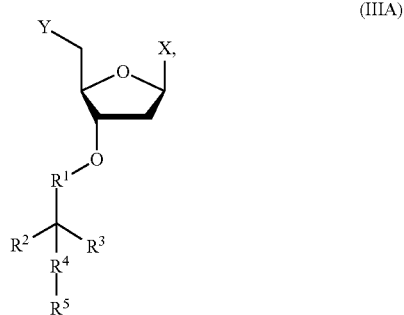

(IIIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$—(R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$R^5$ is —(C(R$^a$)(R$^b$))$_n$—N$_3$, —(C(R$^a$)(R$^b$))$_n$—N$^+$C$^-$, —(C(R$^a$)(R$^b$))$_n$—CN, a 5- to 8-membered cycloalkyl group comprising two sulfur atoms positioned 1, 3 relative to each other, or a group having the structure:

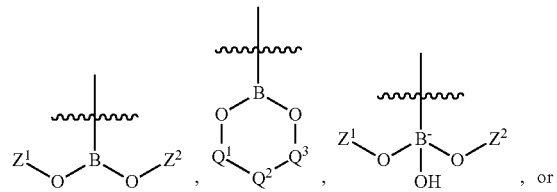

, or

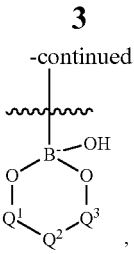

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide (e.g. $R^5$ is not $N^3$).

In some embodiments, $R^5$ is:

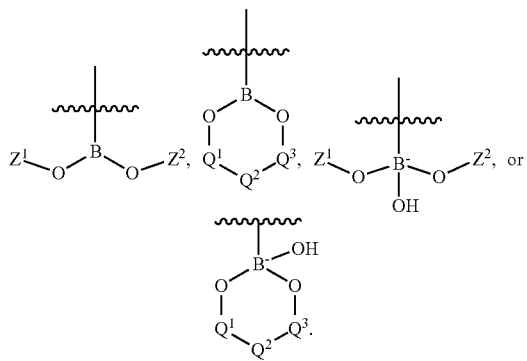

In some embodiments, at least one of $Z^1$ or $Z^2$ is H. In some embodiments, $R^1$ is a bond and at least one of $Z^1$ or $Z^2$ is H. In some embodiments, $R^1$ is —CH$_2$— and at least one of $Z^1$ or $Z^2$ is H. In some embodiments, $Z^1$ and $Z^2$ are H. In some embodiments, $R^5$ is —B(OH)$_2$.

In some embodiments, $R^1$ is a bond. In some embodiments, $R^1$ is a bond and $R^4$ is a bond. In some embodiments, $R^1$ is a bond and $R^4$ is a bond, and at least one of $R^2$ or $R^3$ is H. In some embodiments, $R^1$ is a bond, and $R^4$ is a 6-membered aryl group. In some embodiments, $R^1$ is a bond, and $R^4$ is a 6-membered aryl group, and at least one of $R^2$ or $R^3$ is H. In some embodiments, $R^1$ is —C(O)—O—. In some embodiments, $R^1$ is —C(O)—O—, and $R^4$ is a 6-membered aryl group. In some embodiments, the 6-membered aryl group includes at least one substituent, wherein the at least one substituent is selected from the group consisting of methyl and ethyl. In some embodiments, $R^1$ is —C(O)—O—, and $R^4$ is a 6-membered aryl group at least one of $R^2$ or $R^3$ is H. In some embodiments, $R^1$ is a bond, and $R^4$ is —CH=CH—.

In some embodiments, $R^5$ is

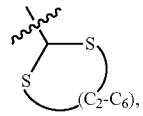

where $C_2$-$C_6$ represents a saturated 2 to 6 carbon alkyl chain which may be substituted or unsubstituted. In some embodiments, $R^1$ is a bond and $R^5$ is

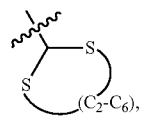

where $C_2$-$C_6$ represents a saturated 2 to 6 carbon alkyl chain which may be substituted or unsubstituted.

In some embodiments, $R^5$ is —(C($R^a$)($R^b$))$_n$—CN. In some embodiments, $R^1$ is a bond and $R^5$ is —(C($R^a$)($R^b$))$_n$—CN. In other embodiments, $R^5$ is —(C($R^a$)($R^b$))$_n$—N$^+$C$^-$. In other embodiments, $R^1$ is a bond and $R^5$ is —(C($R^a$)($R^b$))$_n$—N$^+$C$^-$.

In some embodiments, $R^1$ is a bond, $R^2$ is —[(C($R^a$)($R^b$))$_p$—O]$_q$ ($R^a$) or —C(O)—O$R^a$—, and wherein at least one $R^a$ is a $C_1$-$C_6$ alkyl group. In some embodiments, $R^1$ is —C(O)—$R^x$—. In some embodiments, $R^1$ is —C(O)—$R^x$—, and $R^5$ is —(C($R^a$)($R^b$))$_n$—N$_3$. In some embodiments, $R^5$ is derived from a substituted or unsubstituted 1,4-epoxy-1,4-dihydronaphthalene.

In some embodiments, $R^1$ is —CH$_2$—, and $R^5$ is —B(O$Z^1$)(O$Z^2$). In some embodiments, $Z^1$ and $Z^2$ are independently selected from the group consisting of H, methyl, and ethyl. In some embodiments, $R^1$ is —CH$_2$—, and $R^5$ is —B(OH)$_2$. In some embodiments, $R^1$ is —CH$_2$— and $R^5$ is —B(OH)$_2$.

In another aspect of the present disclosure are nucleotides or salts thereof having Formula (I):

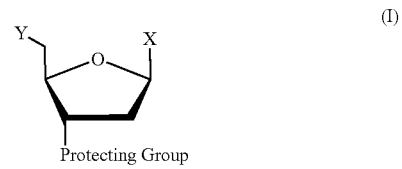

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

'Protecting Group' has the structure:

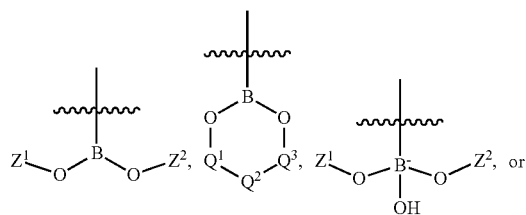

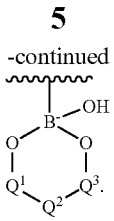

where $Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2; and $R^e$ and $R^f$ are independently H, methyl, ethyl, isopropyl, or a substituted or unsubstituted 5- or 6-membered aryl group.

In some embodiments, the 'Protecting Group' is —B(O$Z^1$)(O$Z^2$). In some embodiments, the 'Protecting Group' is —B(O$Z^1$)(O$Z^2$), where $Z^1$ and $Z^2$ are independently selected from a $C_1$-$C_4$ alkyl group. In some embodiments, the 'Protecting Group' is —B(OMe)(OMe). In some embodiments, the 'Protecting Group' is —B(OEt)(OEt). In some embodiments, the 'Protecting Group' is —B(O$Z^1$)(OH). In some embodiments, the 'Protecting Group' is —B(OH)$_2$. In some embodiments, the 'Protecting Group' is —B(OH)$_3^-$.

In another aspect of the present disclosure are nucleotides or salts thereof having Formula (IV):

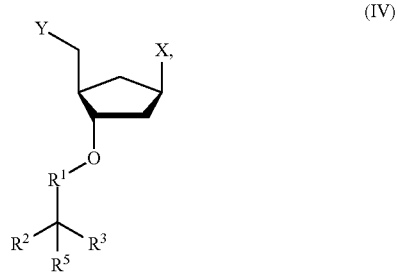

(IV)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, —C(O)—R$^x$—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

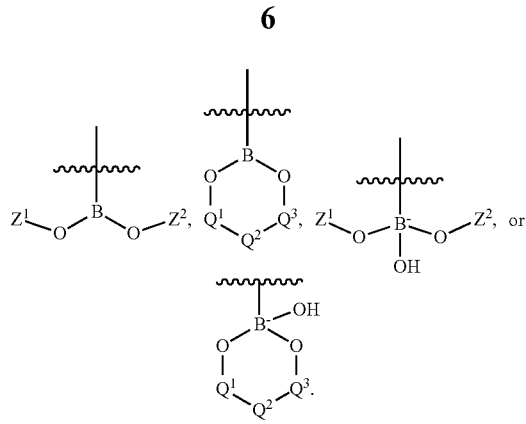

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

with the proviso that when $R^1$ is a bond and $R^2$ and $R^3$ are both H, $R^5$ is not an azide (e.g. $R^5$ is not N$^3$).

In some embodiments, $R^5$ is —B(O$Z^1$)(O$Z^2$). In some embodiments, $R^5$ is —B(O$Z^1$)(O$Z^2$), where $Z^1$ and $Z^2$ are independently selected from a $C_1$-$C_4$ alkyl group. In some embodiments, $R^5$ is —B(OMe)(OMe). In some embodiments, $R^5$ is —B(OEt)(OEt). In some embodiments, $R^5$ is —B(O$Z^1$)(OH). In some embodiments, $R^5$ is —B(OH)$_2$. In some embodiments, the 'Protecting Group' is —B(OH)$_3^-$.

In another aspect of the present disclosure are nucleotides or salts thereof having Formula (VA):

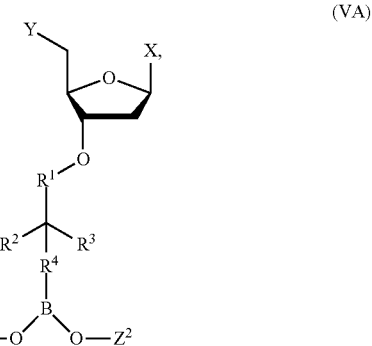

(VA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —$CH_2$—, —C(O)—O—, —C(O)—$NR^a$—, —C(O)—$R^x$—;

$R^2$ and $R^3$ are each independently H, a saturated or unsaturated $C_1$-$C_6$ alkyl group, a $C_5$-$C_6$ aryl or heteroaryl group, a halogen, —$[(C(R^a)(R^b))_p—O]_q$ ($R^a$), —C(O)—$OR^a$, —C(O)—N($R^a$)($R^b$), —$(C(R^a)(R^b))_n$—$N^+C^-$, —CN, or —$NO_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$Z^1$ and $Z^2$ are independently H, a $C_1$-$C_4$ alkyl group, or a 5- to 6-membered aryl group optionally substituted with one or more hydroxyl groups;

$R^a$ and $R^b$ are each independently H or a saturated $C_1$-$C_6$ alkyl group;

$R^x$ is a substituted or unsubstituted 5- or 6-membered aromatic group or heteroaromatic group; and p and q are each independently zero or an integer ranging from 1 to 3.

In some embodiments, $Z^1$ and $Z^2$ are independently selected from methyl or ethyl. In some embodiments, $Z^1$ and $Z^2$ are independently selected from methyl or ethyl, and $R^1$ is a bond. In some embodiments, $Z^1$ and $Z^2$ are independently selected from methyl or ethyl, and $R^1$ is a bond, and $R^2$ and $R^3$ are H.

In some embodiments, $Z^1$ is H and $Z^2$ is selected from methyl or ethyl. In some embodiments, $Z^1$ is H and $Z^2$ is selected from methyl or ethyl, and $R^1$ is a bond. In some embodiments, $Z^1$ is H and $Z^2$ is independently selected from methyl or ethyl, and $R^1$ is a bond, and $R^2$ and $R^3$ are H.

The present disclosure also provides methods of sequencing a nucleic acid sequence, the method utilizing the any of the nucleotides described herein (e.g. the nucleotides of any of Formulas (I) or (II)). In some embodiments, the nucleotide sequence of a portion of a target nucleic acid or fragment thereof can be determined using a variety of methods and devices. Non-limiting examples of sequencing methods include electrophoretic sequencing, sequencing by synthesis, sequencing by ligation, sequencing by hybridization, single-molecule sequencing, and real time sequencing methods.

In another aspect of the present disclosure is a method for determining the sequence of a target single-stranded polynucleotide, comprising monitoring the sequential incorporation of complementary nucleotides, wherein the complementary nucleotides each have the structure of any of Formulas (I), (II), (IIIA)-(IIID), (IV), (VA)-(VD), or (VIIIA)-(VIIIF) as described herein; and wherein the identity of each complementary nucleotide incorporated is determined through the detection of a tag (e.g. a detectable moiety) released from or attached to each of the complementary nucleotides. In some embodiments, the tag is released from each of the complementary nucleotides under the same conditions used to deprotect the 3'-protection group of complementary nucleotides of any of Formulas (I), (II), (IIIA)-(IIID), (IV), (VA)-(VD), or (VIIIA)-(VIIIF). In some embodiments, the tag is released by cleavage after its detection. In some embodiments, the method utilizes at least four different complementary nucleotides of any of Formulas (I), (II), (IIIA)-(IIID), (IV), (VA)-(VD), or (VIIIA)-(VIIIF), the at least four different complementary nucleotides each having a different nucleobase. In some embodiments, the tag is coupled to a nucleobase of the complementary nucleotide. In some embodiments, each of the at least four different complementary nucleotides has a different tag. In some embodiments, each of the at least four different complementary nucleotides has a different tag, but where each of the at least four different complementary nucleotides comprises the same protecting group, blocking group, or $R^5$ moiety (such as those groups are embodied in Formulas (I), (II), (IIIA)-(IIID), (IV), (VA)-(VD), or (VIIIA)-(VIIIF) herein).

In another aspect of the present disclosure is a method of sequencing a nucleic acid sequence comprising (a) performing a polymerization reaction with the aid of a single polymerase (e.g. DNA polymerase or a variant or mutant thereof) coupled to a nanopore, the polymerization reaction incorporating one of at least four different 3' protected nucleotides into a growing polynucleotide strand complementary to a single stranded nucleic acid molecule derived from the nucleic acid sample, each individual 3' protected nucleotide of the at least four different 3' protected nucleotides comprising a blocking group including a moiety having a structure:

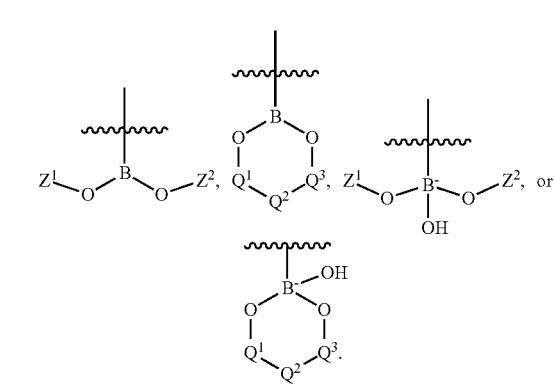

where $Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —$C(R^e)(R^f)$—, or —C(O)—;

$Q^2$ is a bond, o-phenylene, or —$[C(R^e)(R^f)]_w$—, where w is 1 or 2;

$R^e$ and $R^f$ are independently H, methyl, ethyl, isopropyl, or a substituted or unsubstituted 5- or 6-membered aryl group; and (b) detecting, with the aid of the nanopore, the incorporation of the 3' protected nucleotide or a byproduct thereof into the growing polynucleotide strand; and (c) either simultaneously with or subsequent to the step of detecting the incorporation of the 3' protected nucleotide or a byproduct thereof, deprotecting the 3' protected nucleotide to provide a 3' deprotected nucleotide. In some embodiments, the at least four different 3' protected nucleotides each comprise a different detectable moiety. In some embodiments, the step of detecting comprises detecting the different detectable moieties associated with each of the at least four different 3' protected nucleotides. In some embodiments, the method further comprises correlating the detected detectable moieties associated with each of the at least four different 3' protected nucleotides with a type of nucleotide. In some embodiments, the method further comprises generating a nucleic acid sequence of the nucleic acid molecule based upon an assessment of the detectable moieties detected during polymerization. In some embodiments, the deprotection comprises contacting the 3' protected nucleotide with an oxidant (e.g. hydrogen peroxide). In some embodiments, the method further comprises detecting a byproduct of the deprotection of the 3' protected nucleotides.

In another aspect of the present disclosure is a method of sequencing a nucleic acid sequence with the aid of a nanopore, comprising: (a) performing a polymerization reaction with the aid of a single polymerase coupled to a nanopore, the polymerization reaction incorporating one of at least four different 3' protected nucleotides into a growing polynucleotide strand complementary to a single stranded nucleic acid molecule derived from the nucleic acid sample, each individual 3' protected nucleotide of the at least four different 3' protected nucleotides are selected from those nucleotides of any of Formulas (I), (II), (IIIA)-(IIID), (IV), (VA)-(VD), or (VIIIA)-(VIIIF) as described herein; (b) detecting, with the aid of the nanopore, the incorporation of the 3' protected nucleotide or a byproduct thereof into the growing polynucleotide strand; and (c) either simultaneously with or subsequent to the step of detecting the incorporation of the 3' protected nucleotide or the byproduct derived thereof, deprotecting the 3' protected nucleotide to provide a 3' deprotected nucleotide.

In another aspect of the present disclosure is a method of sequencing a nucleic acid sample with the aid of a nanopore, comprising: (a) performing a polymerization reaction with the aid of a single enzyme (e.g. a polymerase) coupled to the nanopore, the polymerization reaction incorporating one of at least four different 3' protected nucleotides into a growing polynucleotide strand complementary to a single stranded nucleic acid molecule from the nucleic acid sample, each individual 3' protected nucleotide of the at least four different 3' protected nucleotides comprising a protecting group including a moiety having a structure:

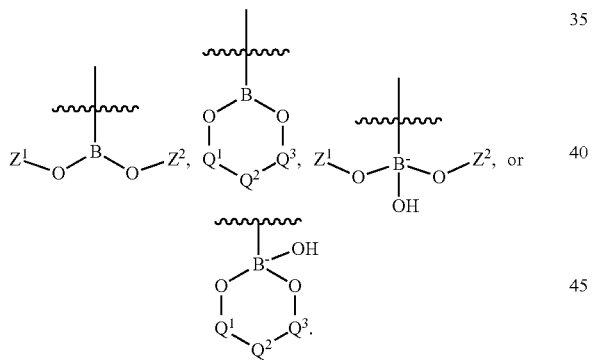

wherein
$Z^1$ and $Z^2$ are independently H, a $C_1$-$C_4$ alkyl group, or a 5- to 6-membered aryl group optionally substituted with one or more hydroxyl groups;
$Q^1$ and $Q^3$ are each independently a bond, —C($R^e$)($R^f$)—, or —C(O)—;
$Q^2$ is a bond, o-phenylene, or —[C($R^e$)($R^f$)]$_w$—, where w is 1 or 2;
$R^e$ and $R^f$ are independently H, methyl, ethyl, isopropyl, or a substituted or unsubstituted 5- or 6-membered aryl group; and
(b) detecting, with the aid of the nanopore, the incorporation of the 3' protected nucleotide into the growing polynucleotide strand; and (c) introducing an oxidant to deprotect a 3' protecting group and cleave a tag from the 3' protected nucleotide to provide a 3' —OH group (i.e. to provide a deprotected nucleotide). In some embodiments, the at least four different 3' protected nucleotides each comprise a different tag. In some embodiments, the step of detecting comprises detecting the different tags associated with each of the at least four different 3' protected nucleotides. In some embodiments, the method further comprises correlating the detected tag associated with each of the at least four different 3' protected nucleotides with a type of nucleotide. In some embodiments, the method further comprises generating a nucleic acid sequence of the nucleic acid molecule based upon an assessment of the tags detected during polymerization. In some embodiments, the deprotection comprises contacting the 3' protected nucleotide with an oxidant. In some embodiments, the oxidant is selected from the group consisting of hydrogen peroxide, sodium periodate, sodium perchlorate, peroxynitrate, or other appropriate oxidizing agent.

In another aspect of the present disclosure is a method for sequencing a nucleic acid molecule, the method comprising: (a) obtaining a chip comprising a plurality of individually addressable nanopores, wherein each individually addressable nanopore of the plurality of individually addressable nanopores comprises a nanopore in a membrane that is disposed adjacent to an electrode, wherein the nanopore is linked to an enzyme and wherein each individually addressable nanopore is adapted to detect a tag that is released from a 3' protected nucleotide, wherein the 3' protected nucleotide (or any salt thereof) is embodied by Formula (IIIA):

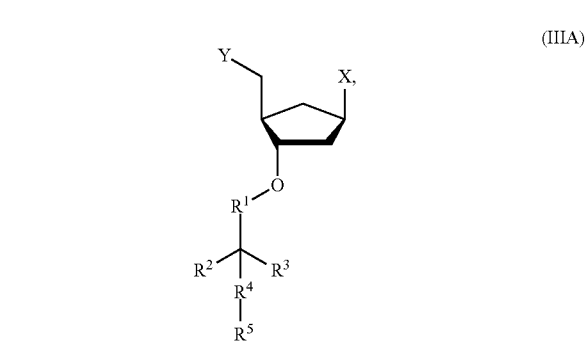

(IIIA)

wherein
X is a nucleobase or a tagged nucleobase;
Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;
$R^1$ is a bond, —$CH_2$—, —C(O)—O—, —C(O)—$NR^a$—, or —C(O)—$R^x$—;
$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—$OR^a$, —C(O)—N($R^a$)($R^b$), —(C($R^a$)($R^b$))$_n$—$N^+C^-$, —CN, or —$NO_2$;
$R^4$ is a bond, a substituted or unsubstituted 5- to 7-membered aryl group, —CH=CH—, a substituted or unsubstituted 5- or 6-membered heterocycloalkyl group, or —O—C(O)-aryl-;
$R^5$ is —(C($R^a$)($R^b$))$_n$—$N_3$, —(C($R^a$)($R^b$))$_n$—$N^+C^-$, —(C($R^a$)($R^b$))$_n$—CN, a 5- to 8-membered cycloalkyl group comprising two sulfur atoms positioned 1, 3 relative to each other, or a group having the structure:

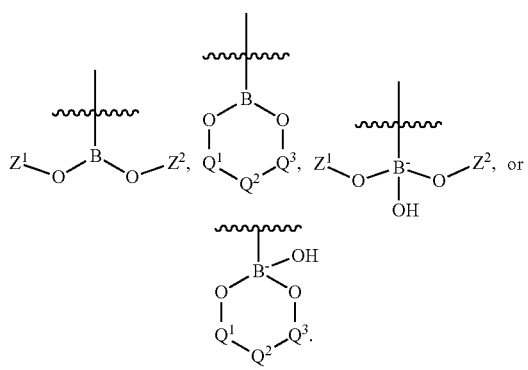

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond or —[C($R^e$)($R^f$)]$_w$—, where w is 1 or 2, or o-phenylene;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide (e.g. $R^5$ is no $N_3$);

(b) directing the nucleic acid molecule adjacent to or in proximity to the nanopore; (c) with the aid of the enzyme, polymerizing the 3' protected nucleotide along the nucleic acid molecule to generate a polynucleotide strand that is complementary to at least a portion of the nucleic acid molecule; (d) deprotecting the 3' protecting group of the 3' protected nucleotide after incorporation of the 3' protected nucleotide into the polynucleotide strand; and (e) detecting the tag released from the 3' protected nucleotide with the aid of the electrode, wherein the released tag flow through or in proximity to the nanopore. In some embodiments, the tag is released prior to deprotection of the 3' protecting group of the 3' protected nucleotide. In some embodiments, the tag is released simultaneously with the deprotection of the 3' protected nucleotide. In some embodiments, the tag is deprotected prior to the release of the protecting group. In some embodiments, the step of deprotection of the 3' protected nucleotide comprises contacting the 3' protected nucleotide with an oxidant, e.g. hydrogen peroxide. In some embodiments, the same reaction conditions and/or reagents are used for deprotection of 3'-protecting group and to release the tag.

In another aspect of the present disclosure is a kit comprising: a biochip comprising a semiconductor substrate having a plurality of wells at a density of at least about 250 wells/mm², and an electrode disposed in each of the plurality of wells; and at least one of the nucleotides of any of Formulas (I), (II), (IIIA)-(IIID), (IV), (VA)-(VD), or (VIIIA)-(VIIIF) herein. In some embodiments, the at least one of the nucleotides comprises a moiety derived from boronic acid or a derivative or analog thereof. In some embodiments, the density of the wells is at least about 500 wells/mm². In some embodiments, the at least one of the nucleotides comprises a detectable moiety, wherein the detectable moiety is coupled to a nucleobase via a cleavable linker. In some embodiments, the cleavable linker may be cleaved using an oxidant. In some embodiments, the detectable moiety includes oligonucleotides, oligopeptides, polypeptides, oligophosphates, PEG groups, and other moieties.

In another aspect of the present disclosure is a kit comprising: (a) at least one of the nucleotides of any one of Formulas (I), (II), (IIIA)-(IIID), (IV), (VA)-(VD), or (VIIIA)-(VIIIF) herein; and (b) an oxidant. In some embodiments, the kit further comprises a base. In some embodiments, the at least one of the nucleotides of any one of Formulas (I), (II), (IIIA)-(IIID), (IV), (VA)-(VD), or (VIIIA)-(VIIIF) is provided in a first container; and wherein the oxidant is provided in a second container.

In another aspect of the present disclosure is an assembly comprising: a reservoir, the reservoir comprising at least one of the nucleotides of any one of Formulas (I), (II), (IIIA)-(IIID), (IV), (VA)-(VD), or (VIIIA)-(VIIIF); a biochip comprising a semiconductor substrate having a plurality of wells at a density of at least about 250 wells/mm²; an electrode disposed in each of the plurality of wells; and a counter electrode disposed on a biochip facing surface of the reservoir. In some embodiments, at least one of the nucleotides comprises a moiety derived from boronic acid or a derivative or analog thereof. In some embodiments, the reservoir further comprises a byproduct derived from the deprotection of the nucleotide. In some embodiments, the byproduct is boric acid or a derivative or analog thereof.

In another aspect of the present disclosure is a composition comprising: a polynucleotide, and at least one of boric acid or a derivative or analog thereof, a quinone methide, an acetal, an aldehyde, an acrylaldehyde, and 4-methylene-2,5-cyclohexadien-1-one. In some embodiments, the composition further comprises a nucleotide of Formula (VIA) (or a salt thereof), or a trace amount of a nucleotide of Formula (VIA) (or a salt thereof).

In another aspect of the present disclosure is a nucleotide or salt thereof, wherein the nucleotide is selected from the group consisting of:

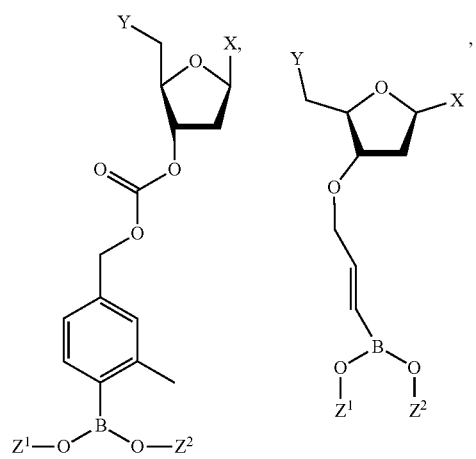

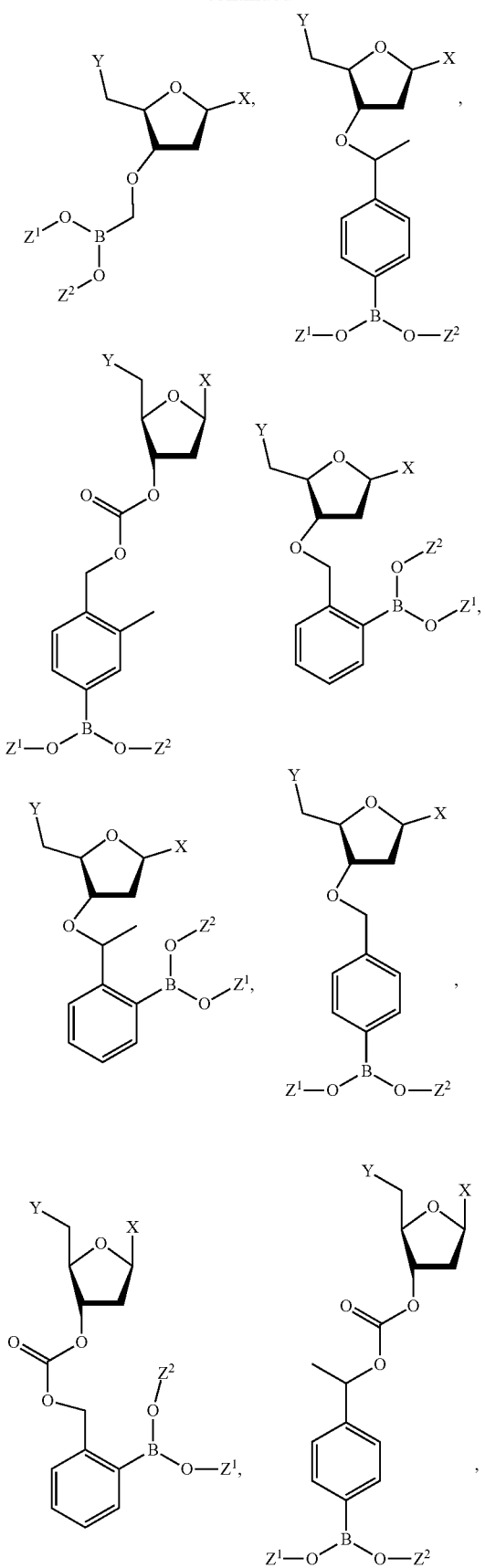
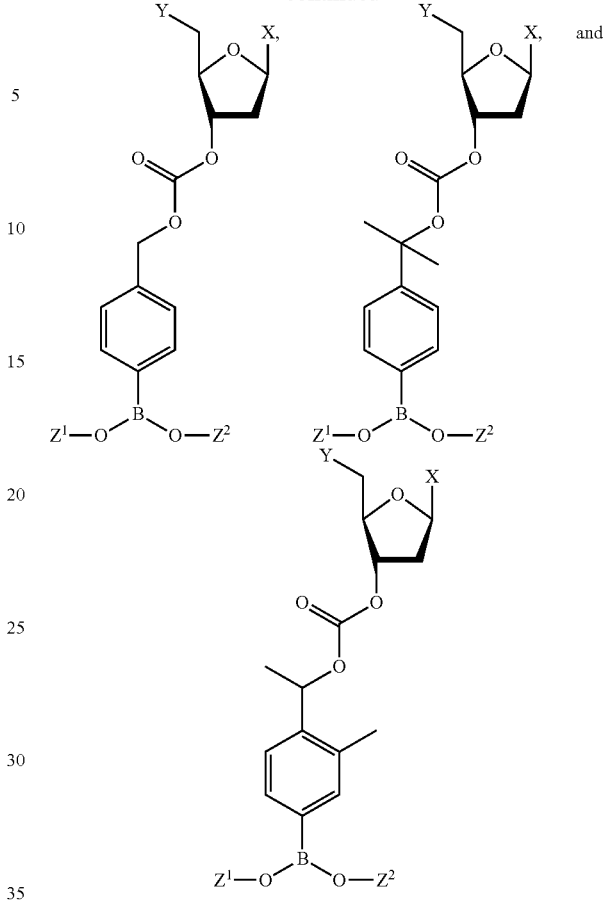

where
X is a nucleobase or a tagged nucleobase;
Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5; and
$Z^1$ and $Z^2$ are independently H or a $C_1$-$C_4$ alkyl group.

In some embodiments, $Z^1$ and $Z^2$ are independently H, methyl, or ethyl. In some embodiments, at least one of $Z^1$ or $Z^2$ is H.

In some embodiments, the nucleotide or salt thereof comprises a tag selected from the group consisting of one or more of ethylene glycol or a polymer derived from ethylene glycol, an amino acid, a carbohydrate, a peptide, a dye (including fluorophores), a chemiluminescent compound, a mass tag, a mononucleotide, a dinucleotide, a trinucleotide, a tetranucleotide, a pentanucleotide, a hexanucleotide, an oligonucleotide, a modified oligonucleotide, an aliphatic acid, an aromatic acid, an alcohol, a thiol group, a cyano group, a nitro group, an alkyl group, an alkenyl group, an alkynyl group, an azido group, and any combination thereof. In some embodiments, the nucleobase or salt thereof comprises a PEG-based tag. In some embodiments, the tagged nucleobase comprises a cleavable linker. In some embodiments, the cleavable linker is cleaved with an oxidant (e.g. hydrogen peroxide).

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1:
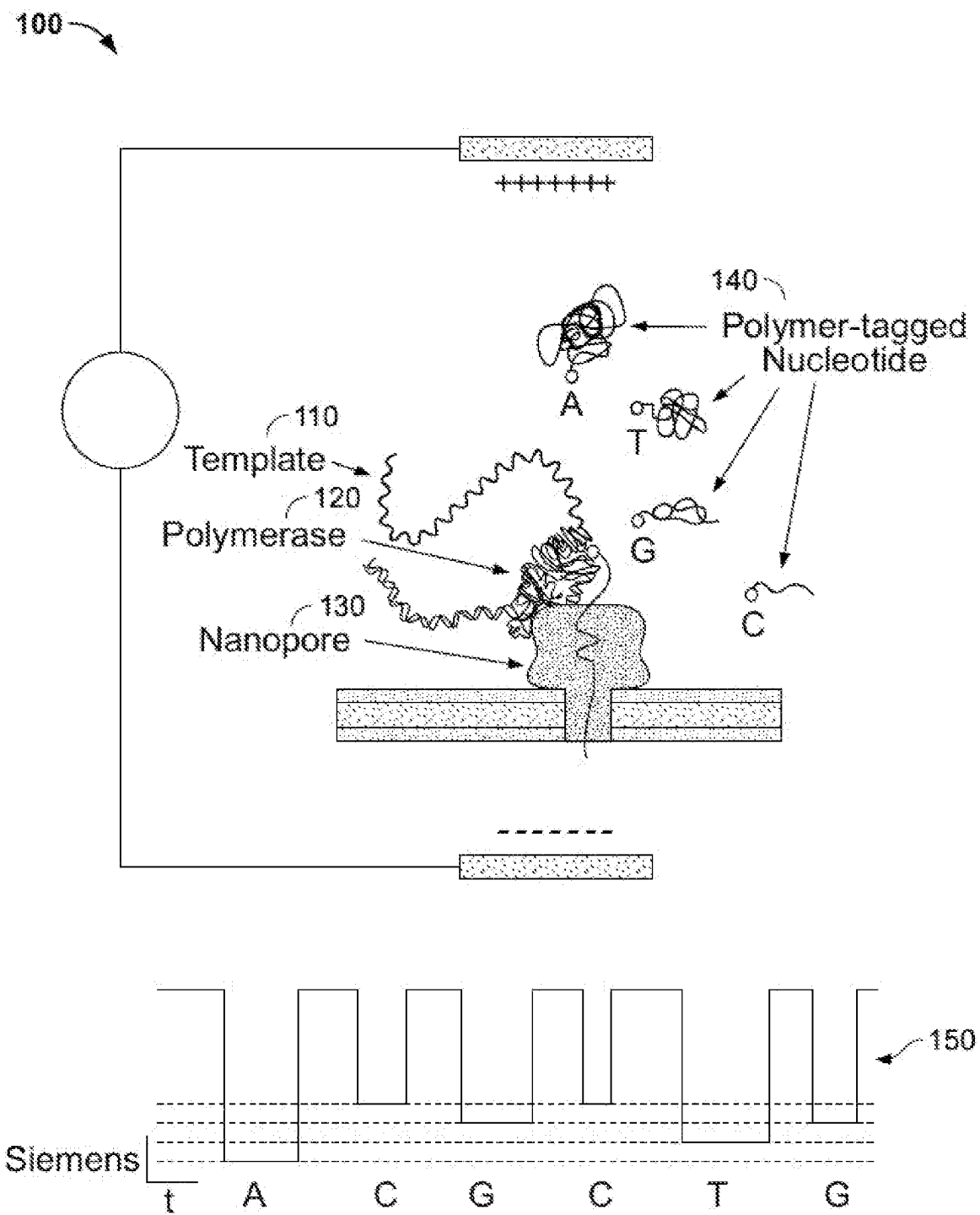
FIG. 1 illustrates single molecule DNA sequencing by a nanopore with polymer-tagged nucleotides (140). Each of the four nucleotides carry a different tag. During nanopore sequencing, these tags, attached via the terminal phosphate at 5' of the nucleotide, are released into the nanopore (130) one at a time where they produce unique current blockade signatures (150).

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the terms "analog" or "derivative" are used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

As used herein, the term "aliphatic" means a straight or branched hydrocarbon chain, which may be saturated or mono- or polyunsaturated. An unsaturated, aliphatic group contains one or more double and/or triple bonds. The branches of the hydrocarbon chain may include linear chains as well as non-aromatic cyclic elements. The hydrocarbon chain, which may, unless otherwise stated, be of any length, and contain any number of branches. Both the main chain as well as the branches may furthermore contain heteroatoms as for instance B, N, O, P, S, Se or Si.

As used herein, the term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). An "alkyl" is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-butadienyl, 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen atom (—O—).

As used herein, the term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

As used herein, the term "alkylene" means, in some embodiments, a linear, branched or cyclic alkylene group having one to three carbon atoms and may be, for example, a methylene group, an ethylene group, a propylene group, an isopropylene group or a c-propylene group.

As used herein, the term "aromatic" means, unless otherwise stated, a planar cyclic hydrocarbon moiety of conjugated double bonds, which may be a single ring or include multiple fused or covalently linked rings. The main chain of the cyclic hydrocarbon moiety may, unless otherwise stated, be of any length and contain any number of heteroatoms, as for instance N, O and S.

As used herein, the term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen, phosphorus, and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. A heteroalkyl is not cyclized. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—O—$CH_3$, S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, $CH_2$—NH—$OCH_3$.

As used herein, the terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Cycloalkyls and heterocycloalkyl can be further substituted, e.g., with any of the substituents described herein.

Each of the above terms (e.g., "alkyl," "aromatic," "heteroalkyl," "cycloalkyl," etc.) includes both substituted and unsubstituted forms of the indicated radical. In that regard, whenever a group or moiety is described as being "substituted" or "optionally substituted" (or "optionally having" or "optionally comprising") that group may be unsubstituted or substituted with one or more of the indicated substituents. Likewise, when a group is described as being "substituted or unsubstituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, cyanate, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an ether, amino (e.g. a mono-substituted amino group or a di-substituted amino group), and protected derivatives thereof. Any of the above groups may include one or more heteroatoms, including O, N, or S. For example, where a moiety is substituted with an alkyl group, that alkyl group may comprise a heteroatom selected from O, N, or S (e.g. —($CH_2$—$CH_2$—O—$CH_2$—$CH_3$)).

As used herein, the terms "couple" or "coupling" refer to the joining, bonding (e.g. covalent bonding), or linking of one molecule or atom to another molecule or atom.

As used herein, the terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

As used herein, the terms "heteroatom" or "ring heteroatom" are meant to include boron (B), oxygen (O), nitrogen (N), sulfur (S), phosphorus (P), and silicon (Si). In some embodiments, a "heterocyclic ring" may comprise one or more heteroatoms.

As used herein, the "lower substituent" or "lower substituent group," means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

As used herein, the term "nanopore" refers to a pore, channel or passage formed or otherwise provided in a membrane. A nanopore can be defined by a molecule (e.g., protein) in a membrane. A membrane can be an organic membrane, such as a lipid bilayer, or a synthetic membrane, such as a membrane formed of a polymeric material. As used herein, the term "polymer" is defined as being inclusive of homopolymers and copolymers. The term "homopolymer" is defined as a polymer derived from a single species of monomer. The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc. The nanopore may be disposed adjacent or in proximity to a sensing circuit, such as, for example, a complementary metal-oxide semiconductor (CMOS) or field effect transistor (FET) circuit. A nanopore may have a characteristic width or diameter on the order of 0.1 nanometers (nm) to about 1000 nm. Some nanopores are proteins. Alpha hemolysin is an example of a protein nanopore. In some embodiments, the nanopore is a solid state nanopore (e.g. a solid-state nanopore is typically a nanometer-sized hole formed in a synthetic membrane (usually SiNx or SiO2)).

As used herein, the term "nanopore sequencing complex" refers to a nanopore linked or coupled to an enzyme, e.g., a polymerase, which in turn is associated with a polymer, e.g., a polynucleotide template. The nanopore sequencing complex is positioned in a membrane, e.g., a lipid bilayer, where it functions to identify polymer components, e.g., nucleotides or amino acids.

As used herein, the terms "nanopore sequencing" or "nanopore-based sequencing" refer to a method that determines the sequence of a polynucleotide with the aid of a nanopore. In some embodiments, the sequence of the polynucleotide is determined in a template-dependent manner. The methods disclosed herein are not limited to any nanopore sequencing method, system, or device.

As used herein, the term "nucleic acid" refers to a molecule comprising one or more nucleic acid subunits. A nucleic acid can include one or more subunits (naturally occurring, synthetic, or modified nucleobases) including, but not limited to, adenosine (A), cytosine (C), guanine (G), thymine (T) and uracil (U). Derivatives of these bases are exemplified in PCR Systems, Reagents and Consumables (Perkin Elmer Catalogue 1996-1997, Roche Molecular Systems, Inc., Branchburg, N.J., USA), which is entirely incorporated herein by reference. In some examples, a nucleic acid is deoxyribonucleic acid (DNA) or ribonucleic acid (RNA), or derivatives thereof. A nucleic acid may be single-stranded or double stranded. A nucleic acid can include any nucleic acid molecule, including, without limitation, DNA, RNA and hybrids or variants thereof.

As used herein, the term "nucleobase" refers to a heterocyclic moiety capable of non-covalently pairing with another nucleobase. A "naturally occurring nucleobase" or an "unmodified nucleobase" (used interchangeably) refer to a nucleobase that is unmodified relative to its naturally occurring form. Likewise, a "modified nucleobase" means any substitution and/or change from a natural nucleobase. Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278). Additional modified nucleobases include, but are not limited to, 5-hydroxymethyl cytosine, xanthine, hypoxanthine, 7-methylguanine, 2-aminoadenine, 2-aminopurine, iso-C, iso-G, thioT, thioG, 5,6-dihydrouracil, 6-methyladenine, 2-propylguanine and other alkyl derivatives of adenine and guanine, 2-thiouracil, 2-thiothymine and 2-thiocytosine, 5-halouracil and cytosine such as 5-bromo, 5-trifluoromethyl and other 5-substituted uracils and cytosines, 5-propynyl (—C≡C—CH3) uracil and cytosine and other alkynyl derivatives of pyrimidine bases, 6-aza uracil, cytosine and thymine, uracil-5-yl (pseudouracil), 4-thiouracil, 8-halo, 8-amino, 8-thiol, 8-thioalkyl, 8-hydroxy and other 8-substituted adenines and guanines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine, 8-aza-7-deazaguanine and 8-aza-7-deazaadenine. Additional nucleobases are disclosed in Greco et. al., Synthesis and site-specific incorporation of a simple fluorescent pyrimidine, Nature Protocols, vol. 2, no. 2, 2007; Dien et. al., Progress Toward a Semi-Synthetic Organism with an Unrestricted Expanded Genetic Alphabet, J. Am. Chem. Soc. 2018, 140, 16115-16123; Zhang et. al., Evolution of Functional Six-Nucleotide DNA, J. Am. Chem. Soc. 2015, 137, 6734-6737; Biondi et. al. Artificially Expanded Genetic Information Systems for New Aptamer Technologies, Biomedicines 2018, 6, 53; Liu et. al., Helix-Forming Properties of Size-Expanded DNA, an Alternative Four-Base Genetic Form, J. Am. Chem. Soc. 9 Vol. 127, No. 5, 2005, 1396-1402; Tor et. al., Designing new isomorphic fluorescent nucleobase analogues: the thieno[3,2-d]pyrimidine core, Tetrahedron 63 (2007) 3608-3614; Laos et. al., Directed Evolution of Polymerases to Accept Nucleotides with Nonstandard Hydrogen Bond Patterns, Biochemistry 2013, 52, 5288-5294; Krueger et. al., Synthesis and Properties of Size-expanded DNAs: Toward Designed, Functional Genetic Systems, Acc Chem Res. 2007 February; 40(2): 141-150; Srivatsan et. al., A highly fluorescent nucleoside analog based on thieno[3,4-d]pyrimidine senses mismatched pairing, Org. Biomol. Chem., 2008, 6, 1334-1338; Kim et. al., Synthesis and Properties of 5-Cyano-Substituted Nucleoside Analog with a Donor-Donor-Acceptor Hydrogen-Bonding Pattern, J. Org. Chem. 2012, 77, 3664-3669; and Noe et. al., Oligodeoxynucleotides Containing Multiple Thiophene-Modified Isomorphic Fluorescent Nucleosides, J. Org. Chem. 2013, 78, 8123-8128, the disclosures of which are hereby incorporated by reference herein in their entireties.

As used herein, the term "nucleoside" refers to a nucleobase covalently attached to a sugar, such as ribose or 2'-deoxyribose.

As used herein, the term "nucleotide" refers to a nucleoside covalently attached to a phosphate or polyphosphate, such as adenosine 5'-monophosphate (AMP), adenosine 5'-diphosphate (ADP), adenosine 5'-triphosphate (ATP), adenosine 5'-tetraphosphate or its 2'-deoxy derivatives. As used herein, the term "oligonucleotide," refers to an oligomer of nucleotide or nucleoside monomer units wherein the oligomer optionally includes non-nucleotide monomer units, and/or other chemical groups attached at internal and/or external positions of the oligomer. The oligomer can be natural or synthetic and can include naturally-occurring oligonucleotides, or oligomers that include nucleosides with non-naturally-occurring (or modified) bases, sugar moieties, phosphodiester-analog linkages, and/or alternative monomer unit chiralities and isomeric structures (e.g., 5'- to 2'-linkage, L-nucleosides, α-anomer nucleosides). Exemplary oligonucleotides useful as nanopore-detectable tags in the composition and methods of the present disclosure include the oligonucleotide tag structures shown in Table 4.

As used herein, the term "polymerase" refers to any enzyme capable of catalyzing a polymerization reaction. Examples of polymerases include, without limitation, a nucleic acid polymerase, a transcriptase or a ligase. A polymerase can be a polymerization enzyme. A "DNA polymerase" catalyzes the polymerization of deoxynucleotides. An "RNA polymerase" catalyzes the polymerization of ribonucleotides. A polymer may include a reverse transcriptase, an enzyme used to generate complementary DNA (cDNA) from an RNA template.

As used herein, a "polynucleotide" is a polymer or oligomer comprising at least two nucleotides. A polynucleotide or oligonucleotide can comprise a DNA polynucleotide or oligonucleotide, an RNA polynucleotide or oligonucleotide, or one or more sections of DNA polynucleotide or oligonucleotide and/or RNA polynucleotide or oligonucleotide.

As used herein, the terms "reactive group" or "reactive functional group" refer to a functional group that are capable of chemically associating with, interacting with, hybridizing with, hydrogen bonding with, or coupling with a functional group of a different moiety. In some embodiments, a "reaction" between two reactive groups or two reactive functional groups may mean that a covalent linkage is formed between two reactive groups or two reactive functional groups; or may mean that the two reactive groups or two reactive functional groups associate with each other, interact with each other, hybridize to each other, hydrogen bond with each other, etc. In some embodiments, the "reaction" thus includes binding events, such as the binding of a hapten with an anti-hapten antibody, or a guest molecule associating with a supramolecular host molecule.

As used herein, the term "sequencing" refers to the determination of the order and position of bases in a nucleic acid.

As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

The headings provided herein are for convenience only and do not interpret the scope or meaning of the disclosed embodiments.

Nucleotides

The present disclosure is directed to nucleotides and/or nucleosides (or any salts thereof) including a sugar, e.g. ribose or deoxyribose, having a 3' removable protecting group. In some embodiments, the nucleotides and/or nucleosides of the present disclosure include a tagged nucleobase, e.g. a base including a detectable moiety. In some embodiments, the 3' removable protecting group satisfies at least one criteria such as (i) the ability of an enzyme (e.g. a polymerase) to accurately and efficiently incorporate the nucleotides or nucleosides carrying the 3' removable protecting groups into a growing oligonucleotide; (ii) the availability of mild conditions for rapid and quantitative deprotection, and (iii) the ability of the enzyme to reinitiate oligomer synthesis subsequent to the deprotection step. In some embodiments, the 3' protecting group is removed under non-reductive conditions (e.g. using hydrogen peroxide or another oxidant).

In some embodiments, nucleotides (including any salts thereof) according to the present disclosure have a structure embodied by Formula (I):

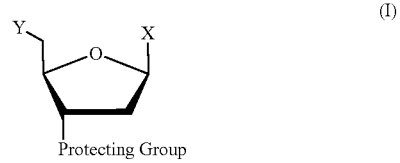

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

'Protecting Group' has the structure:

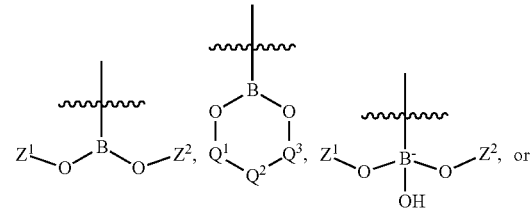

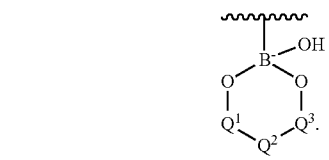

where $Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2; and $R^e$ and $R^f$ are independently H, methyl, ethyl, isopropyl, or a substituted or unsubstituted 5- or 6-membered aryl group.

In some embodiments, the oligonucleotide of Y is coupled via its 3' terminus.

In some embodiments, the 'Protecting Group' is —B(O$Z^1$)(O$Z^2$). In some embodiments, one of $Z^1$ or $Z^2$ is H, methyl, or ethyl. In some embodiments, both of $Z^1$ and $Z^2$ are independently selected from H, methyl, or ethyl. In some embodiments, $Z^1$ and $Z^2$ are independently selected from methyl or ethyl. In some embodiments, the 'Protecting Group' is —B(OH)$_2$. In some embodiments, the 'Protecting Group' is —B(OH)$_3^-$.

In some embodiments, nucleotides (including any salts thereof) according to the present disclosure have a structure embodied by Formula (II):

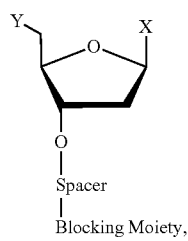

(II)

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

'Spacer' is a straight chain or branched, substituted or unsubstituted, saturated or unsaturated, aliphatic or aromatic group having between 1 and 16 carbon atoms and optionally substituted with one or more heteroatoms;

'Blocking Moiety' is a straight chain or branched, substituted or unsubstituted, saturated or unsaturated, aliphatic or aromatic group having between 1 and 20 carbon atoms, and optionally substituted with one or more heteroatoms, and provided that the 'Blocking Moiety' includes an azide group, an isonitrile group, a cyano group, a 5- to 8-membered heterocycloalkyl group having at least one heteroatom selected from O, N, S, or Se, a moiety derived from a substituted or unsubstituted 1,4-epoxy-1,4-dihydronaphthalene, or a group having the structure:

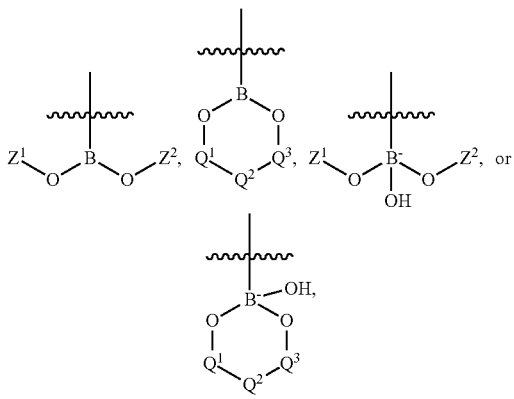

where $Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2; and $R^e$ and $R^f$ are independently H, methyl, ethyl, isopropyl, or a substituted or unsubstituted 5- or 6-membered aryl group;

provided that when the 'Blocking Moiety' is —N$_3$, the 'Spacer' is not —CH$_2$—.

In some embodiments, the 'Spacer' is a straight chain or branched, substituted or unsubstituted, saturated or unsaturated, aliphatic group having between 1 and 12 carbon atoms and optionally including a carbonyl group. In other embodiments, the 'Spacer' is a straight chain or branched, substituted or unsubstituted, saturated or unsaturated, aliphatic group having between 1 and 10 carbon atoms and optionally includes a ketone, an ester or an amide. In yet other embodiments, the 'Spacer' is a straight chain or branched, substituted or unsubstituted, saturated or unsaturated, aliphatic group having between 1 and 6 carbon atoms and includes a carbonyl group, e.g. a ketone, an ester, a carbonate, a carbamate, a urethane, or an amide.

In some embodiments, the 'Blocking Moiety' is a straight chain or branched, substituted or unsubstituted, saturated or unsaturated, aliphatic or aromatic group having between 1 and 20 carbon atoms, and optionally substituted with one or more heteroatoms, and provided that the 'Blocking Moiety' includes an isonitrile group, a cyano group, a 5- to 8-membered heterocycloalkyl group having at least one heteroatom selected from O, N, S, or Se, a moiety derived from a substituted or unsubstituted 1,4-epoxy-1,4-dihydronaphthalene, or a moiety derived from boronic acid or a derivative or analog thereof. In some embodiments, the 'Blocking Moiety' is a straight chain or branched, substituted or unsubstituted, saturated or unsaturated, aliphatic or aromatic group having between 1 and 16 carbon atoms. In other embodiments, the 'Blocking Moiety' is a straight chain or branched, substituted or unsubstituted, saturated or unsaturated, aliphatic or aromatic group having between 1 and 12 carbon atoms. In yet other embodiments, the 'Blocking Moiety' is a straight chain or branched, substituted or unsubstituted, saturated or unsaturated, aliphatic or aromatic group having between 1 and 6 carbon atoms.

In other embodiments, the 'Blocking Moiety' includes a —B($OZ^1$)($OZ^2$) group, where $Z^1$ and $Z^2$ are independently selected from H, methyl, ethyl, isopropyl, or tertbutyl. In other embodiments, the 'Blocking Moiety' includes a —B($OZ^1$)($OZ^2$) group, where $Z^1$ and $Z^2$ are independently selected from H, methyl, or ethyl. In other embodiments, the 'Blocking Moiety' includes a —B($OZ^1$)($OZ^2$) group, where only one of $Z^1$ or $Z^2$ is H. In yet other embodiments, the 'Blocking Moiety' includes a —B($OZ^1$)($OZ^2$) group, where both $Z^1$ and $Z^2$ are H. In some embodiments, the 'Protecting Group' is —B(OH)$_3$—.

In other embodiments, the 'Blocking Moiety' includes a 5- to 8-membered heterocycloalkyl group which includes at least one sulfur atom or selenium atom. In other embodiments, the 'Blocking Moiety' includes a 5- to 8-membered heterocycloalkyl group which includes two sulfur atoms or two selenium atoms, where the two sulfur atoms or two selenium atoms are separated from each other by one carbon atom (e.g. —S—C—S— or —Se—C—Se—). In some embodiments, the 5- to 8-membered heterocycloalkyl group is a 1,3-dithiane group.

In some embodiments, nucleotides (including any salts thereof) according to the present disclosure have a structure as embodied by Formula (IIIA):

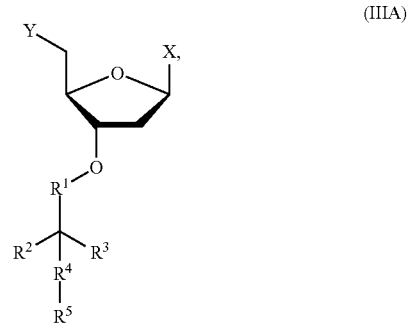

(IIIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$—(R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$R^5$ is —(C(R$^a$)(R$^b$))$_n$—N$_3$, —(C(R$^a$)(R$^b$))$_n$—N$^+$C$^-$, —(C(R$^a$)(R$^b$))$_n$—CN, a 5- to 8-membered cycloalkyl group comprising two sulfur atoms positioned 1, 3 relative to each other, or a group having the structure:

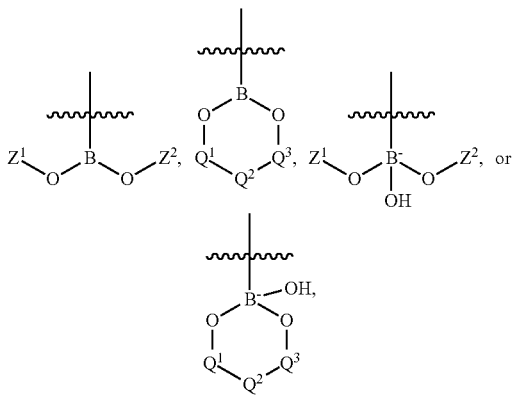

where $Z^1$ and $Z^2$ are independently H, a C$_1$-C$_4$ alkyl group, or a 5- to 6-membered aryl group optionally substituted with one or more hydroxyl groups;

$Q^1$ and $Q^3$ are each independently a bond, —C(R$^e$)(R$^f$)—, or —C(O)—;

$Q^2$ is a bond, o-phenylene, or —[C(R$^e$)(R$^f$)]$_w$—, where w is 1 or 2;

$R^a$ and $R^b$ are each independently H or a saturated C$_1$-C$_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide.

In some embodiments, $R^1$ is a —CH$_2$—, and $R^5$ is —B(OZ$^1$)(OZ$^2$). In some embodiments, $R^1$ is a —CH$_2$—, $R^4$ is a bond, and $R^5$ is —B(OZ$^1$)(OZ$^2$). In some embodiments, $R^1$ is a —CH$_2$—, $R^4$ is a bond, and $R^5$ is —B(OZ$^1$)(OZ$^2$), and at least one of $R^2$ or $R^3$ is H.

In some embodiments, at least one of $R^2$ or $R^3$ is a H. In other embodiments, one of $R^2$ or $R^3$ is —[(C(R$^a$)(R$^b$))$_p$—O]$_q$(R$^a$) or —C(O)—OR$^a$—. In yet other embodiments, one of $R^2$ or $R^3$ is —[(C(R$^a$)(R$^b$))$_p$—O]$_q$—(R$^a$) or —C(O)—OR$^a$— and R$^a$ is methyl or ethyl. In further embodiments, one of $R^2$ or $R^3$ is selected from methyl, ethyl, isopropyl, or tertbutyl. In yet further embodiments, at least one of $R^2$ or $R^3$ is H, $R^5$ is —B(OZ$^1$)(OZ$^2$), and one of $Z^1$ or $Z^2$ is H. In even further embodiments, both $R^2$ and $R^3$ are H, $R^5$ is —B(OZ$^1$)(OZ$^2$), and both of $Z^1$ and $Z^2$ are H. In some embodiments, $R^1$ is a bond, $R^2$ and $R^3$ are both H, $R^4$ is a bond, and $R^5$ is —B(OZ$^1$)(OZ$^2$). In some embodiments, the 'Protecting Group' is —B(OH)$_3^-$.

In some embodiments, $R^4$ is a phenyl group or a 5- or 6-membered heterocycloalkyl group which is substituted with at least one moiety selected from the group consisting of —OR$^6$, halogen, a C$_1$-C$_6$ alkyl group, a C$_2$-C$_6$ alkenyl group, —C(O)—R$^c$, —C(O)—N(R$^c$)(R$^d$), or —NO$_2$, where R$^c$ and R$^d$ are each independently H or a saturated C$_1$-C$_6$ alkyl group; and wherein R$^6$ is a C$_1$ to C$_6$ alkyl group, —N—(R$^a$)(R$^b$), or —O(R$^a$). In other embodiments, R$^6$ is a C$_1$ to C$_4$ alkyl group. In yet other embodiments, R$^6$ is selected from methyl, ethyl, isopropyl, or tertbutyl.

In some embodiments, $R^4$ is a substituted or unsubstituted phenyl group. In other embodiments, $R^4$ is a phenyl group substituted with one or more electron withdrawing groups (e.g. nitro (—NO$_2$), cyano (—CN), carboxamide (—C(O)NH$_2$), trifluoromethyl (—CF$_3$)). In some embodiments, the phenyl group is substituted with 1, 2, or 3 electron withdrawing groups. In yet other embodiments, $R^4$ is a phenyl group substituted with an electron withdrawing group. In further embodiments, $R^4$ is an unsubstituted phenyl group.

In some embodiments, $R^4$ is a substituted heterocycloalkyl group. In other embodiments, $R^4$ is a heterocycloalkyl group substituted with one or more electron withdrawing groups (e.g. nitro (—NO$_2$), cyano (—CN), carboxamide (—C(O)NH$_2$), trifluoromethyl (—CF$_3$)). In yet other embodiments, $R^4$ is a heterocycloalkyl group substituted with an electron withdrawing group. In further embodiments, $R^4$ is an unsubstituted heterocycloalkyl group.

In other embodiments, $R^4$ is a phenyl group or a 5- or 6-membered heterocycloalkyl group which is substituted with at least one alkyl substituent, where each alkyl substituent is selected from methyl, ethyl, isopropyl, or tertbutyl.

In some embodiments, $R^5$ is —B(OZ$^1$)(OZ$^2$), and $Z^1$ and $Z^2$ are independently selected from H, methyl, ethyl, isopropyl, or tertbutyl. In other embodiments, $R^5$ is —B(OZ$^1$)(OZ$^2$), and one of $Z^1$ or $Z^2$ is H. In yet other embodiments, $R^5$ is —B(OZ$^1$)(OZ$^2$), and both $Z^1$ and $Z^2$ are H. In some embodiments, $R^4$ is a bond, $R^5$ is —B(OZ$^1$)(OZ$^2$), and $Z^1$ and $Z^2$ are independently selected from H, methyl, ethyl, isopropyl, or tertbutyl. In other embodiments, $R^4$ is a bond, $R^5$ is —B(OZ$^1$)(OZ$^2$), and both $Z^1$ and $Z^2$ are H.

In some embodiments, $R^5$ is

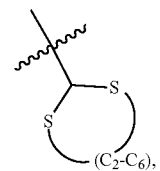

where C$_2$-C$_6$ represents a saturated 2 to 6 carbon alkyl chain which may be substituted or unsubstituted. In some embodiments, the group

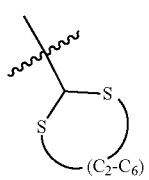

contains at least one substituent selected from methyl, ethyl, isopropyl, or tertbutyl. In some embodiments, $R^5$ is

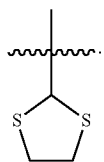

In other embodiments, $R^5$ is

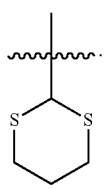

Non-limiting examples of the nucleotides (including any salts thereof) of Formula (IIIA) include:

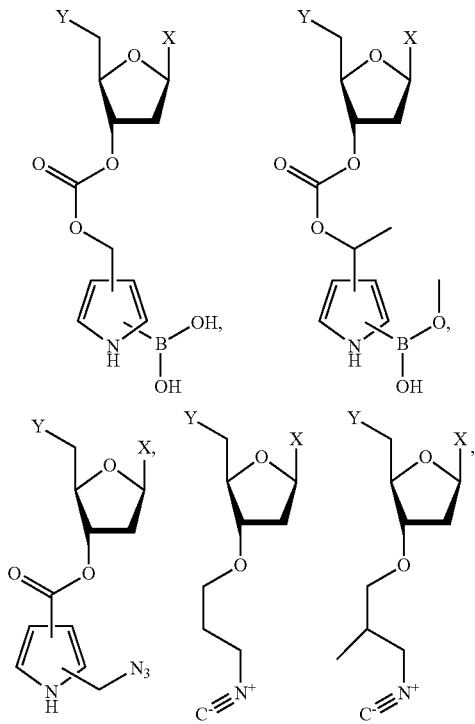

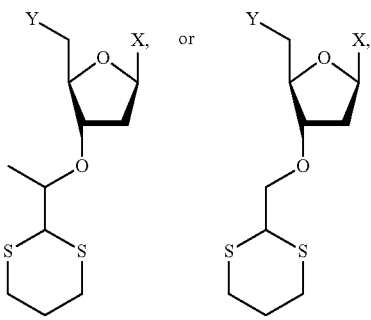

wherein

X is a nucleobase or a tagged nucleobase; and

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5.

In some embodiments, the heterocyclic group in the above-identified examples are substituted at the 2,3 positions or the 2,5 positions.

In some embodiments, the nucleotides (including any salts thereof) of the present disclosure have a structure as embodied by Formula (IIIB):

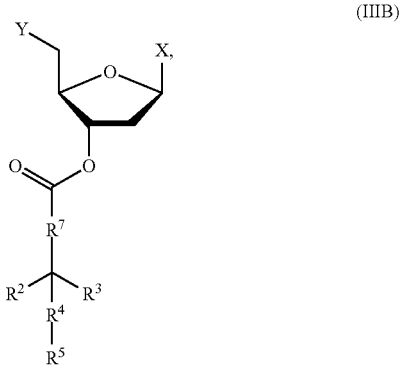

(IIIB)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

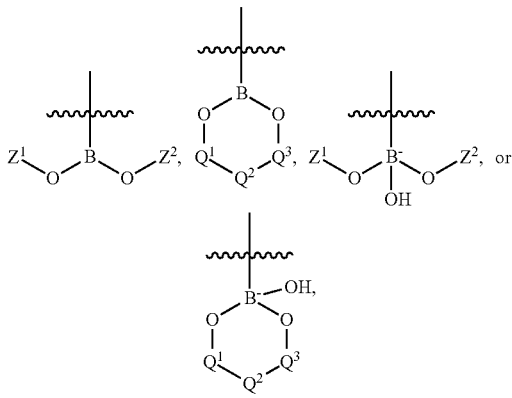

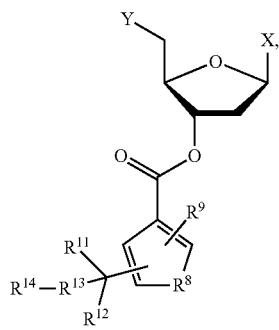

(IIIC)

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^7$ is O or $NR^a$;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

n is 0 or an integer ranging from 1 to 3; and p and q are each independently zero or an integer ranging from 1 to 3.

In some embodiments, at least one of $R^2$ or $R^3$ is H. In other embodiments, $R^2$ and $R^3$ are both H. In yet other embodiments, one of $R^2$ or $R^3$ is —[C($R^a$)($R^b$))$_p$—O]$_q$ ($R^a$) or —C(O)—O$R^a$—, and $R^a$ is methyl or ethyl. In some embodiments, $R^2$ selected from methyl, ethyl, isopropyl, or tertbutyl, and $R^3$ is H. In yet further embodiments, at least one of $R^2$ or $R^3$ is H, $R^5$ is —B(O$Z^1$)(O$Z^2$), and one of $Z^1$ or $Z^2$ is H. In even further embodiments, both $R^2$ and $R^3$ are H, $R^5$ is —B(O$Z^1$)(O$Z^2$), and one of $Z^1$ or $Z^2$ is H. In yet even further embodiments, both $R^2$ and $R^3$ are H, $R^5$ is —B(O$Z^1$)(O$Z^2$), and both of $Z^1$ and $Z^2$ are H.

In some embodiments, $R^7$ is O. In other embodiments, $R^7$ is O, $R^5$ is —B(O$Z^1$)(O$Z^2$), and $Z^1$ and $Z^2$ are independently selected from H, methyl, ethyl, isopropyl, or tertbutyl. In yet other embodiments, $R^7$ is O, and $R^5$ is —B(OH)$_2$. In yet other embodiments, $R^7$ is O, $R^4$ is phenyl or a substituted phenyl (e.g. one substituted with a methyl group, an ethyl group, an isopropyl group, or a tertbutyl group), and $R^5$ is —B(OH)$_2$. In further embodiments, $R^7$ is O, $R^4$ is a substituted or unsubstituted 5- or 6-membered heterocycloalkyl group (e.g. one substituted with a methyl group, an ethyl group, an isopropyl group, or a tertbutyl group), and $R^5$ is —B(OH)$_2$.

In some embodiments, the nucleotides (including any salts thereof) of the present disclosure have a structure embodied by Formula (IIIC):

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^8$ is O, $NR^e$, or S;

$R^9$ is H, halogen, a $C_1$-$C_4$ alkyl group, —C(O)—$R^a$, —N($R^a$)($R^b$), or —NO$_2$;

$R^{11}$ and $R^{12}$ are each independently H or a linear or branched $C_1$-$C_4$ alkyl group;

$R^{13}$ is a bond, —CH$_2$— or —CH$_2$—CH$_2$—;

$R^{14}$ is —N$_3$, —(C($R^a$)($R^b$))$_n$—N$^+$C$^-$, —(C($R^a$)($R^b$))$_n$—CN, or —B(O$Z^1$)(O$Z^2$), where $Z^1$ and $Z^2$ are independently selected from H, methyl, ethyl, isopropyl, or tertbutyl;

$R^a$ and $R^b$ are each independently H or a saturated $C_1$-$C_6$ alkyl group;

$R^e$ is H or a $C_1$-$C_4$ alkyl group; and n is 0 or an integer ranging from 1 to 3.

In some embodiments, the heterocyclic ring is substituted at the 2,3 position or the 2,5 position, e.g. the —C($R^{11}$)($R^{12}$)—$R^{13}$-$R^{14}$ is present at the 3 position or the 5 position of the heterocyclic ring.

In some embodiments, at least one of $R^{11}$ or $R^{12}$ is H. In other embodiments, $R^{11}$ is selected from methyl, ethyl, isopropyl, or tertbutyl, and $R^{12}$ is H. In yet other embodiments, at least one of $R^{11}$ or $R^{12}$ is H, $R^{14}$ is —B(O$Z^1$)(O$Z^2$), and one of $Z^1$ or $Z^2$ is H. In further embodiments, both $R^{11}$ and $R^{12}$ are H, $R^{14}$ is —B(O$Z^1$)(O$Z^2$), $Z^1$ is H, and $Z^2$ is a $C_1$-$C_4$ alkyl group. In further embodiments, $R^9$ is H, one of $R^{11}$ or $R^{12}$ is H, $R^{14}$ is —B(O$Z^1$)(O$Z^2$), $Z^1$ is H, and $Z^2$ is a $C_1$-$C_4$ alkyl group. In even further embodiments, both $R^{11}$ and $R^{12}$ are H and $R^{14}$ is —B(OH)$_2$.

In some embodiments, at least one of $R^{11}$ or $R^{12}$ is H, and $R^{14}$ is $N_3$. In other embodiments, $R^{11}$ and $R^{12}$ are both H, and $R^{14}$ is $N_3$. In some embodiments, $R^{14}$ is $N_3$. In some embodiments, $R^{13}$ is a bond and $R^{14}$ is $N_3$. In some embodiments, $R^{13}$ is a bond, $R^{14}$ is $N_3$, and $R^9$ is H. In some embodiments, $R^{13}$ is a bond, $R^{14}$ is $N_3$, and $R^1$ is O. In other embodiments, $R^{13}$ is a bond, $R^{14}$ is $N_3$, and $R^8$ is $NR^e$. In yet other embodiments, $R^{13}$ is a bond, $R^{14}$ is $N_3$, and $R^8$ is S.

In some embodiments, the nucleotides (including any salts thereof) of the present disclosure have a structure embodied by Formula (IIID):

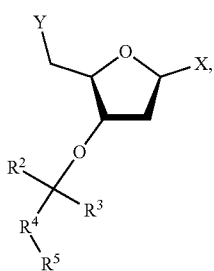

(IIID)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted phenyl group, —CH=CH—, a substituted unsubstituted 5- or 6-membered heterocycloalkyl group, or —O—C(O)-aryl-; and $R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

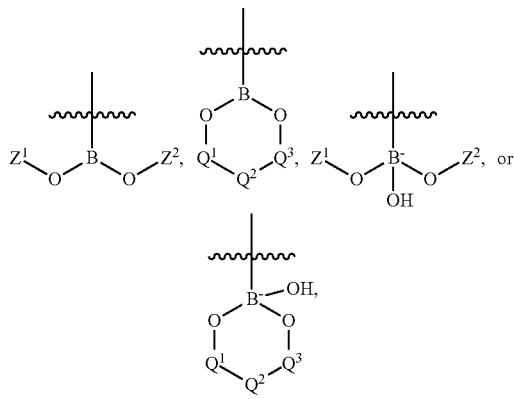

where $Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

n is 0 or an integer ranging from 1 to 3; and p and q are each independently zero or an integer ranging from 1 to 3;

with the proviso that when $R^2$ and $R^3$ are H and $R^4$ is a bond, then $R^5$ is not an azide.

In some embodiments, $R^4$ is a bond. In other embodiments, $R^4$ is a bond and $R^5$ is —B(OH)$_2$. In yet other embodiments, $R^4$ is a bond, $R^5$ is —(C($R^a$)($R^b$))$_n$—N$_3$, and at least one of $R^2$ or $R^3$ is methyl, ethyl, isopropyl, or tertbutyl.

In some embodiments, $R^4$ is a phenyl group, $R^5$ is —B(OZ$^1$)(OZ$^2$), and one of $Z^1$ or $Z^2$ is H. In other embodiments, $R^4$ is a phenyl group and $R^5$ is a —B(OH)$_2$. In other embodiments, $R^4$ is a substituted phenyl group and $R^5$ is a —B(OH)$_2$, wherein the phenyl group is substituted with at least one $C_1$ to $C_4$ alkyl group. In yet other embodiments, $R^4$ is a substituted phenyl group and $R^5$ is a —B(OH)$_2$, wherein the phenyl group is substituted with a single substituent selected from a methyl group, an ethyl group, an isopropyl group, or a tertbutyl group.

In some embodiments, $R^4$ is —CH=CH—, $R^5$ is —B(OZ$^1$)(OZ$^2$), and one of $Z^1$ or $Z^2$ is H, methyl, or ethyl. In other embodiments, $R^4$ is —CH=CH—, $R^5$ is —B(OZ$^1$)(OZ$^2$), and one of $Z^1$ or $Z^2$ is H, methyl, or ethyl. In other embodiments, $R^4$ is —CH=CH—, $R^5$ is —B(OZ$^1$)(OZ$^2$), and one of $Z^1$ or $Z^2$ is H. In yet other embodiments, at least one $R^2$ or $R^3$ is H, $R^4$ is —CH=CH—, $R^5$ is —B(OZ$^1$)(OZ$^2$), and one of $Z^1$ or $Z^2$ is H. In yet other embodiments, at least one $R^2$ or $R^3$ is H, $R^4$ is —CH=CH—, $R^5$ is —B(OZ$^1$)(OZ$^2$), and one of $Z^1$ or $Z^2$ is H, methyl, or ethyl. In further embodiments, at least one $R^2$ or $R^3$ is H, $R^4$ is —CH=CH—, and $R^5$ is a —B(OH)$_2$.

In some embodiments, the nucleotides (including any salts thereof) of the present disclosure have a structure as embodied by Formula (IV):

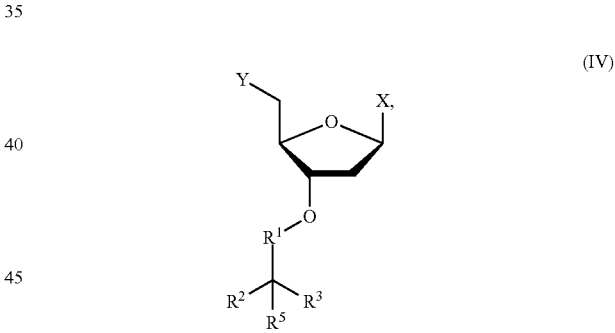

(IV)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

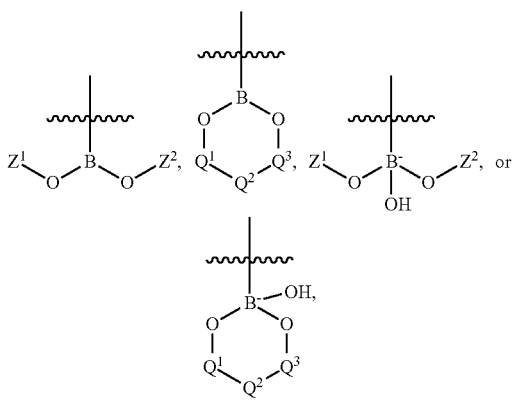

where
Z$^1$ and Z$^2$ are independently H, a C$_1$-C$_4$ alkyl group, or a 5- to 6-membered aryl group optionally substituted with one or more hydroxyl groups;

Q$^1$ and Q$^3$ are each independently a bond, —C(R$^e$)(R$^f$)—, or —C(O)—;

Q$^2$ is a bond, o-phenylene, or —[C(R$^e$)(R$^f$)]$_w$—, where w is 1 or 2;

R$^a$ and R$^b$ are each independently H or a saturated C$_1$-C$_6$ alkyl group;

R$^e$ and R$^f$ are independently H, methyl, ethyl, isopropyl, or a substituted or unsubstituted 5- or 6-membered aryl group;

R$^x$ is a substituted or unsubstituted 5- or 6-membered aromatic group or heteroaromatic group;

n is 0 or an integer ranging from 1 to 3; and p and q are each independently zero or an integer ranging from 1 to 3;

with the proviso that when R$^1$ is a bond and R$^2$ and R$^3$ are both H, R$^5$ is not an azide.

In some embodiments, R$^1$ is a bond. In other embodiments, at least one of R$^2$ or R$^3$ is H. In yet other embodiments, R$^1$ is a bond, and at least one of R$^2$ or R$^3$ is H. In further embodiments, R$^1$ is a bond, only one of R$^2$ or R$^3$ is H, and R$^5$ is —(C(R$^a$)(R$^b$))$_n$—N$_3$.

In some embodiments, one of R$^2$ or R$^3$ is selected from methyl, ethyl, isopropyl, or tertbutyl. In other embodiments, one of R$^2$ or R$^3$ is selected from methyl, ethyl, isopropyl, or tertbutyl, R$^5$ is —B(OZ$^1$)(OZ$^2$), and Z$^1$ and Z$^2$ are independently selected from H, methyl, ethyl, isopropyl, or tertbutyl. In some embodiments, R$^5$ is —B(OZ$^1$)(OZ$^2$), and Z$^1$ and Z$^2$ are independently selected from H, methyl, ethyl, isopropyl, or tertbutyl. In other embodiments, R$^5$ is —B(OZ$^1$)(OZ$^2$), and one of Z$^1$ or Z$^2$ is H. In yet other embodiments, R$^5$ is —B(OZ$^1$)(OZ$^2$), and both Z$^1$ and Z$^2$ are H. In yet even further embodiments, R$^5$ is —B(OZ$^1$)(OZ$^2$), both Z$^1$ and Z$^2$ are H, and at least one of R$^2$ or R$^3$ is H.

In some embodiments, R$^5$ is

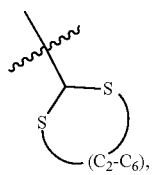

where C$_2$-C$_6$ represents a saturated 2 to 6 carbon alkyl chain which may be substituted or unsubstituted. In some embodiments, R$^5$ is

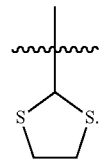

In other embodiments, R$^5$ is

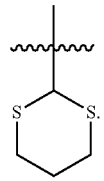

In yet other embodiments, at least one R$^2$ or R$^3$ is H and R$^5$ is

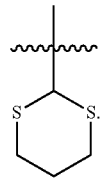

In yet other embodiments, R$^1$ is a bond, at least one R$^2$ or R$^3$ is H, and R$^5$ is

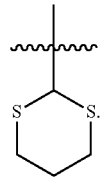

In some embodiments, R$^1$ is a —CH$_2$—, and R$^5$ is —B(OZ$^1$)(OZ$^2$). In some embodiments, R$^1$ is a —CH$_2$—, R$^4$ is a bond, and R$^5$ is —B(OZ$^1$)(OZ$^2$). In some embodiments, R$^1$ is a —CH$_2$—, R$^4$ is a bond, and R$^5$ is —B(OZ$^1$)(OZ$^2$), and at least one of R$^2$ or R$^3$ is H.

In some embodiments, the nucleotides (including any salts thereof) of the present disclosure have a structure as embodied by Formula (VA):

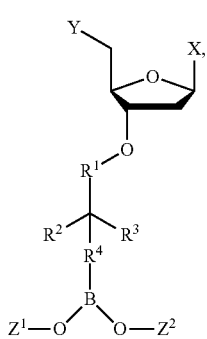

(VA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$ (R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$Z^1$ and $Z^2$ are independently H, a C$_1$-C$_4$ alkyl group, or a 5- to 6-membered aryl group optionally substituted with one or more hydroxyl groups;

$R^a$ and $R^b$ are each independently H or a saturated C$_1$-C$_6$ alkyl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3.

In some embodiments, $R^2$ and $R^3$ are independently selected from H, methyl, ethyl, isopropyl, and tertbutyl. In other embodiments, $R^1$ is a bond, and $R^2$ and $R^3$ are independently selected from H, methyl, ethyl, isopropyl, and tertbutyl. In yet other embodiments, $R^1$ is a bond, $R^2$ and $R^3$ are independently selected from H, methyl, ethyl, isopropyl, and tertbutyl, and $R^4$ is a bond.

In some embodiments, $R^1$ is —CH$_2$—, and $Z^1$ and $Z^2$ are independently selected from H, methyl, or ethyl. In some embodiments, $R^1$ is —CH$_2$—, $Z^1$ and $Z^2$ are independently selected from H, methyl, or ethyl, and $R^4$ is a bond.

Non-limiting examples of the nucleotides (including any salts thereof) of Formula (VA) include the following:

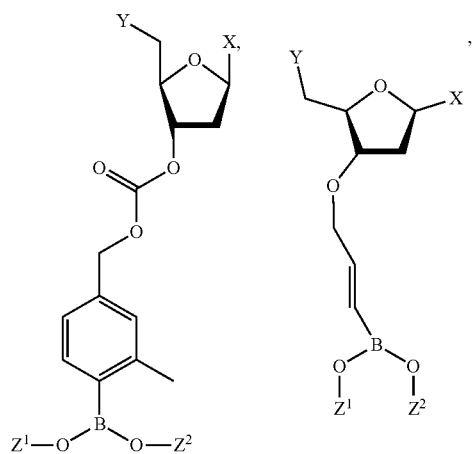

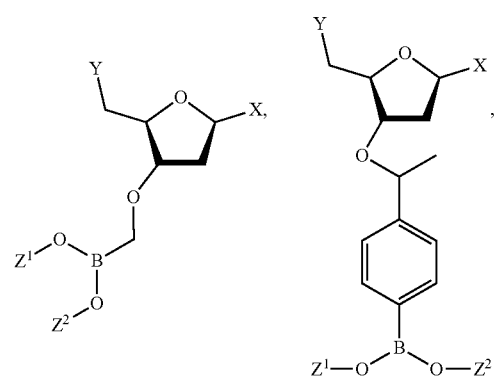

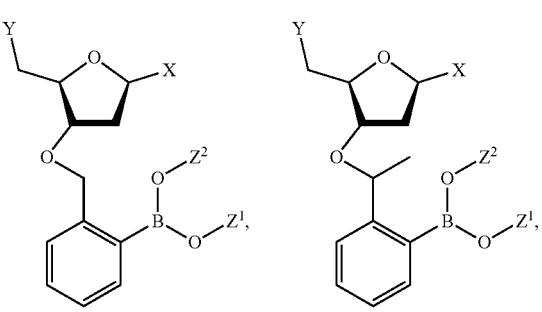

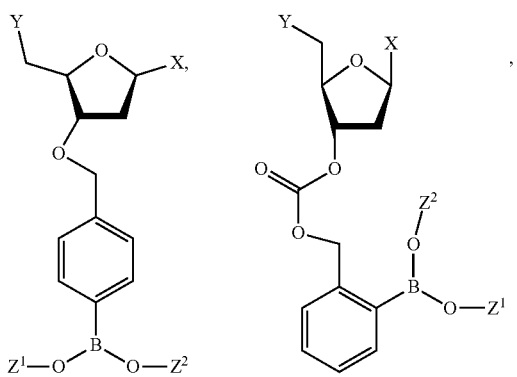

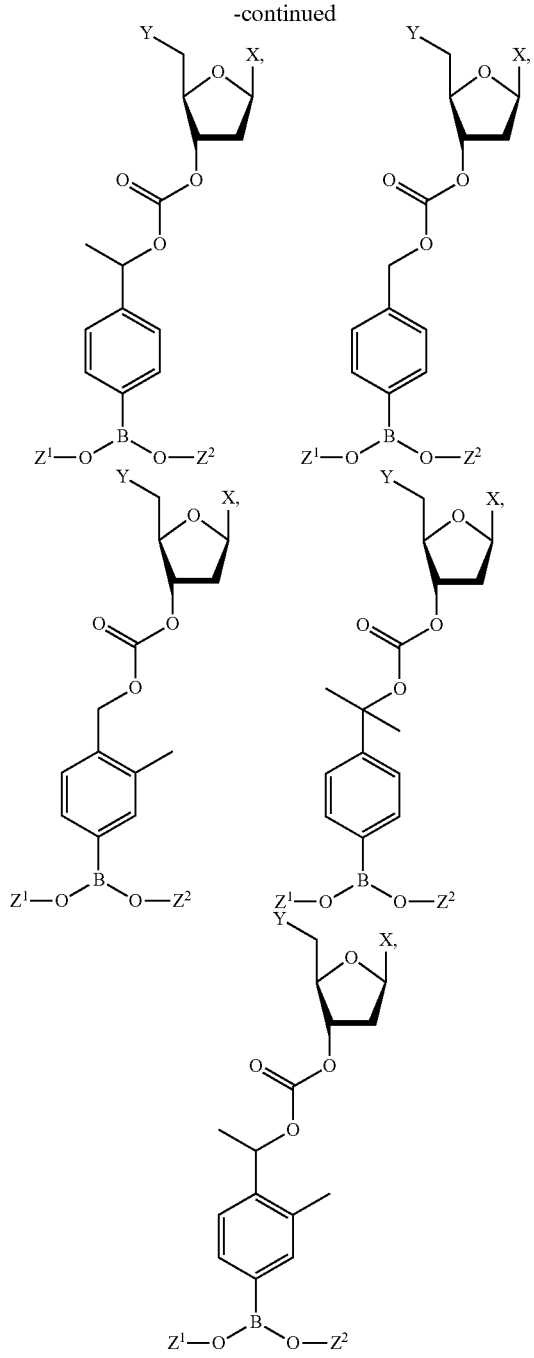
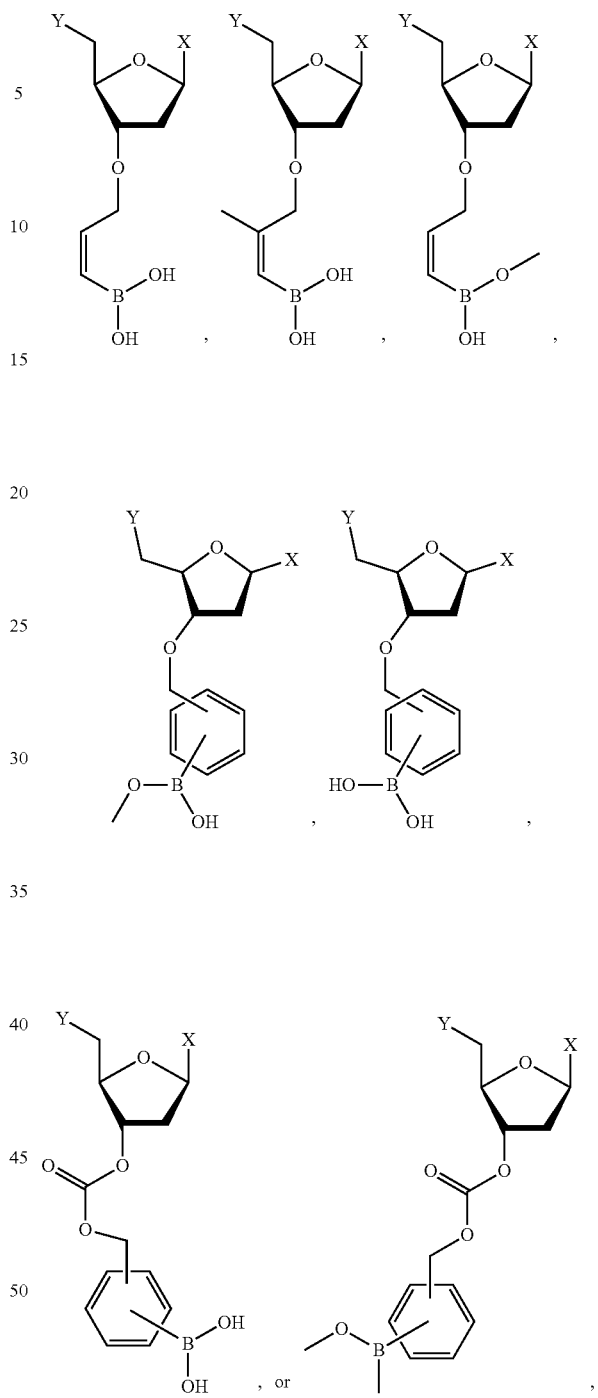

where

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5; and $Z^1$ and $Z^2$ are independently H, a $C_1$-$C_4$ alkyl group, or a 5- to 6-membered aryl group optionally substituted with one or more hydroxyl group.

In some embodiments, $Z^1$ and $Z^2$ are independently selected from H, methyl, or ethyl. In some embodiments, $Z^1$ and $Z^2$ are both H.

Additional non-limiting examples of the nucleotides (including any salts thereof) of Formula (VA) include the following:

where

X is a nucleobase or a tagged nucleobase; and

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5.

In some embodiments, the heterocyclic ring is substituted at the ortho and para positions with a —B(OH)$_2$ group.

In some embodiments, the nucleotides (including any salts thereof) of the present disclosure have a structure embodied by Formula (VB):

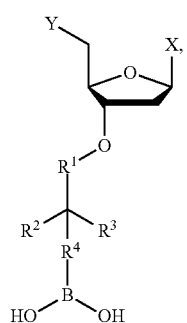

(VB)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$ (R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^4$ is a bond, a substituted or unsubstituted 5- or 6-membered aryl group, —CH=CH—, or a substituted or unsubstituted 5- or 6-membered heterocycloalkyl group;

$R^a$ and $R^b$ are each independently H or a saturated C$_1$-C$_6$ alkyl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3.

In some embodiments $R^1$ is —CH$_2$—. In some embodiments $R^1$ is —CH$_2$— and $R^4$ is a bond.

In some embodiments, $R^2$ and $R^3$ are independently selected from H, methyl, ethyl, isopropyl, and tertbutyl. In other embodiments, $R^1$ is a bond, and $R^2$ and $R^3$ are independently selected from H, methyl, ethyl, isopropyl, and tertbutyl. In yet other embodiments, $R^1$ is a bond, $R^2$ and $R^3$ are independently selected from H, methyl, ethyl, isopropyl, and tertbutyl, and $R^4$ is a bond.

In some embodiments, $R^1$ is a bond, $R^2$ and $R^3$ are independently selected from H, methyl, ethyl, isopropyl, and tertbutyl, and $R^4$ is a phenyl group having at least one substituent. In other embodiments, $R^1$ is a bond, $R^2$ and $R^3$ are independently selected from H, methyl, ethyl, isopropyl, and tertbutyl, and $R^4$ is a phenyl group having at least one substituent, wherein the at least one substituent is selected from methyl, ethyl, isopropyl, or tertbutyl. In yet other embodiments, $R^1$ is a bond, $R^2$ and $R^3$ are independently selected from H, methyl, ethyl, isopropyl, and tertbutyl, and $R^4$ is an unsubstituted phenyl group.

In some embodiments, the nucleotides (including any salts thereof) of the present disclosure have a structure embodied by Formula (VC):

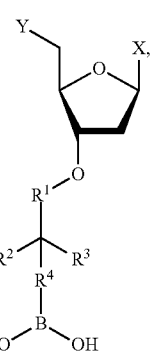

(VC)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$ (R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^a$ and $R^b$ are each independently H or a saturated C$_1$-C$_6$ alkyl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3.

In some embodiments, $R^1$ is a bond and at least one of $R^2$ or $R^3$ is H.

In some embodiments $R^1$ is —CH$_2$—. In some embodiments $R^1$ is —CH$_2$—, and at least one of $R^2$ or $R^3$ is H.

In some embodiments, the nucleotides (including any salts thereof) of the present disclosure have a structure as embodied by Formula (VD):

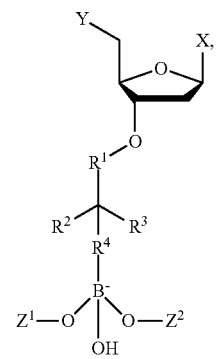

(VD)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted 5- to 7-membered aryl group, —CH═CH—, a substituted or unsubstituted 5- or 6-membered heterocycloalkyl group, or —O—C(O)-aryl-;

$Z^1$ and $Z^2$ are independently H, a $C_1$-$C_4$ alkyl group, or a 5- to 6-membered aryl group optionally substituted with one or more hydroxyl groups;

$R^a$ and $R^b$ are each independently H or a saturated $C_1$-$C_6$ alkyl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3.

In some embodiments, $R^2$ and $R^3$ are independently selected from H, methyl, ethyl, isopropyl, and tertbutyl. In other embodiments, $R^1$ is a bond, and $R^2$ and $R^3$ are independently selected from H, methyl, ethyl, isopropyl, and tertbutyl. In yet other embodiments, $R^1$ is a bond, $R^2$ and $R^3$ are independently selected from H, methyl, ethyl, isopropyl, and tertbutyl, and $R^4$ is a bond.

In some embodiments, $R^1$ is —CH$_2$—, and $Z^1$ and $Z^2$ are independently selected from H, methyl, or ethyl. In some embodiments, $R^1$ is —CH$_2$—, $Z^1$ and $Z^2$ are independently selected from H, methyl, or ethyl, and $R^4$ is a bond.

In some embodiments, the nucleotides (including any salts thereof) of the present disclosure have a structure embodied by Formula (VIA):

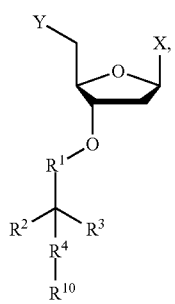

(VIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—N$R^a$—, —C(O)—$R^x$—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted phenyl group, —CH═CH—, or a substituted or unsubstituted 5- or 6-membered heterocycloalkyl group, or —O—C(O)-aryl-;

$R^{10}$ is —OH, —(C($R^a$)($R^b$))$_u$—OH, —(C($R^a$)($R^b$))$_u$—C(O)H, or a 5- to 8-membered cycloalkyl group comprising two —S(O)— groups positioned 1,3 relative to each other;

$R^a$ and $R^b$ are each independently H or a saturated $C_1$-$C_6$ alkyl group;

$R^x$ is a substituted or unsubstituted 5- or 6-membered aromatic group or heteroaromatic group;

n is 0 or an integer ranging from 1 to 3;

p and q are each independently zero or an integer ranging from 1 to 3; and u is an integer ranging from 1 to 3.

In some embodiments, the nucleotides (including any salts thereof) of the present disclosure have a structure embodied by any one of Formulas (VIB), (VIC), (VID), (VIE), and (VIF):

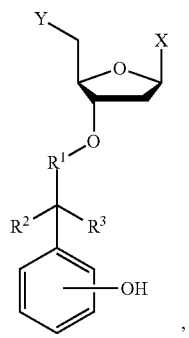

(VIB)

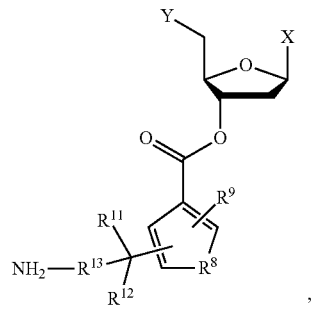

(VIC)

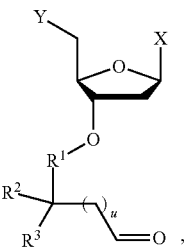

(VID)

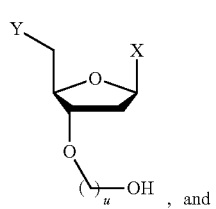

(VIE)

, and

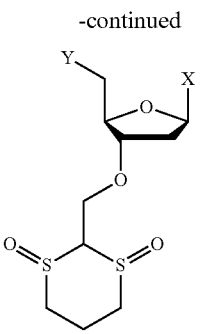

(VIF)

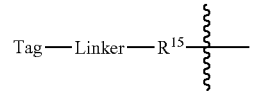

(VIIA)

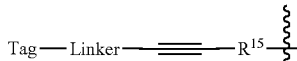

(VIIB)

, or

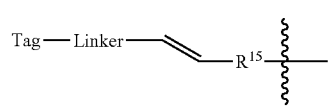

(VIIC)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, —C(O)—R$^x$—;

$R^2$ and $R^3$ are each independently H, a saturated or unsaturated C$_1$-C$_6$ alkyl group, a C$_5$-C$_6$ aryl or heteroaryl group, a halogen, —[(C(R$^a$)(R$^b$))$_p$—O]$_q$ (R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^8$ is O, NR$^e$, or S;

$R^9$ is H, halogen, a C$_1$-C$_4$ alkyl group, —C(O)—R$^a$, —N(R$^a$)(R$^b$), or —NO$_2$;

$R^{11}$ and $R^{12}$ are each independently H or a linear or branched C$_1$-C$_4$ alkyl group;

$R^{13}$ is a bond, —CH$_2$—, or —CH$_2$—CH$_2$—;

$R^a$ and $R^b$ are each independently H or a saturated C$_1$-C$_6$ alkyl group;

$R^e$ is H or a C$_1$-C$_4$ alkyl group;

$R^x$ is a substituted or unsubstituted 5- or 6-membered aromatic group or heteroaromatic group;

n is 0 or an integer ranging from 1 to 3;

p and q are each independently zero or an integer ranging from 1 to 3; and u is an integer ranging from 1 to 3.

In some embodiments, the heterocyclic ring is substituted at the ortho and para positions with a —B(OH)$_2$ group.

In some embodiments, the compounds of any one of Formulas (VIA) to (VIF) may be present as a mixture, such as a mixture including boric acid or another other byproduct. In some embodiments, the compounds of any one of Formulas (VIA) to (VIF) may be present as a mixture with a nucleotide of Formula (I) or Formula (II).

Nucleobases and Tagged Nucleobases

As described herein, the nucleotides or nucleosides of the present disclosure may include a nucleobase or a tagged nucleobase. By "nucleobase" it is meant any nitrogenous base suitable for inclusion within an oligonucleotide (e.g. an RNA or DNA molecule), including naturally occurring bases and synthetic bases. In some embodiments, the nucleobase is selected from adenine, cytosine, guanine, thymine, and uracil or a derivative or analog thereof. In other embodiments, the nucleobase is 7-deazaguanine, 7-deazaadenine or 5-methylcytosine.

In some embodiments, a tagged nucleobase has a structure as embodied by any of Formulas (VIIA), (VIIB), (VIIC):

wherein $R^{15}$ is a nucleobase;

'Linker is a straight chain or branched, substituted or unsubstituted, saturated or unsaturated, aliphatic or aromatic group having between 1 and 50 carbon atoms and optionally substituted with one or more heteroatoms; and 'Tag' includes a detectable species.

Methods of attaching tags to the nucleotides of the present are disclosed in United States Patent Application Publication No. 2014/0134616, the disclosure of which is incorporated by reference herein in its entirety.

In some embodiments, the 'Linker' can be attached at any position on the nucleobase provided that Watson-Crick base pairing can still be carried out. In some embodiments, and in the context of purine bases, the Linker is attached via 7-position of a 7-deazapurine, via an 8-modified purine, via an N-6 modified adenine, or an N-2 modified guanine. In some embodiments, and in the context of pyrimidines, the attachment is via the 5 position on cytosine, thymine or uracil and the N-4 position on cytosine.

In some embodiments, the 'Linker' includes from between 1 and 50 carbon atoms. In other embodiments, the 'Linker" includes from between 2 and 25 carbon atoms. In yet other embodiments, the 'Linker" includes from between 5 and 20 carbon atoms. In further embodiments, the 'Linker" includes from between 10 and 20 carbon atoms. In some embodiments, the 'Linker' has a molecular weight ranging from about 20 g/mol to about 600 g/mol. In other embodiments, the 'Linker' has a molecular weight ranging from about 40 g/mol to about 500 g/mol. In other embodiments, the 'Linker' has a molecular weight ranging from about 50 g/mol to about 500 g/mol. In some embodiments, the 'Linker' has a length ranging from between about 0.5 nm to about 80 nm. In some embodiments, the 'Linker' has a length ranging from between about 0.5 nm to about 50 nm.

In some embodiments, the 'Linker' comprises a group which is capable of being cleaved, e.g. a photocleavable group, an enzymatically cleavage group, a chemically cleavable group, a group cleavable at certain pHs. The use of the term "cleavable linker" is not meant to imply that the whole linker is required to be removed from the nucleobase. Rather, a cleavage site within the linker can be located at a position on the linker that ensures that part of the linker remains attached to the nucleobase after cleavage. The use of a cleavable linker ensures that the tag can, if required, be removed after detection, avoiding any interfering signal with any tagged nucleotide incorporated subsequently. Cleavable linkers are known in the art, and conventional chemistry can be applied to attach a linker to a nucleobase and a tag. The linker can be cleaved by any suitable method, including exposure to acids, bases, nucleophiles, electrophiles, radicals, metals, reducing or oxidizing agents, light, temperature, enzymes, etc. Suitable linkers can be adapted from standard chemical blocking groups, as disclosed in Greene & Wuts, Protective Groups in Organic Synthesis, John Wiley & Sons. Further suitable cleavable linkers used in solid-phase synthesis are disclosed in Guillier et al. (Chem. Rev. 100:2092-2157, 2000), the disclosure of which is hereby incorporated by reference herein in its entirety.

In some embodiments, it is believed that the linker may optionally comprise one or more spacer units. The spacer distances the nucleobase from the cleavage site, tag, or linker. The length of the linker is unimportant provided that the tag is held a sufficient distance from the nucleotide so as not to interfere with any interaction between the nucleotide and an enzyme, e.g. polymerase. In some embodiments, a tagged nucleobase comprises the structure -[Nucleobase]-[Linker]-[Extender]$_y$-[Tag], where the 'Extender' is a straight chain or branched, substituted or unsubstituted, saturated or unsaturated, aliphatic or aromatic group having between 1 and 60 carbon atoms and optionally substituted with one or more heteroatoms; and y is 0, 1, or 2.

Suitable linkers include, but are not limited to, disulfide linkers, acid labile linkers, including dialkoxybenzyl linkers, Sieber linkers, indole linkers, t-butyl Sieber linkers, electrophilically cleavable linkers, nucleophilically cleavable linkers, photocleavable linkers, cleavage under reductive conditions, oxidative conditions, cleavage via use of safety-catch linkers, and cleavage by elimination mechanisms.

Photocleavable linkers have been used widely in carbohydrate chemistry. In some embodiments, the light required to activate cleavage does not affect the other components of the modified nucleotides. For example, if a fluorophore is used as the tag, in some embodiments the fluorophore is chosen so that it absorbs light of a different wavelength to that required to cleave the linker molecule. Suitable linkers include those based on o-nitrobenzyl compounds and nitroveratryl compounds (by way of example, a 5-hydroxy-2-nitrobenzyl alcohol may be used as a starting material). In an embodiment, the photocleavable linker is a 2-nitrobenzyl moiety. Linkers based on benzoin chemistry can also be used (Lee et al., J. Org. Chem. 64:3454-3460, 1999).

For example, a group may be introduced into the linker that may be cleaved upon exposure to an electromagnetic radiation source having a wavelength of between about 200 nm to about 400 nm (UV) or between about 400 nm to about 800 nm (visible). In some embodiments, the UV or visible light photocleavable group is selected from the group consisting of Arylcarbonylmethyl Groups (including 4-acetyl-2-nitrobenzyl, Dimethylphenacyl (DMP), 2-(Alkoxymethyl)-5-methyl-α-chloroacetophenones, 2,5-Dimethylbenzoyl Oxiranes, and Benzoin groups: 3',5'-dimethoxybenzoin (DMB)), o-Nitrobenzyl Groups (including 1-(2-nitrophenyl)ethyl (NPE), 1-(Methoxymethyl)-2-nitrobenzene, 4,5-dimethoxy-2-nitrobenzyl (DMNB); α-carboxynitrobenzyl (α-CNB), o-Nitro-2-phenethyloxycarbonyl Groups, including 1-(2-nitrophenyl)ethyloxycarbonyl and 2-Nitro-2-Phenethyl Derivatives, and o-Nitroanilides such as Acylated 5-Bromo-7-Nitroindolines); Coumarin-4-yl-methyl Groups (including 7-Methoxycoumarin Derivatives); 9-substituted xanthenes, and Arylmethyl Groups (including o-Hydroxyarylmethyl Groups).

In some embodiments, a group may be introduced into the linker that may be cleaved upon exposure to an electromagnetic radiation source having a wavelength of between about 700 nm to about 1000 nm. Suitable near-infrared photocleavable groups include cyanine groups, including C4-dialkylamine-substituted heptamethine cyanines.

In yet other embodiments, the 'Linker' includes chemically cleavable groups that may be cleaved by different chemical reactants, including reducing agents or by induced changes in pH (e.g. cleavage of the group at a pH of less than about 7). Suitable chemically cleavable groups include disulfide-based groups; diazobenzene groups (including 2-(2-alkoxy-4-hydroxy-phenylazo) benzoic acid scaffolds, sensitive to sodium dithionite); ester bond-based groups (high pH); and acidic sensitive linkers (such as dialkoxydiphenylsilane linker or acylhydrazone). A vicinal diol cleavable linker may be cleaved by $NaIO_4$, such as described in "A simple and effective cleavable linker for chemical proteomics applications," Mol Cell Proteomics, 2013 January; 12(1):237-44. doi: 10.1074/mcp.M112.021014. Epub 2012 Oct. 1. Suitable enzymatically cleavable groups include trypsin cleavable groups and V8 protease cleavable groups. Further linkers which may be utilized in any of the nucleotides of the present disclosure are disclosed in United States Patent Application Publication No. 2018/0057870, the disclosure of which is hereby incorporated by reference herein in its entirety.

Electrophilically cleaved linkers are believed to be cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system. The use of thiophilic metals, such as nickel, silver or mercury, in the cleavage of thioacetal or other sulfur-containing protecting groups can also be considered for the preparation of suitable linker molecules.

Nucleophilic cleavage is also a well-recognized method in the preparation of linker molecules. Groups such as esters that are labile in water (i.e., can, be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

There are many linkers known that are susceptible to reductive cleavage. Catalytic hydrogenation using palladium-based catalysts has been used to cleave benzyl and benzyloxycarbonyl groups. Disulfide bond reduction is also known in the art.

Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the disclosure. In some embodiments, the linker comprises a group —$CH_2$—O—$CH[B(OH)_2]$—$CH_2$— linker. In some embodiments, the linkers comprise 1,2-diol (—CH(OH)—CH(OH)—) based linkers.

Safety-catch linkers are those that cleave in two steps. In some embodiments, the first step is the generation of a reactive nucleophilic center followed by a second step involving an intra-molecular cyclization that results in cleavage. For example, levulinic ester linkages can be treated with hydrazine or photochemistry to release an active amine, which can then be cyclized to cleave an ester elsewhere in the molecule (Burgess et al., J. Org. Chem. 62:5165-5168, 1997).

Elimination reactions can also be used. For example, the base-catalyzed elimination of groups such as Fmoc and cyanoethyl, and palladium-catalyzed reductive elimination of allylic systems, can be used.

A tag may be any chemical group or molecule that is capable of being detected. In some embodiments, the tag may be any chemical group or molecule that is capable of being detected in a nanopore, e.g. by its charge, shape, size, or any combination, therefore. In some embodiments, a tag comprises one or more of ethylene glycol or a polymer derived from ethylene glycol, an amino acid, a carbohydrate, a peptide, a dye (including fluorophores), a chemiluminescent compound, a mass tag, a mononucleotide, a dinucleotide, a trinucleotide, a tetranucleotide, a pentanucleotide, a hexanucleotide, an oligonucleotide, a modified oligonucleotide, an aliphatic acid, an aromatic acid, an alcohol, a thiol group, a cyano group, a nitro group, an alkyl group, an alkenyl group, an alkynyl group, an azido group, or a combination thereof. Other tags are disclosed by Fuller et. al., "Real-time single-molecule electronic DNA sequencing by synthesis using polymer-tagged nucleotides on a nanopore array," PNAS May 10, 2016 113 (19) 5233-5238, the disclosure of which is incorporated by reference herein in its entirety. In some embodiments, the tag further comprises appropriate number of lysines or arginines to balance the number of phosphate groups in the compound. Examples of other suitable tags include the labels described in PCT Publication Nos. WO/1991/006678, WO/2018/191389, and WO/2004/018497, the disclosure of which are hereby incorporated by reference herein in their entireties.

In some embodiments, the tag is a mass tag which includes one or more reporter groups distinguishable by mass and thus capable of being analyzed by mass spectrometry. The reporter groups may be chemically different and thus distinguished from one another by molecular weight. Alternatively, the reporter groups may be chemically identical, but distinguished from one another by containing different isotopes (e.g. $^{12}C/^{13}C$ and $^{1}H/^{2}H$). The tag moiety is, and/or the reporter groups are, suitable or adapted for analysis by mass spectrometry e.g. after cleavage by photochemical or other suitable means. Examples of suitable mass tags include those recited in U.S. Pat. Nos. 7,132,519, 9,291,597 and 10,078,083, the disclosures of which are hereby incorporated by reference herein in their entireties. Additional examples of suitable mass tags include electrophore labels, such as those disclosed by Xu L et. al., "Electrophore Mass Tag Dideoxy DNA Sequence," Anal. Chem. 1997, Sep. 1; 69(17):3595-602, the disclosure of which is hereby incorporated by reference herein in its entirety.

In some embodiments, the tag is a polymer. In some embodiments, the tag is a polyethylene glycol (PEG) polymer. In embodiments where the polymer is PEG, a PEG polymer may be selected having any number of ethylene glycol units. For example, the number of ethylene glycol units in the PEG polymer may range from between 1 and 100. In some cases, the number of ethylene glycol units in the PEG polymer is different for each type of nucleotide. For example, for four different types of nucleotides, each may comprise a different tag having either 16, 20, 24 or 36 ethylene glycol units in the PEG polymer. In some embodiments, the PEG-based polymer is linear. In other embodiments, the PEG-based polymer is branched, i.e. the PEG-based polymer comprises multiple PEG chains. In some cases, the tag further comprises an additional identifiable moiety, such as a coumarin-based dye, or a derivative or analog of a coumarin-based dye. In some cases, the polymer is charged. In some instances, the polymer is not charged, and the tag is detected in a high concentration of salt (e.g., 3-4 M). Additional examples of tags are described in U.S. Publication Nos. 2015/0368710, 2018/0073071, 2015/0111759, 2013/0264207, 2013/0244340, 2014/0134616 and 2018/0112257, the disclosures of which are hereby incorporated by reference herein in their entireties. In particular, U.S. Publication Nos. 2015/0368710 and 2015/0111759 noted above, describe the use of tagged nucleotides for nanopore SBS, and disclose the possible use of a single nucleotide attached to a single tag comprising branched PEG chains. Other PEG-labeled nucleotides are disclosed by Shiv Kumar et. al., "PEG-Labeled Nucleotides and Nanopore Detection for Single Molecule DNA Sequencing by Synthesis," Scientific Reports 2, Article Number 684 (2012); and by Carl Fuller et. al., "Real-time single molecule electronic DNA sequencing by synthesis using polymer-tagged nucleotides on a nanopore array," Proc. Natl. Acad. Sci. USA 2016; May 10; 113(19):5233-5238.

In some embodiments, the tag is a fluorophore. Fluorophores belong to several common chemical classes including coumarins, fluoresceins (or fluorescein derivatives and analogs), rhodamines, oxazines (including resorufins), BODIPYs, luminophores and cyanines. Additional examples of fluorescent molecules can be found in Molecular Probes Handbook A Guide to Fluorescent Probes and Labeling Technologies, Molecular Probes, Eugene, Oreg., TheroFisher Scientific, 11th Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes) (Columbia Biosciences), and APC, APCXL, RPE, BPE (available from Phyco-Biotech, Greensea, Prozyme, Flogen).

In accordance with the foregoing, non-limiting examples of tagged nucleotides (including any salts thereof) of the present disclosure have a structure as embodied by any of Formulas (VIIIA), (VIIIB), or (VIIIC):

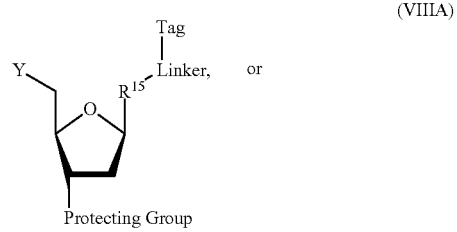

-continued (VIIIB)

(VIIIC)

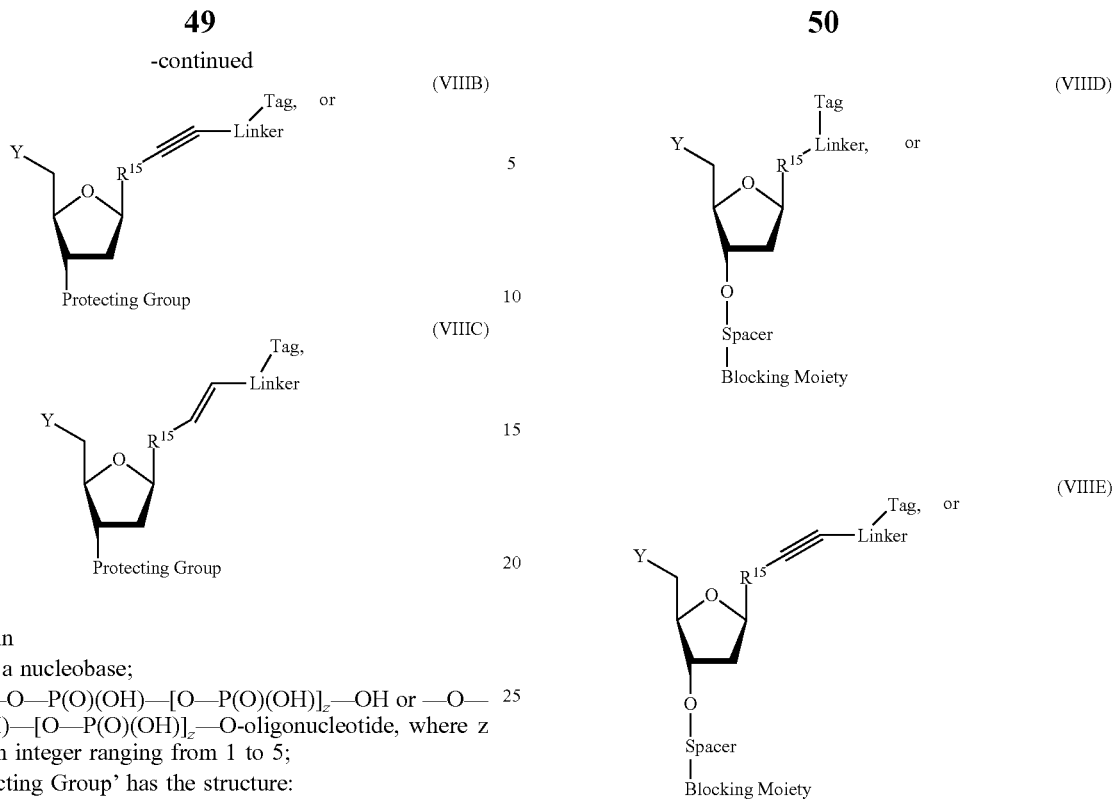

(VIIID)

(VIIIE)

wherein

R$^{15}$ is a nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

'Protecting Group' has the structure:

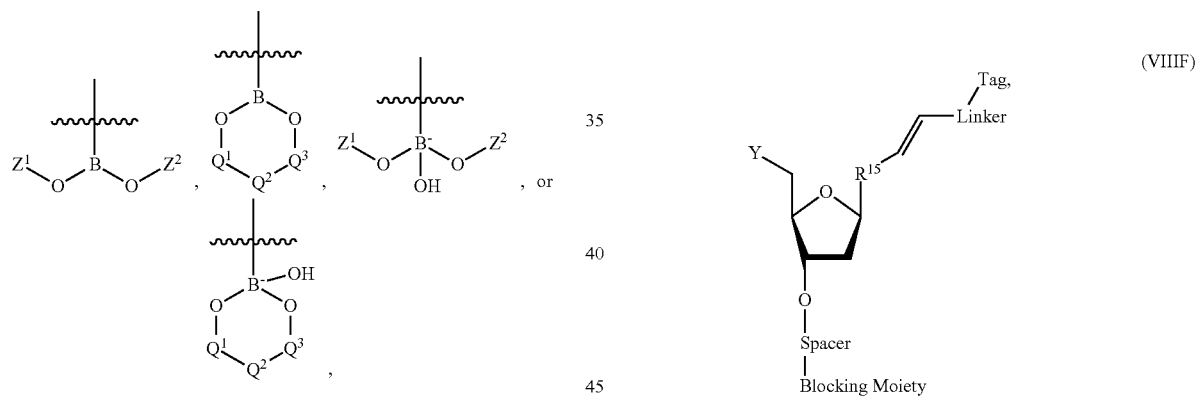

Z$^1$ and Z$^2$ are independently H, a C$_1$-C$_4$ alkyl group, or a 5- to 6-membered aryl group optionally substituted with one or more hydroxyl groups;

Q$^1$ and Q$^3$ are each independently a bond, —C(R$^e$)(R$^f$)—, or —C(O)—;

Q$^2$ is a bond, o-phenylene, or —[C(R$^e$)(R$^f$)]$_w$—, where w is 1 or 2;

R$^e$ and R$^f$ are independently H, methyl, ethyl, isopropyl, or a substituted or unsubstituted 5- or 6-membered aryl group;

'Linker is a straight chain or branched, substituted or unsubstituted, saturated or unsaturated, aliphatic or aromatic group having between 1 and 50 carbon atoms and optionally substituted with one or more heteroatoms; and 'Tag' is detectable species, including any of the species recited herein.

Other non-limiting examples of tagged nucleotides (including any salts thereof) of the present disclosure have a structure embodied by any one of Formulas (VIIID), (VIIIE), or (VIIIF):

(VIIIF)

wherein

R$^{15}$ is a nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

'Spacer' is a straight chain or branched, substituted or unsubstituted, saturated or unsaturated, aliphatic or aromatic group having between 1 and 16 carbon atoms and optionally substituted with one or more heteroatoms;

'Blocking Moiety' is a straight chain or branched, substituted or unsubstituted, saturated or unsaturated, aliphatic or aromatic group having between 1 and 20 carbon atoms, and optionally substituted with one or more heteroatoms, and provided that the 'Blocking Moiety' includes an azide group, an isonitrile, a cyano group, a 5- to 8-membered heterocycloalkyl group having two heteroatoms selected from O, N, S, or Se, a moiety derived from a substituted or unsubstituted 1,4-epoxy-1,4-dihydronaphthalene, or a group having the structure:

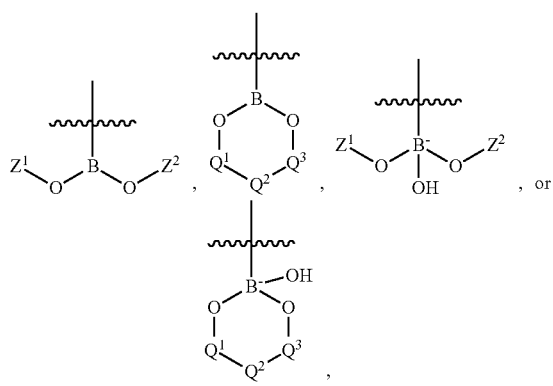

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^e$ and $R^f$ are independently H, methyl, ethyl, isopropyl, or a substituted or unsubstituted 5- or 6-membered aryl group;

'Linker is a straight chain or branched, substituted or unsubstituted, saturated or unsaturated, aliphatic or aromatic group having between 1 and 50 carbon atoms and optionally substituted with one or more heteroatoms; and 'Tag' is a detectable species, including any of the species recited herein;

provided that when the 'Blocking Moiety' is —$N_3$, the 'Spacer' is not —$CH_2$—.

Deprotection of Protected Nucleotides

The present disclosure also provides methods of deprotecting any of the protected nucleotides set forth herein. Following the incorporation of a protected nucleotide into a growing oligonucleotide as described herein, the protected nucleotide may be deprotected to yield a deprotected nucleotide. In embodiments where the nucleotide includes a tag or a label, and deprotection may occur before or after removal of the tag or label. In other embodiments, deprotection may occur simultaneously with the removal of the tag or label, if present.

Figure 5:
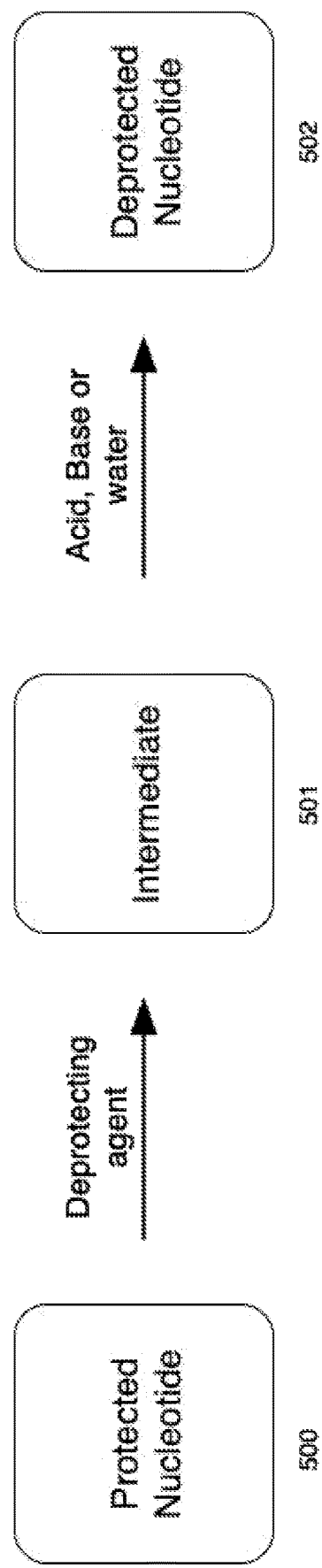
FIG. 5 illustrates a scheme for deprotecting a protected nucleotide to provide a deprotected nucleotide having a free 3' —OH group.

With reference to FIG. 5, protected nucleotides 500 according to the present disclosure may be treated with a deprotecting agent to provide an intermediate 501. In some embodiments, deprotection is carried out using a non-reductive reagent. In other embodiments, deprotection is carried out using an oxidant. In yet other embodiments, deprotection is carried out using a redox neutral reagent. Examples of suitable reagents include, without limitation, hydrogen peroxide, sodium periodate, sodium perchlorate, or peroxynitrate. Other examples of suitable reagents include, without limitation, a tetrazine or a derivative thereof, or esterase. Yet further examples of suitable reagents include (tris(2-carboxyethyl)phosphine) and dithiothreitol.

In some embodiments, the intermediate 501 undergoes a spontaneous elimination or hydrolysis to provide the deprotected nucleotide 502. For example, the intermediate may undergo a 1,6-elimination or a beta elimination depending on the configuration of the intermediate 501 and the conditions upon which the intermediate 501 is present. In some embodiments, the intermediate 501 may then be optionally treated with a base to provide the deprotected nucleotide 502. In some embodiments, suitable bases include, but are not limited to, piperidine, 1,8-Diazabicyclo[5.4.0]undec-7-ene (DBU), ammonia, diisopropylethylamine, and sodium hydroxide.

Scheme 1 below further illustrates the processes of deprotecting a protected nucleotide 100 (such as a protected nucleotide having Formula (IIIA)) in the presence of a deprotecting agent, e.g. hydrogen peroxide, sodium periodate, sodium perchlorate, or $NaONO_2$, to provide an intermediate 200 (such as an intermediate having Formula (VIA)), which may then undergo spontaneous elimination or hydrolysis to provide the deprotected nucleotide 300. As described herein, each of nucleotides 100, 200, or 300 may be incorporated into an oligonucleotide and may include a tag or label. Yet further illustrative deprotection strategies are illustrated in Schemes 2-9 set forth below.

Scheme 1: Illustrates the deprotection of a protected nucleotide, where $R^1, R^2, R^3, R^4, R^5, R^{10}$, Y, and X are as described herein.

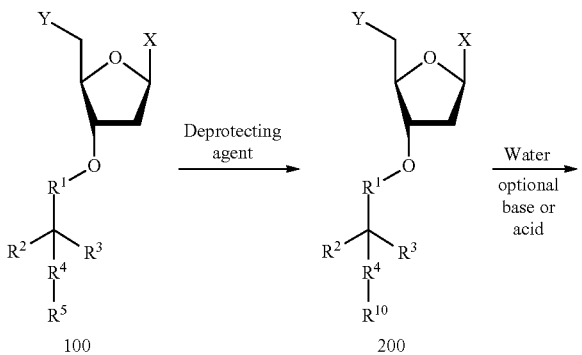

Scheme 2: Illustrates the deprotection of a protected nucleotide including a boronate moiety in accordance with some embodiments of the present disclosure, where Y and X are as described herein.

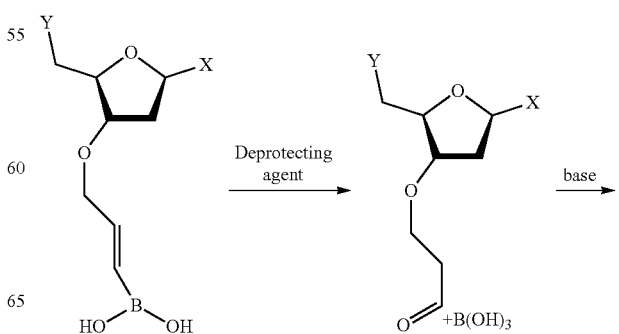

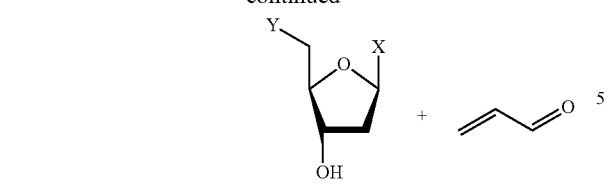

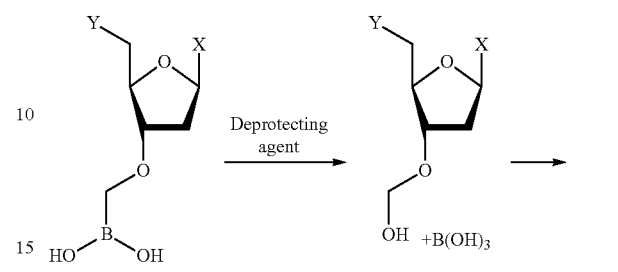

Scheme 4: Illustrates the deprotection of a protected nucleotide including a boronate moiety in accordance with some embodiments of the present disclosure where Y and X are as described herein.

Scheme 3: Illustrates the deprotection of a protected nucleotide including a boronate moiety in accordance with some embodiments of the present disclosure where Y and X are as described herein.

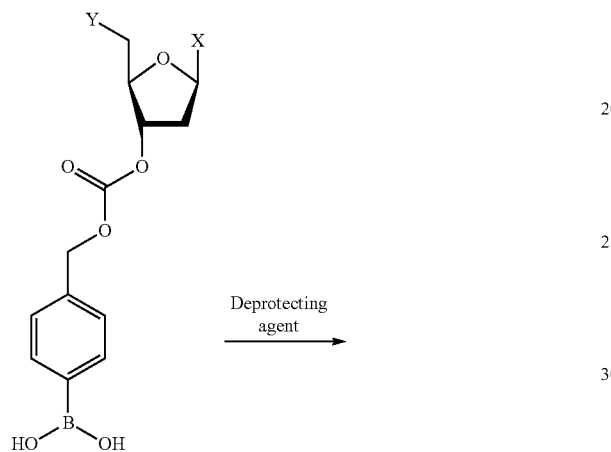

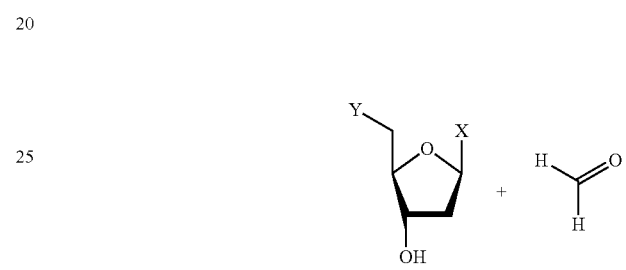

Scheme 5: Illustrates the deprotection of a protected nucleotide including a boronate moiety in accordance with some embodiments of the present disclosure where Y and X are as described herein.

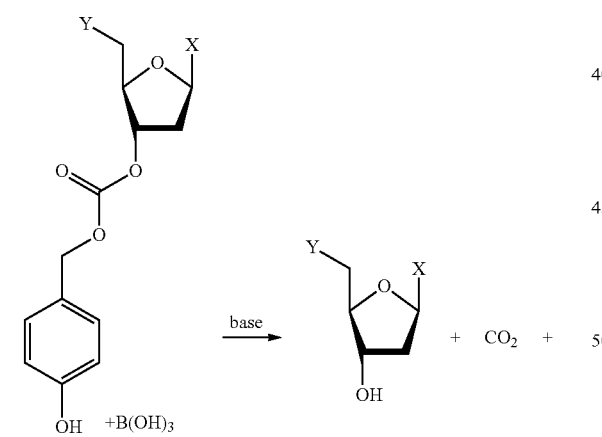

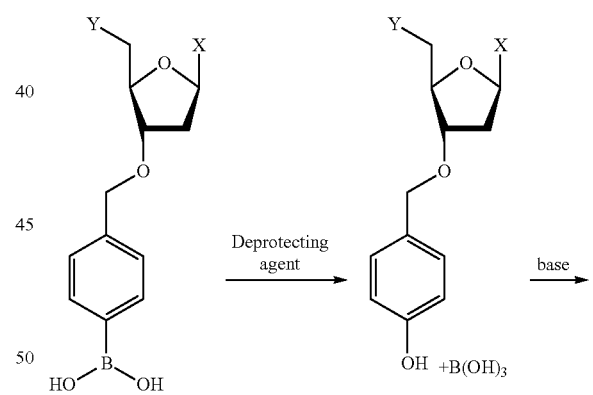

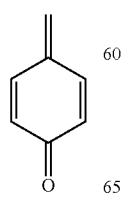

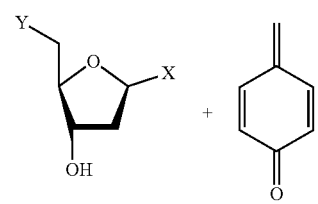

Scheme 6: Illustrates the deprotection of a protected nucleotide including a 1,3-dithiane group moiety in accordance with some embodiments of the present disclosure where Y and X are as described herein.

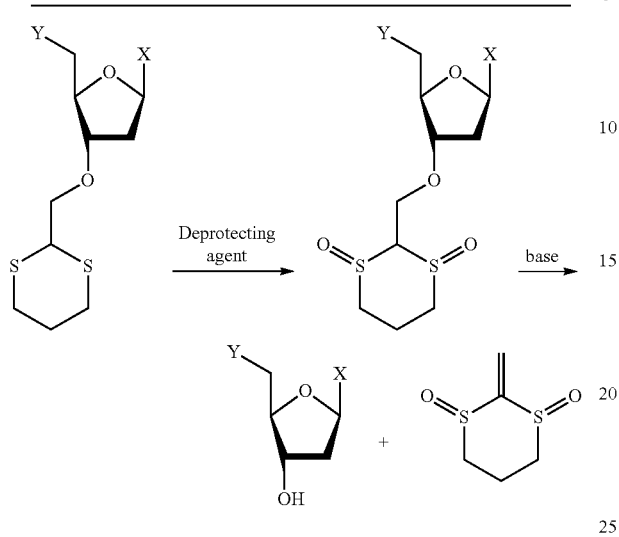

Scheme 8: Illustrates the deprotection of a protected nucleotide including an isonitrile moiety in accordance with some embodiments of the present disclosure where Y and X are as described herein.

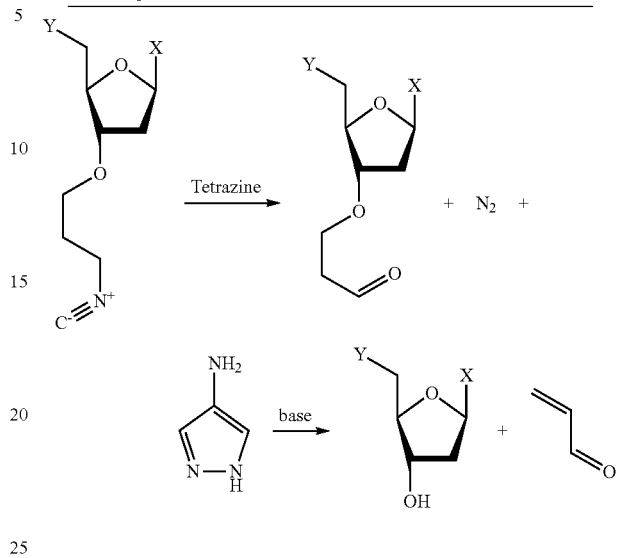

Scheme 7: Illustrates the deprotection of a protected nucleotide including an azide moiety in accordance with some embodiments of the present disclosure where Y and X are as described herein.

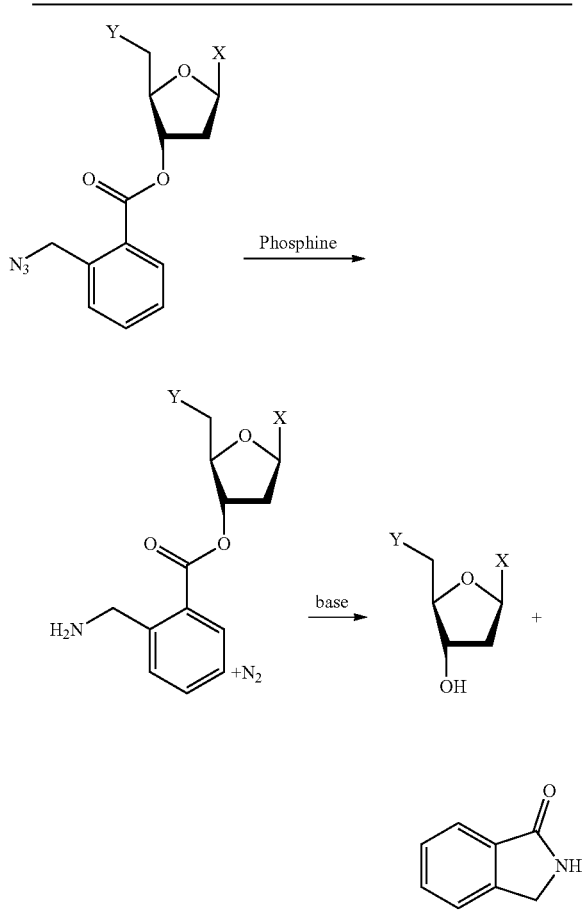

Scheme 9: Illustrates the deprotection of a protected nucleotide including a malonate moiety in accordance with some embodiments of the present disclosure.

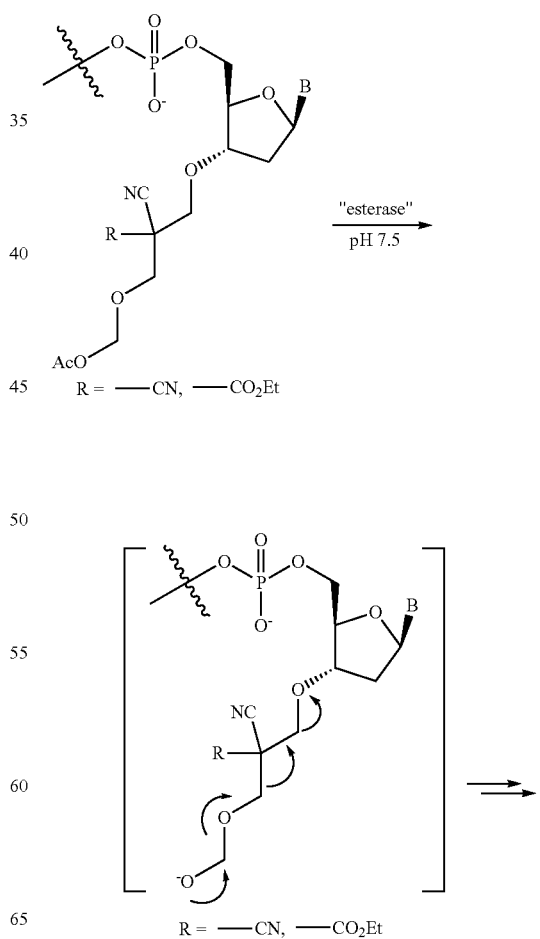

-continued

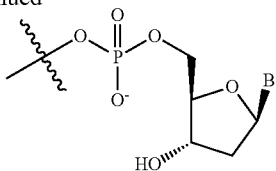

Nanopore Sequencing

The present disclosure also provides for methods of nanopore sequencing, whereby the method utilizes any of the nucleotides or tagged nucleotides described herein, including any of the nucleotides (or salts thereof) of Formulas (I), (II), (IIIA), (IIIB), (IIIC), (IIID), (IV), (VA), (VB), (VC), (VD), (VIIIA), (VIIIB), (VIIIC), (VIIID), (VIIIE), and (VIIIF).

Overview

Nanopore sequencing of a polynucleotide, e.g. DNA or RNA, may be achieved by strand sequencing and/or exosequencing of the polynucleotide sequence. In some embodiments, strand sequencing comprises methods whereby nucleotide bases of a sample polynucleotide strand are determined directly as the nucleotides of the polynucleotide template are threaded through the nanopore. In some embodiments, nanopore-based nucleotide acid sequencing uses a mixture of four nucleotide analogs that can be incorporated by an enzyme into a growing strand. In some embodiments, a polynucleotide can be sequenced by threading it through a microscopic pore in a membrane. In some embodiments, bases can be identified by the way they affect ions flowing through the pore from one side of the membrane to the other. In some embodiments, one protein molecule can "unzip" a DNA helix into two strands. A second protein can create a pore in the membrane and hold an "adapter" molecule. A flow of ions through the pore can create a current, whereby each base can block the flow of ions to a different degree, altering the current. The adapter molecule can keep bases in place long enough for them to be identified electronically (see PCT Publication No. WO/2018/034745, and United States Patent Application Publication Nos. 2018/0044725 and 2018/0201992, the disclosures of which are hereby incorporated by reference herein in their entireties).

In some embodiments, nanopores may be used to sequence nucleic acid molecules indirectly, i.e. indirect sequencing may include any method where a polymerized nucleic acid molecule does not pass through the nanopore during sequencing. In these embodiments, the nucleic acid molecule may be at least partially located in the vestibule of the nanopore, but not in the pore (i.e., narrowest portion) of the nanopore. The nucleic acid molecule may pass within any suitable distance from and/or proximity to the nanopore, and optionally within a distance such that byproducts released from nucleotide incorporation events, e.g. tags cleaved from tagged nucleotides, including those set forth in at least Formulas (I) and (II), are detected in the nanopore.

In some embodiments, each nucleotide analog has a covalently attached tag moiety that provides an identifiable, and distinguishable signature when detected with a nanopore. The strand extending enzyme (e.g., DNA polymerase) specifically binds the tagged nucleotide compound that is complimentary to a template nucleic acid strand which is hybridized to the growing nucleic acid strand at its active site. The strand extending enzyme then catalytically couples (i.e., incorporates) the complementary nucleotide moiety of the tagged nucleotide compound to the end of the growing nucleic acid strand. Completion of the catalytic incorporation event results in the release of the tag moiety and the oligophosphate moiety (minus the one phosphate incorporated into the growing strand) which then passes through the adjacent nanopore. Even before it undergoes catalytic process that releases it from the incorporated nucleotide however, the tag moiety of a tagged nucleotide compound enters the pore of the nanopore under an applied potential and thereby alters the background positive ion flow through the nanopore. Generally, the presence of a tag moiety in a nanopore results in decreasing (or blocking) the flow of positive ions through the nanopore. This "blocking current" is detected as signal that is a percentage of (or below) the "open channel" (or "O.C.") current resulting from positive ion flow through the nanopore with no tag moiety present.

In some embodiments, nanopore-based sequencing utilizes an enzyme, such as one located in proximity to a nanopore, which incorporate protected nucleotides, e.g. those of at least Formulas (I) or (II) herein, into a growing (nascent) polynucleotide chain, wherein the growing polynucleotide chain is complimentary to a corresponding template nucleic acid strand. Nucleotide incorporation events are catalyzed by the enzyme, such as DNA polymerase or any mutant or variant thereof and use base pair interactions with a template molecule to choose amongst the available nucleotides for incorporation at each location. "Nucleotide incorporation events," as that term is used herein, means the incorporation of a protected nucleotide (including any of those of Formulas (I) or (II)) into a growing polynucleotide chain. In some embodiments, byproducts of nucleotide incorporation events may be detected by the nanopore. In some embodiments, a byproduct may be correlated with the incorporation of a given type of nucleotide. In some embodiments, the byproduct passes through the nanopore and/or generates a signal detectable in the nanopore (see, e.g., FIG. 4). Released tag molecules, such as any of the tags identified above, are examples of byproducts of nucleotide incorporation events. By way of example, FIG. 1 depicts a DNA polymerase (120) bound in close proximity to a nanopore (130). A polynucleotide template (170) to be sequenced is added along with a primer (the template is associated with the enzyme). To this nanopore sequencing complex (including the primer), four differently tagged nucleotides (140) are added to the bulk aqueous phase. After polymerase catalyzed incorporation of the correct nucleotide, the tag will be released and pass through the nanopore (130) to generate a unique ionic current blockade signal (150), thereby identifying the added base electronically because each of the tags have distinct chemical structures. Additional details pertaining to such nanopore-based sequencing systems and methods are described in U.S. Pat. Nos. 9,605,309 and 9,557,294, the disclosures of which are hereby incorporated by reference herein in their entireties.

In some embodiments, a method for sequencing a nucleic acid molecule comprises (a) polymerizing protected tagged nucleotides (e.g. using an enzyme which incorporates one tagged nucleotide at a time using a first nucleic acid molecule as a template) wherein a tag associated with an individual nucleotide is released upon polymerization and where the protected tagged nucleotides have one of Formulas (I) or (II); and (b) detecting the released tag with the aid of a nanopore. In some embodiments, the blocking group of any 3' protected nucleotide is removed and then the processes is iteratively repeated. In some embodiments, the enzyme draws from a pool of protected tagged nucleotides. As noted herein, each type of protected nucleotide is coupled to a different tag molecule so that when the tags are released and pass near or through the nanopore, they may be differentiated from each other based on a signal that is generated (see, e.g., FIG. 1). In some embodiments, each tag may have a different detectable signal, e.g. different signal intensities, different signal amplitudes, etc. which may be interpreted such as by base calling algorithms.

In some embodiments, a released tag flows through the nanopore or in close proximity to the nanopore such that a sensing circuit detects an electrical signal associated with the tag as it passes through or near the nanopore (see FIG. 1). A detected signal (i.e. sequencing data) may be collected and stored in a memory location, and later used to construct a sequence of the nucleic acid. The collected signal may be processed to account for any abnormalities in the detected signal, such as errors. Suitable nanopore detectors are described in United States Patent Application Publication Nos. 2011/0193570 and 2018/0073071, the disclosures of which are hereby incorporated by reference herein in their entireties. Likewise, U.S. Pat. Nos. 9,377,437 and 8,324,914 describe the collection and analysis of electrical signals from nanopore-based sequencing systems, the disclosures of which are hereby also incorporated by reference herein in their entireties.

In some embodiments, the enzymes coupled or otherwise conjugated to nanopores include polynucleotide processing enzymes, e.g. DNA and RNA polymerases, reverse transcriptases, exonucleases, and unfoldases. In some embodiments, the enzyme is a helicase. In some embodiments, the enzyme can be a wild-type enzyme, or it can be a variant form of the wild-type enzyme. In some embodiments, the enzyme is a polymerase variant. For example, polymerase variants may include at least one alteration at a position corresponding to of H223, N224, Y225, H227, I295, Y342, T343, I357, S360, L361, I363, S365Q, S366, Y367, P368, D417, E475, Y476, F478, K518, H527, T529, M531, N535, G539, P542, N545, Q546, A547, L549, I550, N552, G553, F558, A596, G603, A610, V615, Y622, C623, D624, I628, Y629, R632, N635, M641, A643, I644, T647, I648, T651, I652, K655, W656, D657, V658, H660, F662, and L690. Other suitable polymerase variants are disclosed in United States Patent Application Publication No. 2016/0222363, the disclosure of which is hereby incorporated by reference herein in its entirety. Yet other suitable enzymes are disclosed in U.S. Pat. No. 9,797,009, the disclosure of which is hereby incorporated by reference herein in its entirety. Even further suitable enzymes are disclosed in United States Patent Application Publication No. 2016/0257942.

In some embodiments, the nanopores of the nanopore sequencing complex include, without limitation, biological nanopores, solid state nanopores, and hybrid biological-solid state nanopores. Biological nanopores of the nanopore sequencing complexes include OmpG from *E. coli*, sp., *Salmonella* sp., *Shigella* sp., and *Pseudomonas* sp., Cytolysin A (ClyA), and alpha hemolysin from *S. aureus* sp., MspA from *M. smegmatis* sp. The nanopores may be wild-type nanopores, variant nanopores, or modified variant nanopores. See, for example, United States Patent Application Publication No. 2017/0088588, the disclosure of which is hereby incorporated by reference herein in its entirety. In some embodiments, the variant nanopore of the nanopore sequencing complex is engineered to reduce the ionic current noise of the parental nanopore from which it is derived. Yet other nanopores are described in United States Patent Application Publication Nos. 2017/0268052, 2017/0356037 and 2018/0201993, the disclosures of which are hereby incorporated by reference herein in their entireties. Any nanopore variant now known or later discovered may be screened according to the methods described herein, such as contemporaneously with the screening of one or more enzyme variants (e.g. to identify a nanopore variant and enzyme variant pair that provides desirable properties).

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide, molybdenum disulfide). Methods for assembling nanopore sequencing complexes are described in U.S. Patent Application Publication No. 2017/0268052, the disclosure of which is hereby incorporated by reference herein in its entirety. Other suitable methods for complexing each of the different templates to nanopore-enzyme conjugates include those described in PCT Publication Nos. WO2014/074727, WO2006/028508, and WO2012/083249, the disclosures of each are hereby incorporated by reference herein in their entireties.

Figure 2:
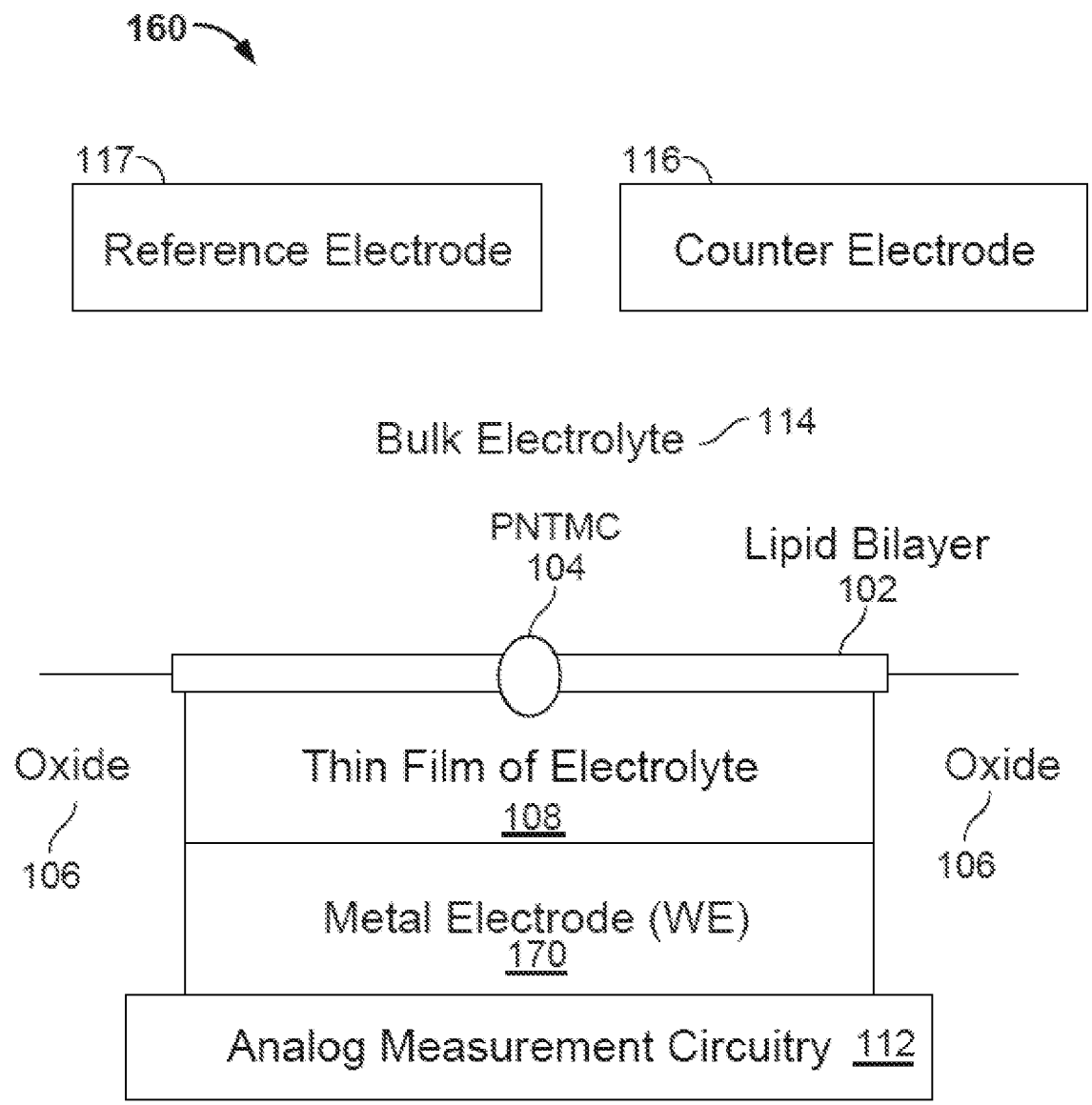
FIG. 2 illustrates an embodiment of a cell 100 in a nanopore based sequencing chip.

FIG. 2 illustrates an embodiment of a cell 160 in a nanopore based sequencing chip. In some embodiments, a membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. In some embodiments, a single PNTMC 104 is inserted into membrane 102 by electroporation. In some embodiments, the individual membranes in the array are neither chemically nor electrically connected to each other. Thus, each cell in the array is an independent sequencing machine, producing data unique to the single polymer molecule associated with the PNTMC. In some embodiments, PNTMC 104 operates on the analytes and modulates the ionic current through the otherwise impermeable bilayer.

With continued reference to FIG. 2, analog measurement circuitry 112 is connected to a metal electrode 170 (e.g. an electrode comprised of ruthenium, oxygen, titanium, or nitrogen) covered by a thin film of electrolyte 108. In some embodiments, the thin film of electrolyte 108 is isolated from the bulk electrolyte 114 by the ion-impermeable membrane 102. PNTMC 104 crosses membrane 102 and provides the only path for ionic current to flow from the bulk liquid to working electrode 170. In some embodiments, the cell also includes a counter electrode (CE) 116, which is an electrochemical potential sensor. In some embodiments, the cell also includes a reference electrode 117.

A chip for sequencing a nucleic acid sample may comprise a plurality of individually addressable nanopores. An individually addressable nanopore of the plurality can contain at least one nanopore formed in a membrane disposed adjacent to an integrated circuit. In some embodiments, each individually addressable nanopore can be capable of detecting a tag associated with an individual nucleotide.

Multiple nanopore sensors may be provided as arrays, such as arrays present on a chip or biochip. The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. Biochips and methods for making biochips are described in PCT Publication No. WO2015/061511, the disclosure of which is hereby incorporated by reference herein in its entirety. Further suitable biochips comprising a plurality of nanopores are described in United States Patent Application Publication No. 2017/0268052, the disclosure of which is hereby incorporated by reference herein in its entirety. Yet further suitable nanopore arrays are described in U.S. Pat. No. 8,986,928, the disclosure of which is hereby incorporated by reference herein in its entirety.

Incorporation of Protected Nucleotides or Protected Tagged Nucleotides into an Oligomer The present disclosure provides methods of synthesizing an oligomer, such as an oligonucleotide used for nanopore sequencing, the oligomer being derived from the protected nucleotides or protected tagged nucleotides disclosed herein.

Figure 3A:
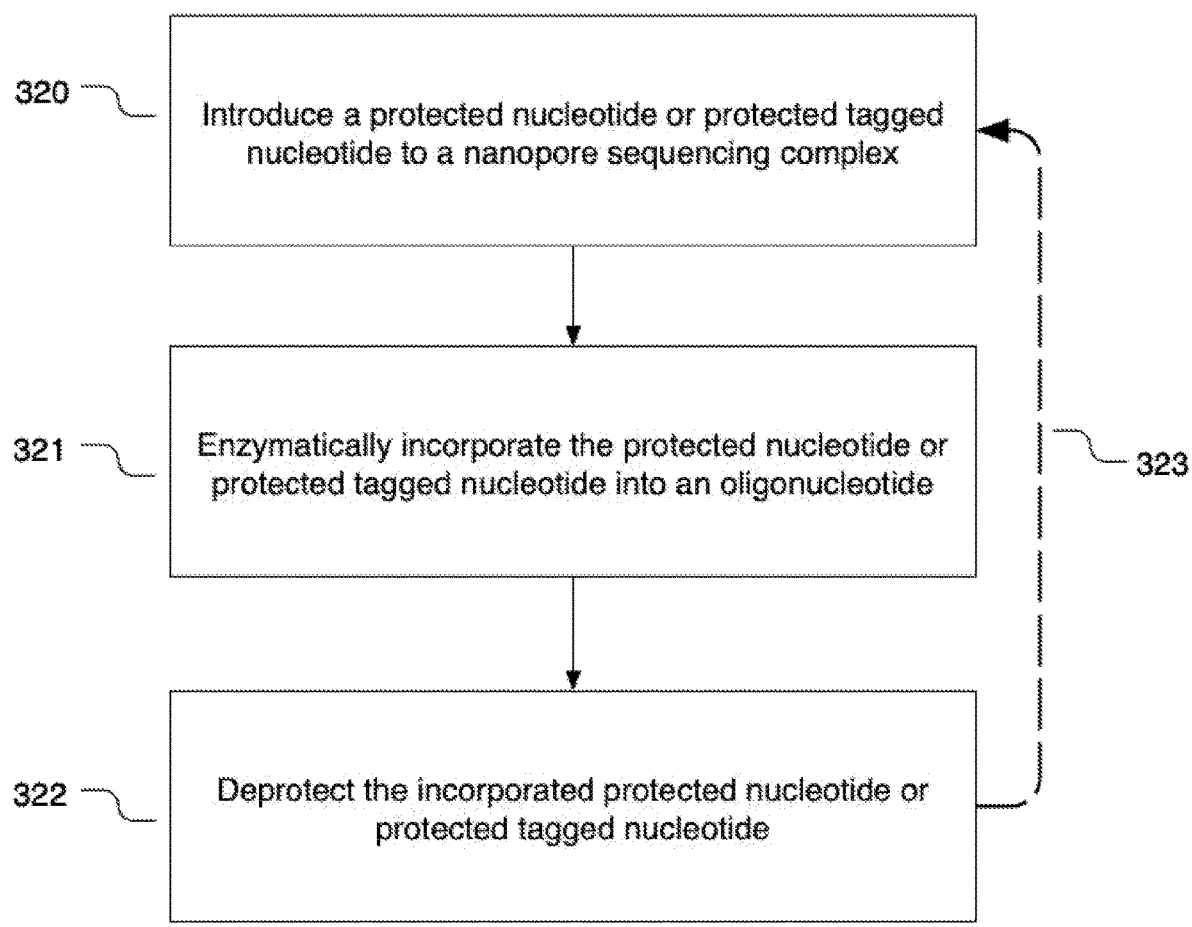
FIG. 3A provides a flowchart illustrates the steps of enzymatic incorporation of a protected nucleotide into a growing polynucleotide, e.g. growing polynucleotide which is complementary to a nucleic acid strand being sequenced in accordance with some embodiments of the present disclosure.

FIG. 3A sets forth a flowchart illustrating the general method of synthesizing an oligonucleotide using the nucleotides of any of Formulas (I), (II), (IIIA), (IIIB), (IIIC), (IIID), (IV), (VA), (VB), (VC), (VD), (VIIIA), (VIIIB), (VIIIC), (VIIID), (VIIIE), and (VIIIF). At step 320, a protected nucleotide or protected tagged nucleotide is introduced, such as to a nanopore sequencing complex. In some embodiments, the protected nucleotide or protected tagged nucleotide is introduced as a "pool" of protected nucleotides or protected tagged nucleotides, wherein the pool may comprise different protected nucleotides or protected tagged nucleotides, each differing at least in the nucleobase or tagged nucleobase coupled thereto. In some embodiments, the pool comprises protected nucleotides or protected tagged nucleotides which can hybridize with an A, T, G, or C nucleotide in DNA being sequenced (or, in the case of RNA sequencing, A, G, C, and U). In some embodiments, at least four different protected nucleotides are introduced in a pool.

At step 321, the protected nucleotide or protected tagged nucleotide is enzymatically incorporated into a growing oligonucleotide strand. By way of example, a polymerase enzyme may draw from the pool of protected nucleotides or protected tagged nucleotides and enzymatically incorporate the protected nucleotide or protected tagged nucleotide into the growing oligonucleotide strand. At step 322, the protected nucleotide or protected tagged nucleotide is deprotected, such as described herein. In embodiments where a protected tagged nucleotide is incorporated, the method may further comprise releasing the tag and detecting the released tag. n some embodiments the tag is released before deprotection (step 322) but after enzymatic incorporation (step 321). Alternatively, and in other embodiments, the tag is released after deprotection (step 322) but prior to the enzymatic incorporation of a second protected nucleotide or protected tagged nucleotide (step 323). In yet other embodiments, tag release and deprotection may occur in the same step (e.g. reagents may be chosen that act upon both the protecting group to facilitate deprotection while also acting upon a cleavable liker to enable release of the tag coupled thereto). Step 323 indicates that the process is iteratively repeated until an entire sequence nucleic acid sequence, e.g. a DNA or RNA sequence, is sequenced with the nanopore. The skilled artisan will appreciate that if a pool of nucleotides is introduced at step 320, then steps 321 and 322 may be repeated (step 323) as needed such that a polynucleotide may be sequenced in accordance with the present disclosure.

Figure 3B:
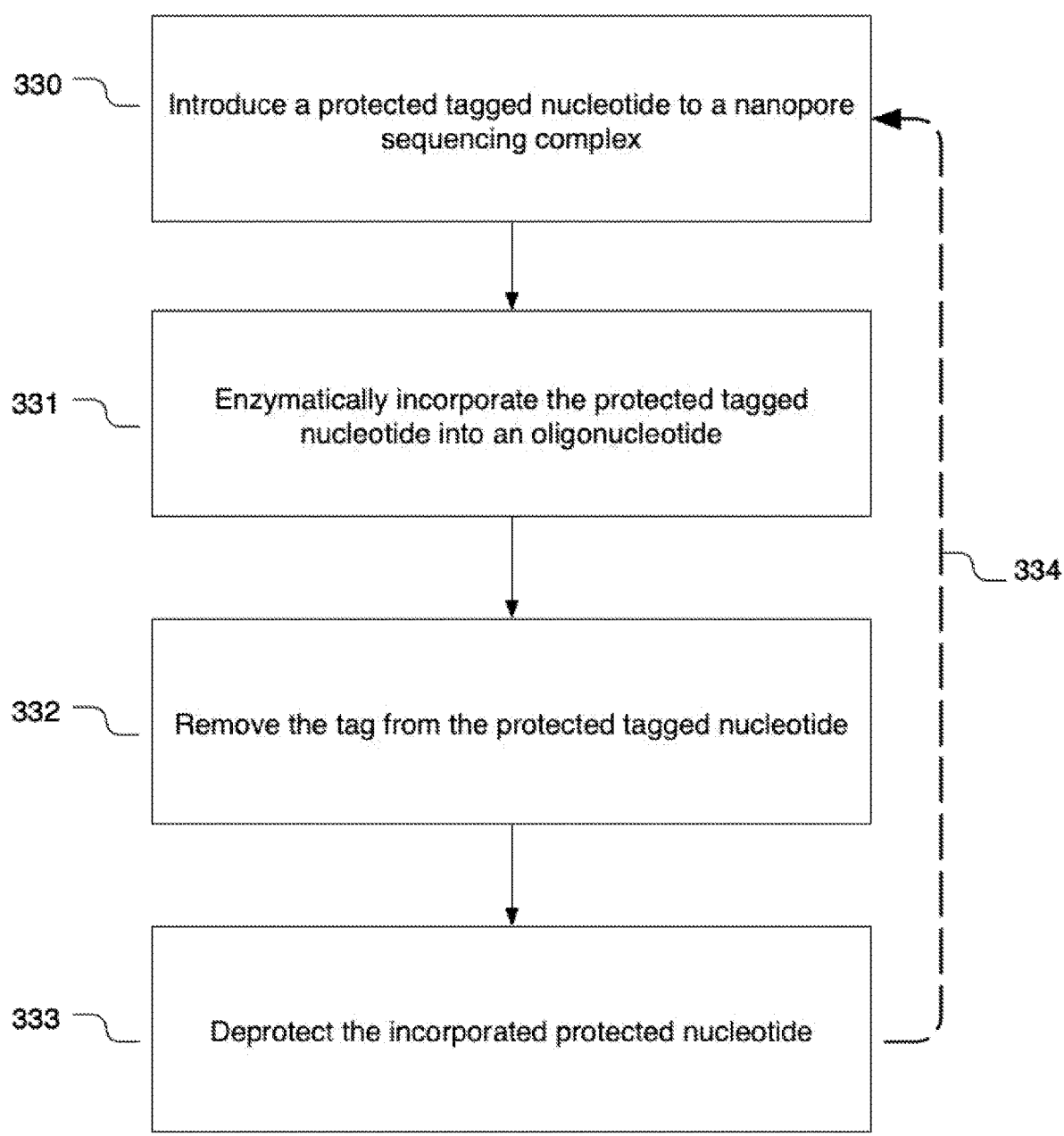
FIG. 3B provides a flowchart which illustrates the steps of enzymatic incorporation of a protected tagged nucleotide into a growing polynucleotide, e.g. growing polynucleotide which is complementary to a nucleic acid strand being sequenced in accordance with some embodiments of the present disclosure.

FIG. 3B sets forth a flowchart illustrating the steps of the enzymatic incorporation of a protected tagged nucleotide (step 331), such as one including a cleavable moiety as described herein, followed by the removal of the tag from the protected tagged nucleotide (332), and subsequent deprotection of the incorporated nucleotide (now a detagged protected nucleotide) (step 333). In some embodiments, each of the different protected tagged nucleotides is distinguished by the distinctive detectable signal the tag produces when it is incorporated into a new complementary strand by a strand-extending enzyme. In some embodiments, the released tags may flow through a nanopore after they are released from the nucleotide. In some embodiments, a voltage is applied to pull the tags through the nanopore. The skilled artisan will appreciate that the steps of enzymatic incorporating, tag removal, and deprotection may be repeated (step 334) as needed such that a polynucleotide may be sequenced in accordance with the present disclosure.

Figure 3C:
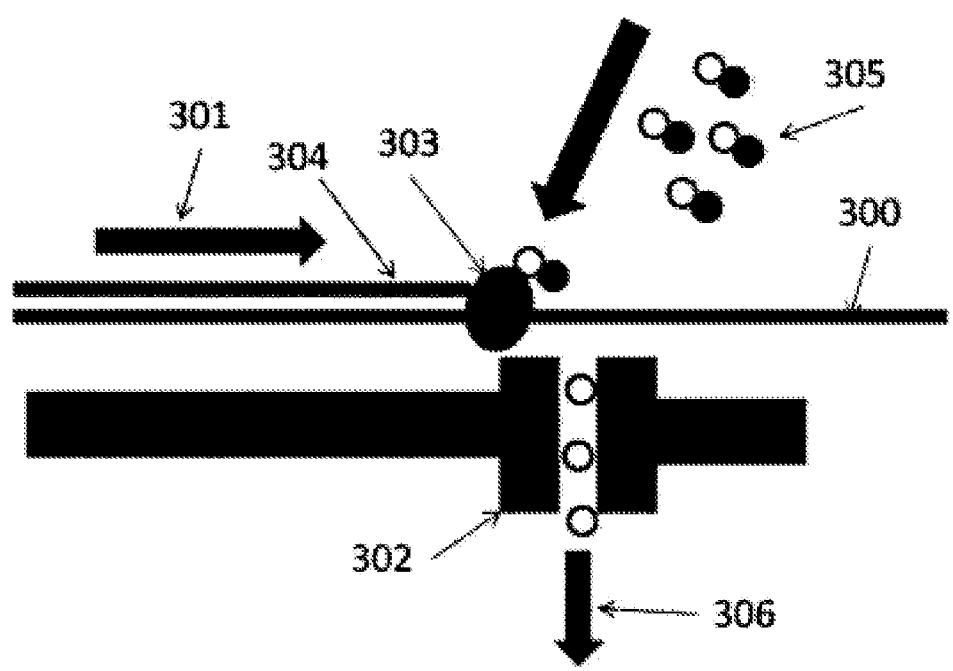
FIG. 3C illustrates a method for nucleic acid sequencing.

The method is further illustrated in FIG. 3C. As shown, the nucleic acid strand 300 passes across or in proximity to (but not through as indicated by the arrow at 301) the nanopore 302. An enzyme 303 (e.g., DNA polymerase) extends a growing nucleic acid strand 304 by incorporating one protected nucleotide or protected tagged nucleotide at a time using a first nucleic acid molecule as a template 300 (i.e., the enzyme catalyzes nucleotide incorporation events).

In some embodiments, and with continued reference to FIG. 3C, the enzyme draws from a pool of protected tagged nucleotides (filled circles at indication 305) attached to tag molecules (open circles at indication 305). Each type of protected tagged nucleotide is attached to a different tag molecule so that when the tags are released and pass through the nanopore 306, they may be differentiated from each other based on the signal that is generated in the nanopore. In some embodiments, as the tag passes into and/or through the nanopore, it may generate an electronic change. In some embodiments, the electronic change is a change in current amplitude, a change in conductance of the nanopore, or any combination thereof. Among the detectable signal characteristics, alone or in combination, that can be used to distinguish the protected tagged nucleotides in a nanopore detection method is the change in ion flow caused by the presence of the tag in the nanopore, which in turn results in a change in the current level measure across the electrodes of the nanopore detection system (under either DC or AC potential). "Ion flow," as used herein, refers to the movement of ions, typically in a solution, due to an electromotive force, such as the potential between an anode and a cathode. Ion flow typically can be measured as current or the decay of an electrostatic potential. Accordingly, in some embodiments, the present disclosure provides a set of protected tagged nucleotides each with a different tag, wherein each different tag causes a different ion flow through the pore resulting in a different detectable tag current level across the electrodes when it is situated in the nanopore.

Figure 4:
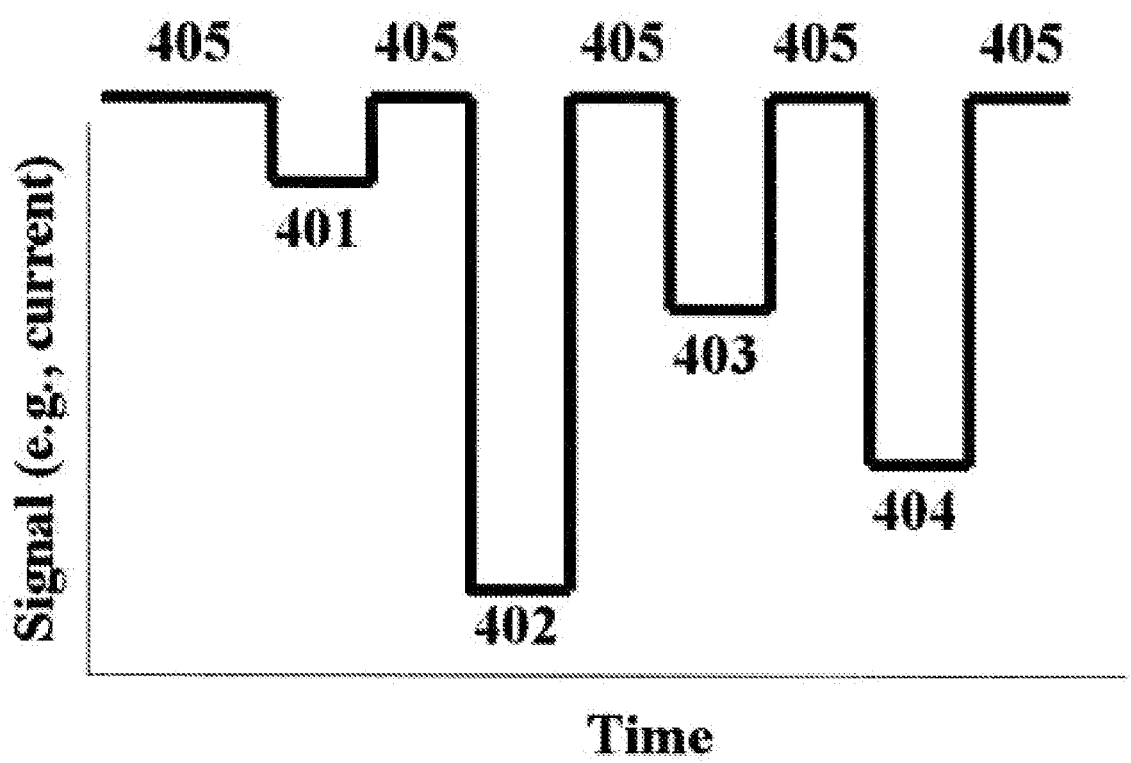
FIG. 4 shows an example of a signal generated by the passage of tags through a nanopore.

FIG. 4 provides an example of different signals being generated by different tags as they are detected by the nanopore. Four different signal intensities (401, 402, 403 and 404) are detected. These may correspond to four different tags, such as tags included within any of the protected tagged nucleotides disclosed herein. For example, the tag presented to the nanopore and/or released by incorporation of adenosine (A) may generate a signal with an amplitude 401. A tag presented to the nanopore and/or released by incorporation of cytosine (C) may generate a signal with a higher amplitude 403; a tag presented to the nanopore and/or released by incorporation of guanine (G) may generate a signal with an even higher amplitude 404; and a tag presented to the nanopore and/or released by incorporation of thymine (T) may generate a signal with a yet higher amplitude 402. The signal may return to a baseline level 405 between detections in some cases.

Figure 6:
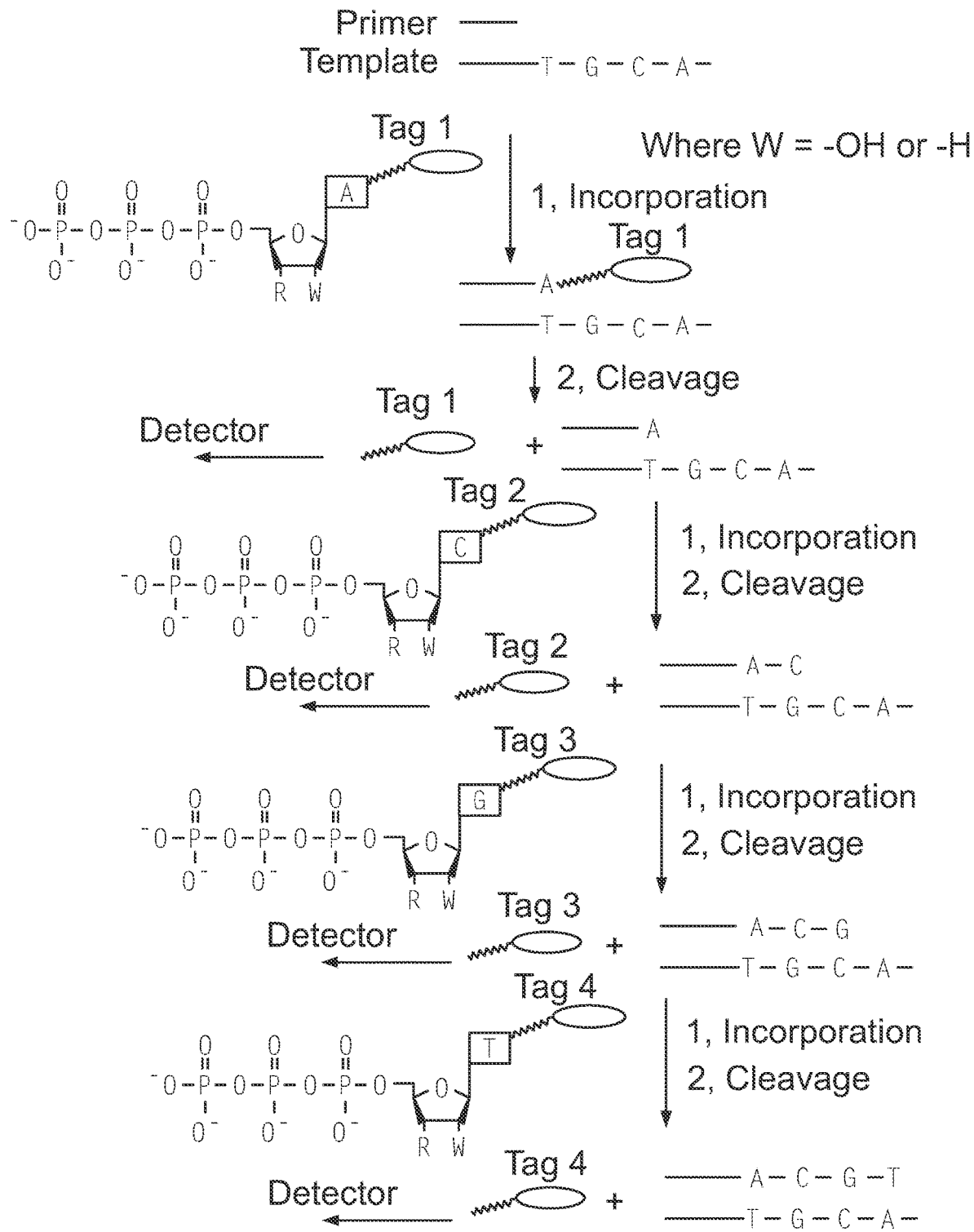
FIG. 6 illustrates a DNA extension reaction using base-tagged nucleotide analogs.

FIG. 6 further illustrates the incorporation of protected tagged nucleotides into a growing polynucleotide strand. As illustrated, each protected tagged nucleotide includes an R group representing a protecting group in accordance with the present disclosure (e.g. R may represent the 'Protecting Group' or the -Spacer-Blocking Moiety of Formulas (I) and (II), respectively. In this particular embodiment, cleavage of the Tag (i.e. Tags 1, 2, 3, and 4) also results in removal of the R group, i.e. the protecting moiety, such that additional tagged protected tagged nucleotides may be iteratively introduced.

Sequencing by Synthesis

The present disclosure also provides for methods of sequencing by synthesis (SBS), whereby the method utilizes any of the nucleotides or tagged nucleotides described herein, including any of the nucleotides (or salts thereof) of Formulas (I), (II), (IIIA), (IIIB), (IIIC), (IIID), (IV), (VA), (VB), (VC), (VD), (VIIIA), (VIIIB), (VIIIC), (VIIID), (VIIIE), and (VIIIF). SBS techniques generally involve the enzymatic extension of a nascent nucleic acid strand through the iterative addition of nucleotides against a template strand. Each nucleotide addition queries one or a few bases of the template strand. In one exemplary type of SBS, cycle sequencing is accomplished by stepwise addition of reversible terminator nucleotides containing, for example, a cleavable or photobleachable dye label (see, for example, PCT Application Publication No. WO 91/06678, the disclosure of which is hereby incorporated by reference herein in its entirety). In some embodiments, one or more protected tagged nucleotides are sequentially added to an extending polynucleotide chain in the 5' to 3' direction to form an extended polynucleotide complementary to a template nucleic acid to be sequenced. The identity of the base present in one or more of the added protected tagged nucleotide(s) can be determined in a detection or imaging step, such as after each nucleotide incorporation.

For example, a method for determining the sequence of a target single-stranded polynucleotide using sequencing by synthesis comprises: (a) providing protected tagged nucleotides (such as any of the protected tagged nucleotides of Formulas (I), (II), (IIIA), (IIIB), (IIIC), (IIID), (IV), (VA), (VB), (VC), (VD), (VIIIA), (VIIIB), (VIIIC), (VIIID), (VIIIE), and (VIIIF); (b) incorporating a protected tagged nucleotide into a complement of a target single stranded polynucleotide; (c) detecting the tag of the protected tagged nucleotide of step (b), thereby determining the type of nucleotide incorporated; (d) removing the 3' protecting group and the tag of the protected tagged nucleotide of step (b); and (e) optionally repeating steps (b)-(d) one or more times; thereby determining the sequence of the target single-stranded polynucleotide. In some embodiments, the method may further comprise releasing the tag and detecting the released tag. In some embodiments, the protected tagged nucleotide is de-protected, such as described herein. In some embodiments, the tag is released before deprotection of the 3' protecting group but after enzymatic incorporation. In other embodiments, the tag is released after deprotection of the 3' protecting group but prior to the enzymatic incorporation of a second protected nucleotide or protected tagged nucleotide. In some embodiments, cleavage of the tag and deprotection of the 3' protecting group take place substantially simultaneously. In some embodiments, the provided protected tagged nucleotides include at least four different protected tagged nucleotide (such as a pool of protected tagged nucleotides), each different protected tagged nucleotide including a different tag such each of the different protected tagged nucleotides are distinguishable from one another.

In some embodiments, the method for determining the sequence of a target polynucleotide using sequencing by synthesis can be carried out by contacting the target polynucleotide separately with the different protected tagged nucleotides to form the complement to that of the target polynucleotide and detecting the incorporation of the protected tagged nucleotides. As noted herein, such a method makes use of polymerization, whereby a polymerase enzyme extends the complementary strand by incorporating the correct protected tagged nucleotide complementary to that on the target. The polymerization reaction also requires a specific primer to initiate polymerization. For each cycle, the incorporation of the tagged nucleotide is carried out by the polymerase enzyme (such as those noted herein), and the incorporation event is then determined.

In some embodiments, the sequencing methods are carried out with the target polynucleotide arrayed on a solid support. Multiple target polynucleotides can be immobilized on the solid support through linker molecules, or can be attached to particles, e.g., microspheres, which can also be attached to a solid support material. In some embodiments, the polynucleotides can be attached to the solid support by a number of means, including the use of biotin-avidin interactions. Suitable solid supports include, but are not limited to, glass slides and beads, ceramic and silicon surfaces and plastic materials. In some embodiments, the support is a flat surface. In other embodiments, microscopic beads (microspheres) can also be used and can in turn be attached to another solid support by known means. The microspheres can be of any suitable size, typically in the range of from about 10 nm to about 100 nm in diameter. In some embodiments, the polynucleotides are attached directly onto a planar surface, e.g. a planar glass surface. In some embodiments, attachment is through a covalent linkage. Non-limiting examples of suitable arrays are described in PCT Application Publication No. WO 00/06770, the disclosure of which is hereby incorporated by reference herein in its entirety. The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. In some embodiments, single molecule arrays allow each individual polynucleotide to be resolved separately. In some embodiments, it is believed that sequencing single molecule arrays non-destructively allows a spatially addressable array to be formed.

To carry out the polymerase reaction, in some embodiments a primer sequence is annealed to the target polynucleotide, the primer sequence being recognized by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. In some embodiments, this structure may be immobilized to the solid support at any point on the molecule. In some embodiments, the protected tagged nucleotides of the present disclosure are then brought into contact with the target polynucleotide, to allow polymerization to occur. In some embodiments, the protected tagged nucleotides may be added sequentially, i.e., separate addition of each nucleotide type (e.g. a protected tagged nucleotide incorporating a nucleobase such as A, T, G or C), or added together. In some embodiments, if the protected tagged nucleotides are added together, each different type of protected tagged nucleotide having a different nucleobase is labelled with a different tag. In some embodiments, the polymerization step is allowed to proceed for a time sufficient to allow incorporation of a protected tagged nucleotide. In some embodiments, the protected tagged nucleotides not incorporated are then removed, for example, by subjecting the array to a washing step, and detection of the incorporated tags may then be carried out. In some embodiments, the method further comprises a deprotection step, as noted herein. In some embodiments, after detection, the tag may be removed using suitable conditions that cleave the linker.

In some embodiments, each of the protected tagged nucleotides can be brought into contact with the target sequentially, with removal of non-incorporated protected tagged nucleotides prior to addition of the next protected tagged nucleotide, where detection and removal of the tag is carried out either after addition of each protected tagged nucleotide, or after addition of all four of the protected tagged nucleotides. In other embodiments, all of the different types of protected tagged nucleotides are brought into contact with the target simultaneously, i.e., a composition comprising all of the different protected tagged nucleotides are brought into contact with the target, and non-incorporated nucleotides are removed prior to detection and subsequent to removal of the tag(s).

In some embodiments, the methods can comprise a first step and a second step, where in the first step, a first composition comprising two of the four nucleotides is brought into contact with the target, and non-incorporated protected tagged nucleotides are removed prior to detection and subsequent to removal of the tag, and where in the second step, a second composition comprising the two protected tagged nucleotides not included in the first composition is brought into contact with the target, and non-incorporated protected tagged nucleotides are removed prior to detection and subsequent to removal of the tag, and where the first step and the second step can be optionally repeated one or more times after deprotection of the 3' protecting group of the incorporated nucleotide.

In some embodiments, the methods described herein may also comprise a first step and a second step, where in the first step, a composition comprising one of four different protected tagged nucleotides is brought into contact with the target, and non-incorporated protected tagged nucleotides are removed prior to detection and subsequent to removal of the tag, and where in the second step, a second composition comprising the three protected tagged nucleotides not included in the first composition is brought into contact with the target, and non-incorporated protected tagged nucleotides are removed prior to detection and subsequent to removal of the tag, and where the first step and the second step can be optionally repeated one or more times after deprotection of the 3' protecting group of the incorporated nucleotide.

In some embodiments, the methods described herein may also comprise a first step and a second step, where in the first step, a first composition comprising three of the four different protected tagged nucleotides are brought into contact with the target, and non-incorporated nucleotides are removed prior to detection and subsequent to removal of the tag, and where in the second step, a composition comprising the protected tagged nucleotide not included in the first composition is brought into contact with the target, and non-incorporated protected tagged nucleotides are removed prior to detection and subsequent to removal of the tag, and where the first step and the second step can be optionally repeated one or more times after deprotection of the 3' protecting group of the incorporated nucleotide.

In some embodiments, the method for determining the sequence of a target polynucleotide comprises monitoring the sequential incorporation of complementary protected tagged nucleotides, wherein the protected tagged nucleotides comprise a detectable tag linked to the protected tagged nucleotide via a cleavable linker, and whereby incorporation is detected by monitoring the tag, and wherein the method further comprises a deprotection step to permit further protected tagged nucleotide incorporation to occur.

Additional components and methods for sequencing by synthesis are described in U.S. Pat. Nos. 9,605,310 and 9,441,272, the disclosures of which are hereby incorporated by reference herein in their entireties.

EXAMPLES

Preparation of Protected DMT-dT:

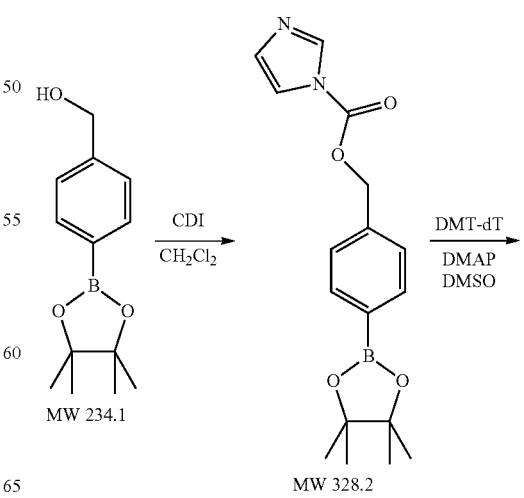

-continued

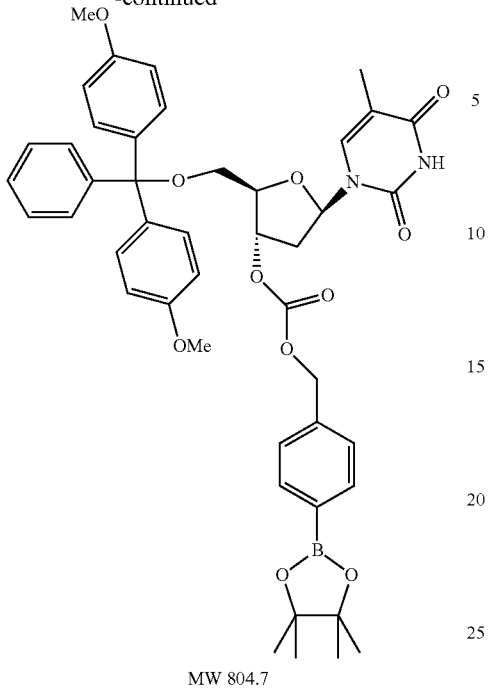

MW 804.7

255 mg (1.1 mmol) 4-(Hydroxymethyl)benzeneboronic acid pinacol ester and 340 mg CDI (2.1 mmol) were placed in a 15-mL tube. 1.5 mL dry dichloromethane was added, and the solution was shaken for 30 minutes. It was then diluted to 10 mL with Ethyl acetate and was washed with 5 mL water (×2). It was then dried over sodium sulfate anhydrous and concentrated under vacuum to give 300 mg white solid (80% yield).

440 mg DMT-dT (0.81 mmol) was dissolved in 1 mL anhydrous DMSO. 122 mg DMAP (1.0 mmol) was added and stirred to dissolve. Then, it was added to the 300 mg white solid above (0.91 mmol) and stirred under nitrogen overnight. Then it was dissolved in 100 mL Ethyl acetate and washed with 100 mL water (×3) and brine. It was dried over sodium sulfate anhydrous and evaporated under vacuum to give 800 mg viscous oil. It was purified over a 40 g silica gel combi flash with solvent hexanes/ethyl acetate (1% triethylamine) 50:50 to 0:100 over 15 min. The pure fraction with mass of 803 (negative mode) was concentrated under vacuum to give 30 mg boronate-carbonate-DMT-dT as a viscous film.

Preparation of Boronate-Carbonate-DMT-dT

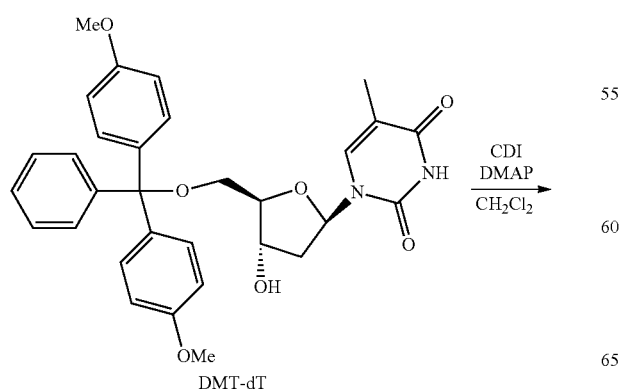

DMT-dT

-continued

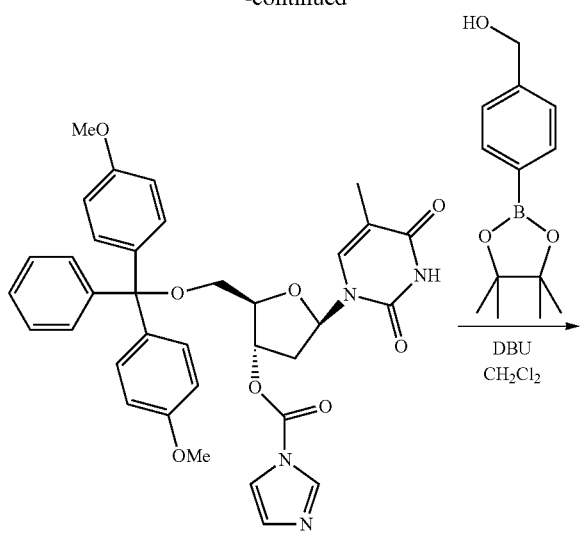

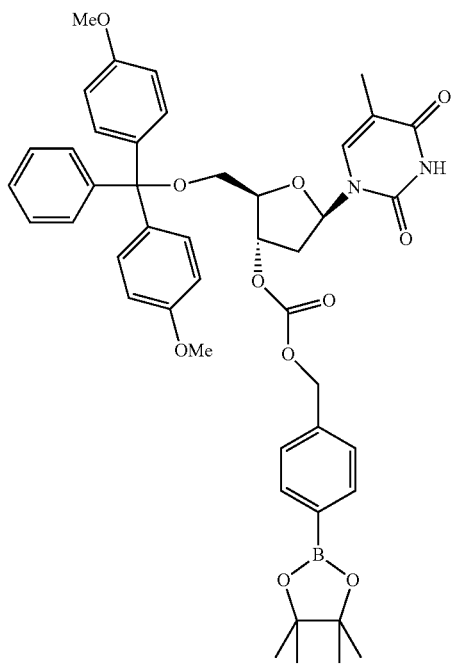

Deprotection of Protected DMT-dT:

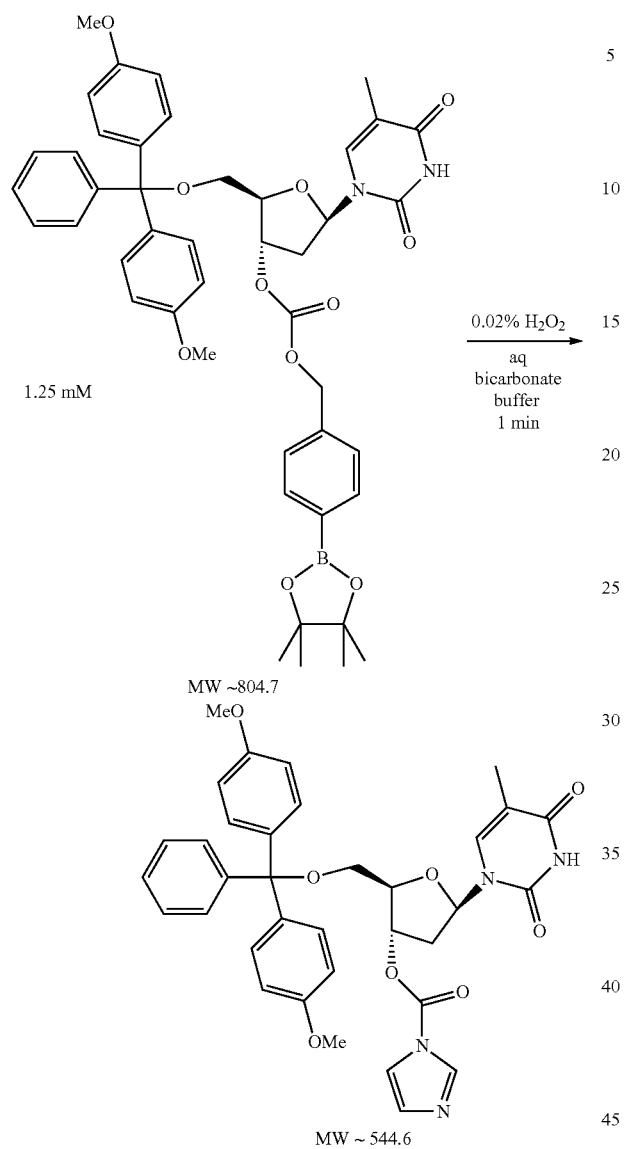

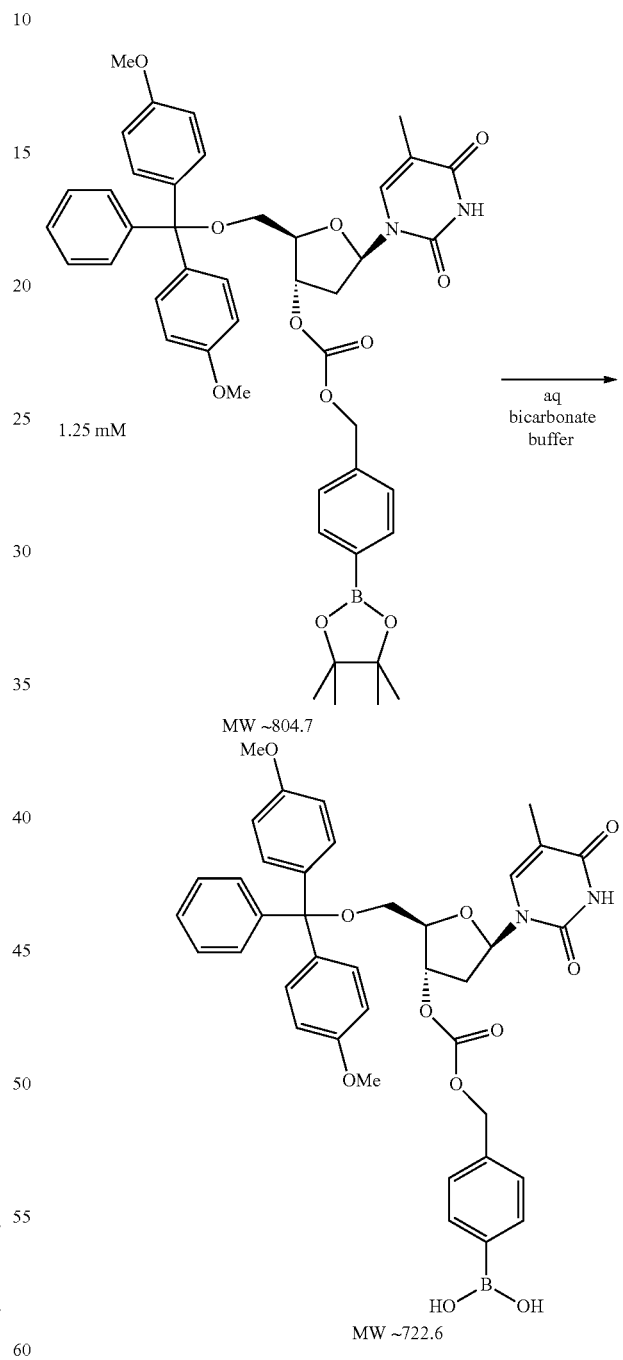

the reaction was vortexed for 10 minutes. Solution was still cloudy but to a lesser extent. 10 μL was diluted into 1 mL of water and was analyzed by LC-MS in negative mode). Two major mass peaks were observed: 803 from starting material and 721 from the hydrolysis of pinacol ester.

The control reaction was then shaken at rt for 40 hours. 10 μL was diluted into 1 mL of water and was analyzed by LC-MS in negative mode). The only major mass peak 721 from the hydrolysis of pinacol ester was observed.

Unmasking Reaction:

30 mg boronate-carbonate-DMT-dT product above was dissolved in 3 mL of acetonitrile to make a solution of 10 mg/mL (about 12.5 mM). The following reaction was then prepared:

10 μL of 10 mg/mL boronate-carbonate-DMT-dT was added to 90 μL of 20 mM sodium bicarbonate buffer pH ~8.5. Solution became cloudy due to the low solubility of boronate-carbonate-DMT-dT in water. 2μL of 1% aq $H_2O_2$ was added and the reaction was vortexed for 1 minute. Solution became clear again. 10 μL was diluted into 1 mL of water and was analyzed by LC-MS (in negative mode). The major mass peak of 543 showed unmasking of the compound all the way back to DMT-dT. No starting material was observed.

Control Reaction:

10 μL of 10 mg/mL boronate-carbonate-DMT-dT was added to 90 μL of 20 mM sodium bicarbonate buffer pH ~8.5. Solution became cloudy. 2μL of water was added and Preparation of a Protected Nucleotide Having a Malonyl Group 10 mmol of bis(hydroxymethyl) compound 1 is dissolved in 8 mL of dry pyridine. 9 mmol tert-butyldimethylsilyl chloride dissolved in 2 mL dry pyridine is added slowly and the reaction is stirred for 3 days. The mixture is evaporated to dryness under vacuum and is dissolved in 50 mL of CH₂Cl₂. It is washed with 50 mL of water, and the aqueous solution is extracted with 50 mL of CH₂Cl₂. All organic fractions are combined, dried over anhydrous sodium sulfate, and concentrated under vacuum. The product 2 is further purified by silica gel chromatography using hexanes/ethyl acetate as solvent. In this example, R may be —CN or —C(O)O-Et.

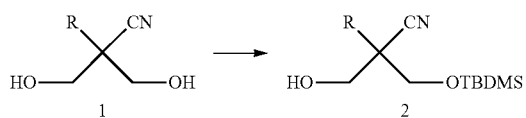

10 mmol of compound 2 is dissolved into a pre-mixed solution of 20 mL acetic anhydride, 6 mL acetic acid, and 30 mL of DMSO. The reaction is stirred overnight and is then carefully diluted with 150 mL cold 10% aqueous Na₂CO₃. The product is extracted with diethyl ether (5×50 mL). The organic phases are combined, dried over anhydrous sodium sulfate, and concentrated under vacuum. The product 3 is further purified by silica gel chromatography with CH₂Cl₂ as the solvent. In this example, R may be —CN or —C(O)O-Et.

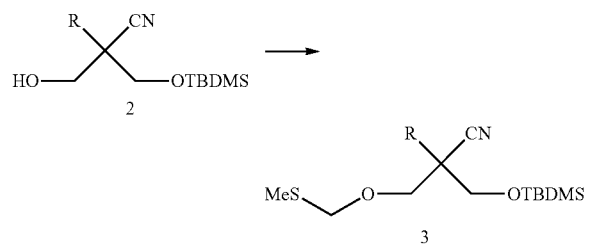

10 mmol of compound is dissolved in 50 mL of dry CH₂Cl₂ and the solution is stirred under argon. 12 mL (12 mmol) of 1M solution of Sulfuryl chloride in CH₂Cl₂ was added in 3 aliquots and the reaction is stirred for 1 hour under argon. The solvent is removed under vacuum and the residue is dissolved in 30 mL dry CH₂Cl₂. A solution of 17 mmol of potassium acetate and 7.5 mmol dibenzo-18-crown-6 in 30 mL dry CH₂Cl₂ is added, and the reaction is stirred for 1.5 h. 80 mL Ethyl acetate is added, and the organic phase is washed with 100 mL water. It is dried over sodium sulfate and concentrated under vacuum. The product 4 is further purified by silica gel chromatography with CH₂Cl₂ as the solvent. In this example, R may be —CN or —C(O)O-Et.

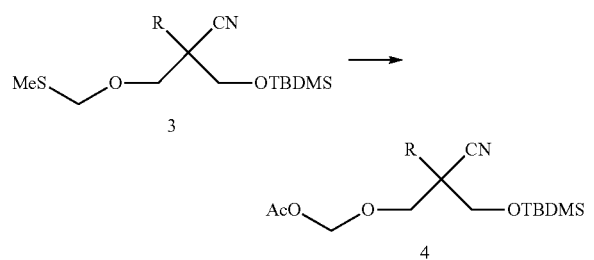

10 mmol of compound 4 is dissolved in 30 mL of dry THF and 2 mL (12 mmol) of triethylamine trihydrofluoride is added. The reaction is stirred for 1 week. 18 mL of aqueous 2M triethylammonium acetate is added, and the mixture is evaporated to dryness under vacuum. The residue including compound 5 is purified by silica gel chromatography with CH₂Cl₂ and methanol as solvents. In this example, R may be —CN or —C(O)O-Et.

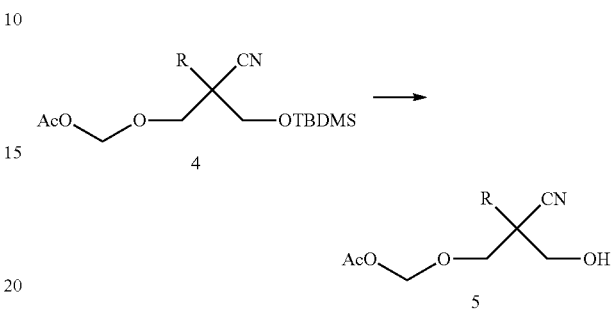

10 mmol of compound 5 is dissolved in 20 mL 1,2-dichloroethane and 20 mmol of pyridine is added and the solution is stirred in −10° C. 12 mmol of pre-chilled trifluoromethanesulfonic anhydride in 10 mL of 1,2-dichloroethane is added and the mixture is stirred for 30 min at −10° C. It is then quenched with 200 mL of 5% aqueous NaHCO₃ and the mixture is stirred for 30 min at room temperature. The organic layer is separated, dried over sodium sulfate and concentrated under vacuum. The residue including compound 6 is directly used in next step without further purification. In this example, R may be —CN or —C(O)O-Et.

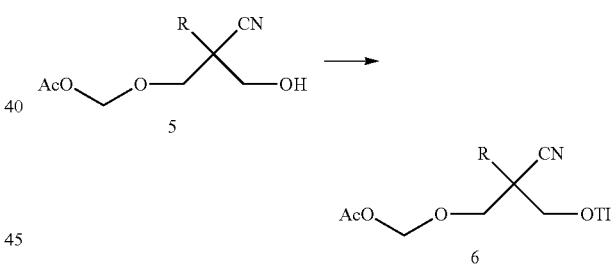

2 mmol of compound 6 is dissolved in 1 mL of DMF and is added to a solution of 1 mL 1 M dATP, dCTP, dGTP, or dTTP in 50 mM HEPES buffer pH 7.5. The reaction is stirred at 37 C for 24 hours. The solvent is then removed under vacuum and the residue is purified by reverse phase HPLC using 50 mM triethylammonium bicarbonate pH 7.5 and acetonitrile as solvents. The solvent is removed, and the product is precipitated as sodium salt using sodium perchlorate in acetone. The identity and purity of the product 7 is analyzed by LC-MS analytical methods. In this example, R may be —CN or —C(O)O-Et.

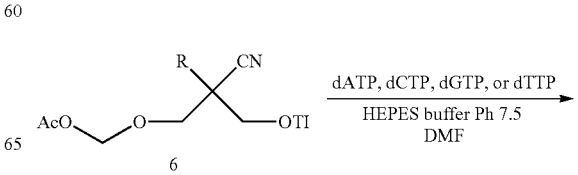

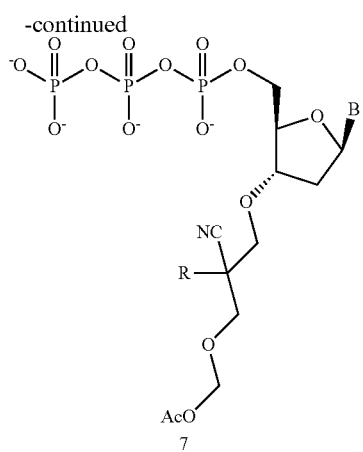

An alternative method for the preparation is set forth below:

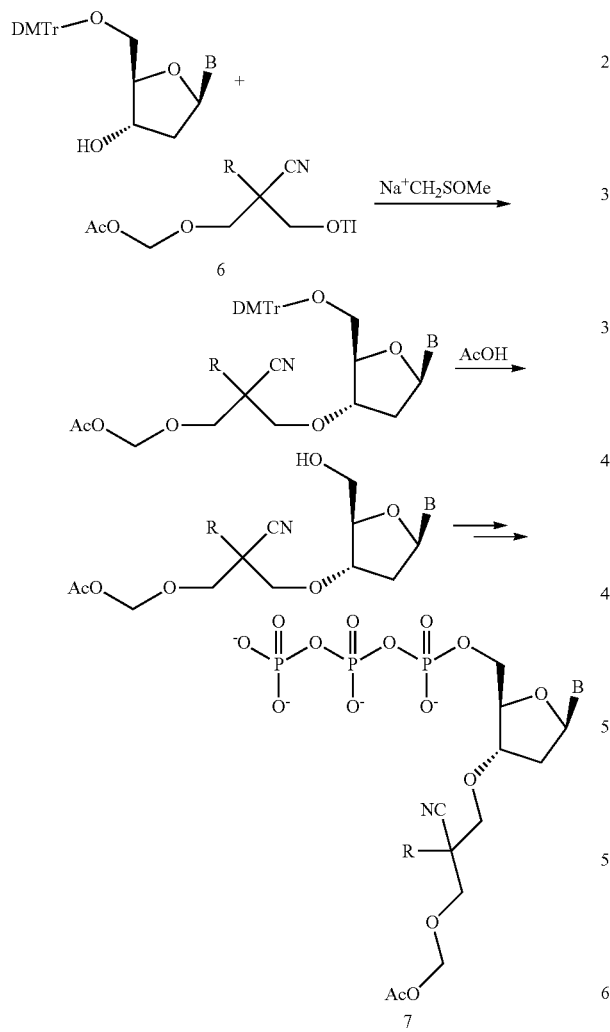

5'-dimethoxytrityl (DMTr-) protected deoxynucleotides are dissolved in dry THF and slowly treated with 1.2 equivalent of dimysl sodium. After the reaction is stirred for 30 minutes, 1.2 equivalent of triflates (compound 6) is slowly added to the mixture. After the reaction is completed, the solvent is evaporated, and the product is purified by silica gel column chromatography. The DMTr protecting group is removed by treatment with acetic acid and the triphosphates (compound 7) is obtained via classic triphosphate preparation methods and purified by ion-exchange and reverse-phase HPLC purification methods. In this example, R may be —CN or —C(O)O-Et.

5'-O-DMT-N3-anisoyl-thymidine

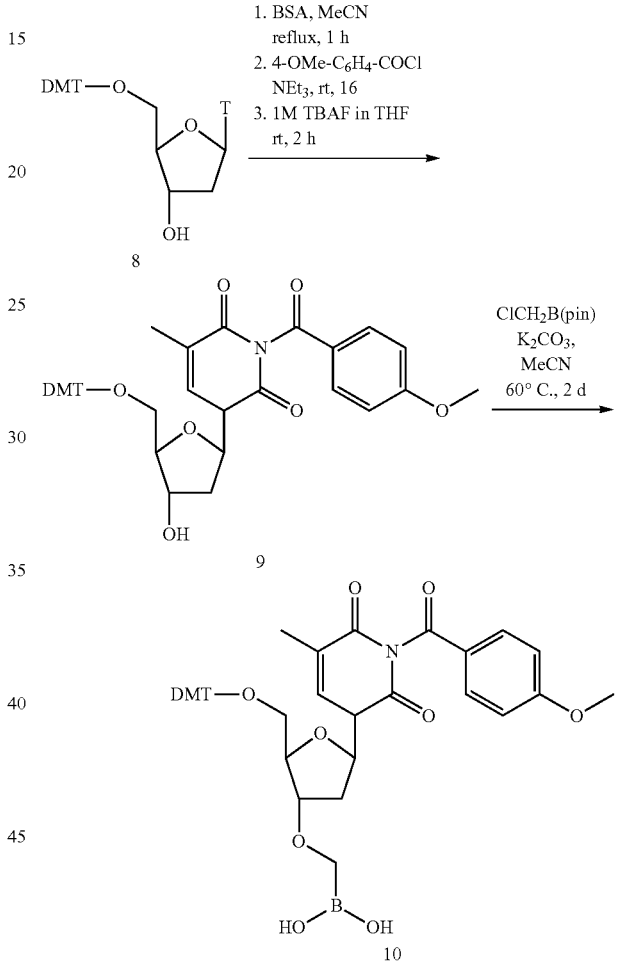

To a solution of 5'-O-DMT-thymidine 8 (5.08 g, 9.33 mmol) in dry MeCN (100 mL) was added N,O-bis-trimethylsilyl-acetamide (4.60 mL, 3.83 g, 18.8 mmol). The reaction mixture was refluxed for 1 h and subsequently cooled to rt. Next, 4-methoxy benzoyl chloride (1.65 mL, 2.08 g, 12.2 mmol) and NEt$_3$ (2.60 mL, 1.89 g, 18.7 mmol) were added and the reaction mixture was stirred over night at rt. TBAF (1 M in THF, 28.5 mL, 28.5 mmol) was added and the resulting mixture was stirred at rt. After 2 h, the mixture was concentrated in vacuo and the crude product was dissolved in EtOAc (200 mL). The organic phase was washed (2×100 mL sat. NaHCO$_3$; 100 mL brine) and dried over Na$_2$SO$_4$. 5'-O-DMT-N3-anisoyl-thymidine 9 (1.95 g, 2.78 mmol, 31% over three steps) was isolated as a yellow solid after purification by flash-chromatography on silica-gel using n-hexane/ethylacetate (2/1→1/2) as a mobile phase.

ESI-MS: m/z=677.9 ($C_{39}H_{37}N_2O_9$ (M-H$^-$); calc. 677.2 (M-H$^-$)).

3'-O-methylboronic acid-5'O-DMT-N3-anisoyl-thymidine 10

5'-O-DMT-N3-anisoyl-thymidine 9 (648 mg, 1.00 mmol) was dissolved in dry MeCN (20 mL) under argon atmosphere and in presence of activated molecular sieves (4 Å). $K_2CO_3$ (415 mg, 3.00 mmol) was added and the suspension was stirred for 30 min at rt. 2-(Chloromethyl)-4,4,5,5-tetramethyl-1,3,2-dioxaborolane (351 µL, 442 mg, 2.00 mmol) was added and the reaction mixture was stirred at 60° C. After 24 h, additional $K_2CO_3$ (138 mg, 1.00 mmol) and of the alkyl chloride (176 µL, 222 mg, 1.00 mmol) was added. Stirring at 60° C. was continued for another 16 h. The mixture was cooled to rt, filtered and concentrated in vacuo. The crude product was purified by flash-chromatography on silica-gel using n-hexane/ethylacetate (1/2→1/4) and dichlormethane/methanol (2/1) as a mobile phase. Final purification by RP-HPLC afforded the desired 3'-O-methylboronic acid-5'-O-DMT-N3-anisoyl-thymidine 10 (167 mg, 0.23 mmol, 23%) as a white solid after lyophilization.

ESI-MS: m/z=735.4 ($C_{40}H_{40}BN_2O_{11}$, (M-H$^-$); calc. 735.3 (M-H$^-$)).

3'-O-Methylboronic acid-N3-anisoyl-thymidine 11

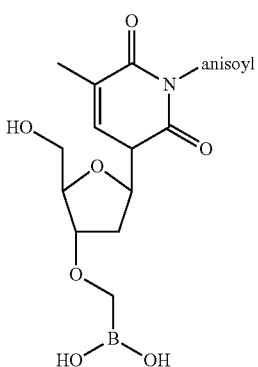

11

3'-O-Methylboronic acid-N3-anisoyl-thymidine 11 was formed as a side product during the synthesis of 3'-O-methylboronic acid-5'-O-DMT-N3-anisoyl-thymidine 10 by partial deprotection of the 5'-DMT protecting group and isolated in the course of RP-HPLC purification. 3'-O-Methylboronic acid-N3-anisoyl-thymidine 11 (5 mg, 11.5 µmol) was isolated as a white solid after lyophilization.

ESI-MS: m/z=433.2 ($C_{19}H_{22}BN_2O_9$(M-H$^-$); calc. 433.1 (M-H$^-$)).

Deprotection
3'-O-methylboronic acid-5'O-DMT-N3-anisoyl-thymidine 10→5'O-DMT-N3-anisoyl-thymidine 9

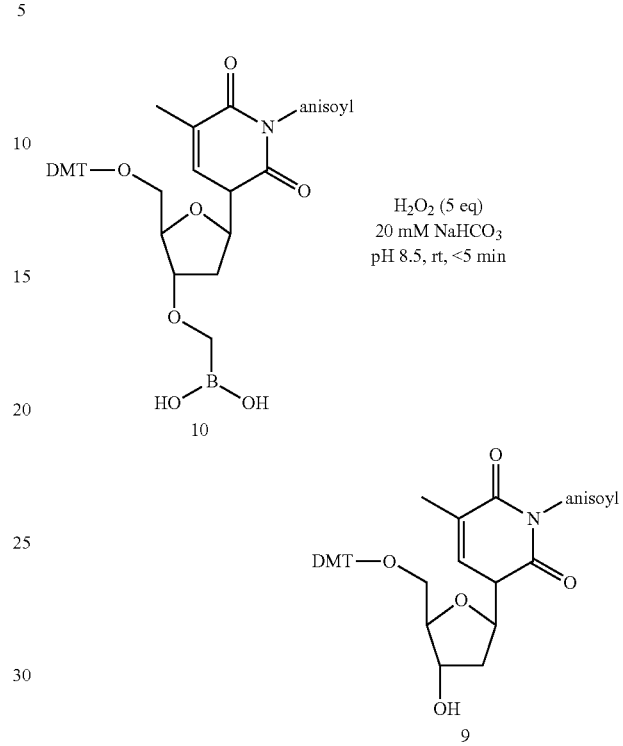

The methylboronic acid-protected nucleoside 10 (1.23 mg, 1.67 µmol) was dissolved in 134 µL MeCN (c(nucleoside)=12.5 mM). 20 µL of this solution were diluted with 80µL of MeCN and supplemented with 100 µL of aq. 40 mM NaHCO$_3$ (c(nucleoside)=1.25 mM). 50 µL of the solution were added to 1 µL of aq. 1% $H_2O_2$ and the reaction mixture was agitated at rt. As indicated by HPLC-MS analysis, quantitative conversion of the starting material 10 (ESI-MS: m/z=735.4 ($C_{40}H_{40}BN_2O_{11}$(M-H$^-$); calc. 735.3 (M-H$^-$)) into the desired alcohol 9 (ESI-MS: m/z=677.5 ($C_{39}H_{37}N_2O_9$ (M-H$^-$); calc. 677.2 (M-H$^-$)) proceeded within less than 5 minutes.

3'-O-methylboronic acid-N3-anisoyl-thymidine 11→N3-anisoyl-thymidine 12

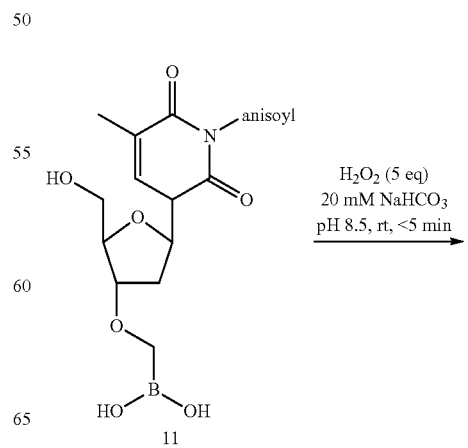

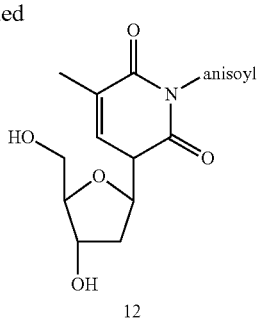

The methylboronic acid-protected nucleoside 11 (0.75 mg, 1.73 μmol) was dissolved in 138 μL MeCN (c(nucleoside)=12.5 mM). 20 μL of this solution were diluted with 160 μL of aq. 20 mM NaHCO$_3$ (c(nucleoside)=1.25 mM). 50 μL of the solution were added to 1 μL of a 1% H$_2$O$_2$. As indicated by HPLC-MS analysis, quantitative conversion of the starting material 11 (ESI-MS: m/z=433.3 (C$_{19}$H$_{22}$BN$_2$O$_9$ (M-H$^-$); calc. 433.1 (M-H$^-$)) into the desired alcohol 12 (ESI-MS: m/z=375.3 (C$_{18}$H$_{19}$N$_2$O$_7$ (M-H$^-$); calc. 375.1 (M-H$^-$)) proceeded within less than 5 minutes.

Synthesis of Aryl(azidomethyl) Blocked Nucleotide Triphosphate

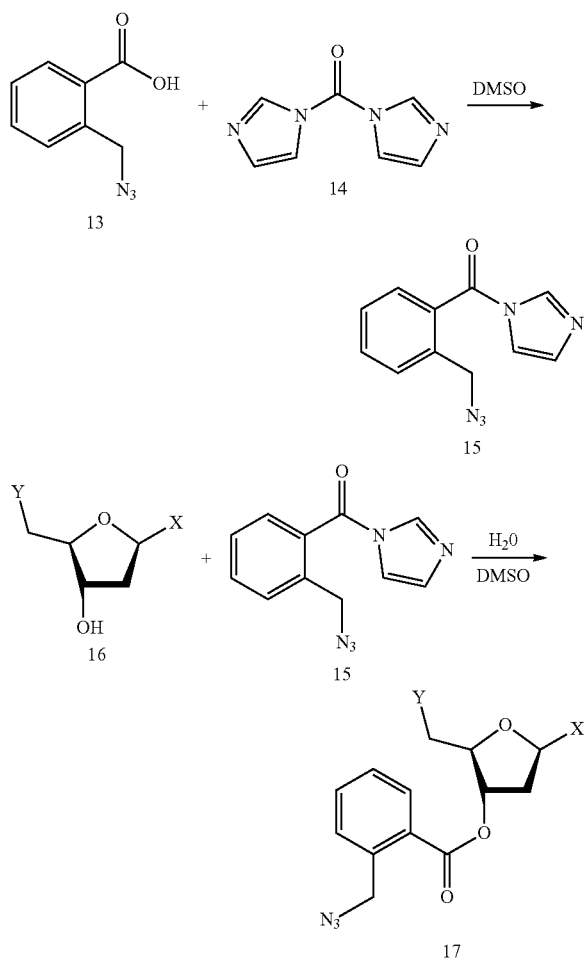

The above-identified structures, Y and X are as described herein.

1.22 grams of 2-(azidomethyl)benzoic acid 13 was dissolved in 8.1 mL anhydrous DMSO and the clear solution stirred at room temperature. 1.11 grams N,N'-carbonyldiimidazole 14 was added portion-wise with stirring (1 equivalent). Upon dissolution of the CDI, the reaction was stirred at room temperature for 2 hours and the resulting mixture (product:imidazole, 1:1) was used as a 0.85M stock solution of the activated acyl imidazolide 15.

55 mg of dATP 16 (disodium salt) was placed in a reaction tube. 182 μL of the activated acyl imidazole 15 solution (0.85M in DMSO) was added, followed by 500 μL anhydrous DMSO and 500 μL water. The resulting clear solution was incubated at 55° C. overnight then cooled to room temperature. Analytical LCMS confirmed the formation of product 17 (MW obs 649.04, MW calc 649) as well as a diphosphate side product (MW obs 569.07). The material was purified by reverse phase HPLC on a C18 column using a gradient of acetonitrile in 0.1M triethylammonium acetate, pH 7.5. Product containing fractions were collected and lyophilized to afford a white solid.

TCEP Reduction of Blocked Azides

A 1 mM solution of the dATP blocked (azidomethyl) benzoate ester 17 in 30 mM HEPES pH 7.5 was treated with 15 mM TCEP (Tris(2-carboxyethyl)phosphine) and incubated at room temperature. For LCMS analysis a 10× dilution of the reaction mixture in water is analyzed using an acetonitrile in 100 mM triethylammonium acetate gradient and detection at 260 nM and by negative mode ESI-MS. Prior to cleavage the blocked dATP elutes at 4 min in the LC gradient with a MW of 649.03 (negative mode). Upon reduction of the azide and intramolecular cyclization and deprotection, the released dATP elutes at 1.8 min in the LCMS gradient with a MW of 489.99 (negative mode).

Single Nucleotide Incorporation:

The efficiency of incorporation of triphosphate 7 by a polymerase is examined in a single nucleotide insertion experiment using a 15-mer primer and 25-mer templates containing the complementary bases at the insertion sites. The success of insertion is analyzed using LC-MS analytical methods.

Cleavage of Masking Group:

The single nucleotide insertion experiment mixture is subjected to an unspecified amount of an esterase for between about 1 and about 30 minutes. The success of complete unmasking was verified by LC-MS analytical methods.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

Additional Embodiments

In another aspect of the present disclosure is a nucleotide or a salt thereof of Formula (IIIA):

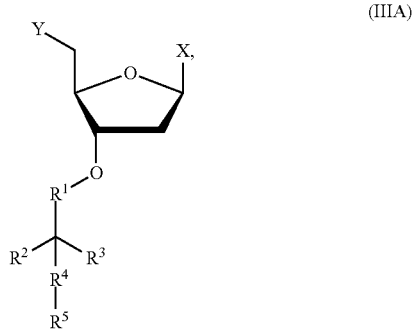

(IIIA)

wherein
X is a nucleobase or a tagged nucleobase;
Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5.
$R^1$ is a bond;
$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;
$R^4$ is a bond, a substituted or unsubstituted 5- to 7-membered aryl group, —CH=CH—, a substituted or unsubstituted 5- or 6-membered heterocycloalkyl group, or —O—C(O)-aryl-;
$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

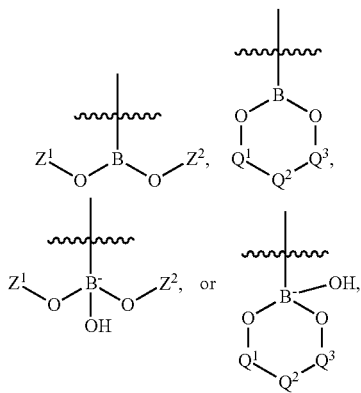

$Z^1$ and $Z^2$ are independently H, a $C_1$-$C_4$ alkyl group, or a 5- to 6-membered aryl group optionally substituted with one or more hydroxyl groups;
$Q^1$ and $Q^3$ are each independently a bond, —C($R^e$)($R^f$)—, or —C(O)—;
$Q^2$ is a bond, o-phenylene, or —[C($R^e$)($R^f$)]$_w$—, where w is 1 or 2;
$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;
$R^x$ is a substituted or unsubstituted 5- or 6-membered aromatic group or heteroaromatic group;
n is 0 or an integer ranging from 1 to 3; and
p and q are each independently zero or an integer ranging from 1 to 3;
provided that when $R^1$ and $R^4$ are both bonds and when $R^2$ and $R^3$ are both H, then $R^5$ is not an azide.

In some embodiments, $R^4$ is a bond. In some embodiments, $R^4$ is a bond and $R^2$ or $R^3$ is H.
In some embodiments, $R^4$ is a 6-membered aryl group. In some embodiments, $R^4$ is a 6-membered aryl group and at least one of $R^2$ or $R^3$ is H.
In some embodiments, $R^4$ is —CH=CH—.
In some embodiments, $R^5$ is

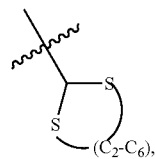

where $C_2$-$C_6$ represents a saturated 2 to 6 carbon alkyl chain which may be substituted or unsubstituted. In some embodiments, $R^5$ is

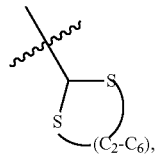

where $C_2$-$C_6$ represents a saturated 2 to 6 carbon alkyl chain which may be substituted or unsubstituted, and where $R^2$ is —[(C($R^a$)($R^b$))$_p$—O]$_q$ ($R^a$) or —C(O)—O$R^a$— and wherein at least one $R^a$ is a $C_1$-$C_6$ alkyl group.
In some embodiments, $R^5$ is —(C($R^a$)($R^b$))$_n$—CN or —(C($R^a$)($R^b$))$_n$—N$^+$C$^-$. In some embodiments, $R^5$ is —(C($R^a$)($R^b$))$_n$—CN or —(C($R^a$)($R^b$))$_n$—N$^+$C$^-$ and where $R^2$ is —[(C($R^a$)($R^b$))$_p$ O]$_q$—($R^a$) or —C(O)—O$R^a$— and wherein at least one $R^a$ is a $C_1$-$C_6$ alkyl group.

In another aspect of the present disclosure is a nucleotide or a salt thereof of Formula (IIIA):

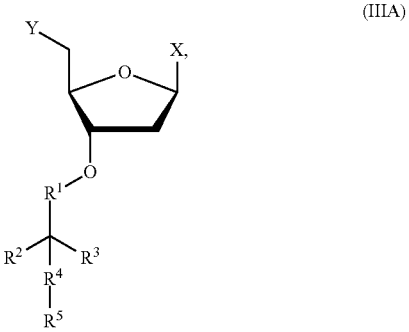

(IIIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5.

$R^1$ is —C(O)—O—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted 5- to 7-membered aryl group, —CH═CH—, a substituted or unsubstituted 5- or 6-membered heterocycloalkyl group, or —O—C(O)-aryl-;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

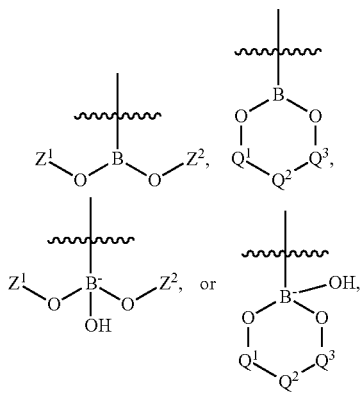

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide.

In some embodiments, $R^4$ is a 6-membered aryl group. In some embodiments, the 6-membered aryl group includes at least one substituent, wherein the at least one substituent is selected from the group consisting of methyl and ethyl. In some embodiments, $R^4$ is a 6-membered aryl group and at least one of $R^2$ or $R^3$ is H.

In another aspect of the present disclosure is a nucleotide or a salt thereof of Formula (IIIA):

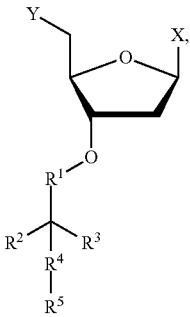

(IIIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5.

$R^1$ is —C(O)—$R^x$—;

$R^2$ and $R^3$ are each independently H, a saturated or unsaturated $C_1$-$C_6$ alkyl group, a $C_5$-$C_6$ aryl or heteroaryl group, a halogen, —[(C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a bond, a substituted or unsubstituted 5- to 7-membered aryl group, —CH═CH—, a substituted or unsubstituted 5- or 6-membered heterocycloalkyl group, or —O—C(O)-aryl-;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

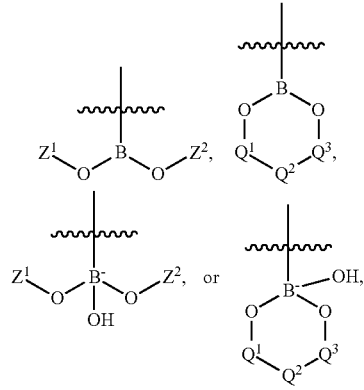

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide.

In some embodiments, $R^5$ is $-(C(R^a)(R^b))_n-N_3$.

The invention claimed is:

1. A nucleotide or a salt thereof of Formula (VA):

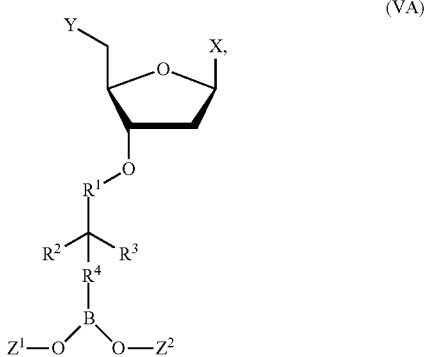

wherein

X is a nucleobase or a tagged nucleobase;

Y is $-O-P(O)(OH)-[O-P(O)(OH)]_z-OH$ or $-O-P(O)(OH)-[O-P(O)(OH)]_z-O$-oligonucleotide, where z is 0 or an integer ranging from 1 to 5;

$R^1$ is a bond, a $-CH_2-$, $-C(O)-O-$, $-C(O)-NR^a-$, or $-C(O)-R^x-$;

$R^2$ and $R^3$ are each independently H, a saturated or unsaturated $C_1$-$C_6$ alkyl group, a $C_5$-$C_6$ aryl or heteroaryl group, a halogen, $-[(C(R^a)(R^b))_p-O]_q$ ($R^a$), $-C(O)-OR^a$, $-C(O)-N(R^a)(R^b)$, $-(C(R^a)(R^b))_n-N^+C^-$, $-CN$, or $-NO_2$;

$R^4$ is a bond, a substituted or unsubstituted 5- to 7-membered aryl group, $-CH=CH-$, a substituted or unsubstituted 5- or 6-membered heterocycloalkyl group, or $-O-C(O)$-aryl-;

where $Z^1$ and $Z^2$ are independently H or a $C_1$-$C_4$ alkyl group;

$R^a$ and $R^b$ are each independently H or a saturated $C_1$-$C_6$ alkyl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3.

2. The nucleotide of claim 1, wherein at least one of $Z^1$ or $Z^2$ is H.

3. The nucleotide of claim 1, wherein both $Z^1$ and $Z^2$ are H.

4. The nucleotide of claim 1, wherein $R^1$ is a bond.

5. The nucleotide of claim 4, wherein $R^4$ is a bond.

6. The nucleotide of claim 5, wherein at least one of $R^2$ or $R^3$ is H.

7. The nucleotide of claim 4, wherein $R^4$ is a 6-membered aryl group.

8. The nucleotide of claim 7, wherein at least one of $R^2$ or $R^3$ is H.

9. The nucleotide of claim 1, wherein $R^1$ is $-C(O)-O-$.

10. The nucleotide of claim 9, wherein $R^4$ is a 6-membered aryl group.

11. The nucleotide of claim 10, wherein the 6-membered aryl group includes at least one substituent, wherein the at least one substituent is selected from the group consisting of methyl and ethyl.

12. The nucleotide of claim 1, wherein $R^1$ is $-CH_2-$, and both $Z^1$ and $Z^2$ are H.

13. A nucleotide or salt thereof having any one of Formulas (VIIIA) or (VIIID):

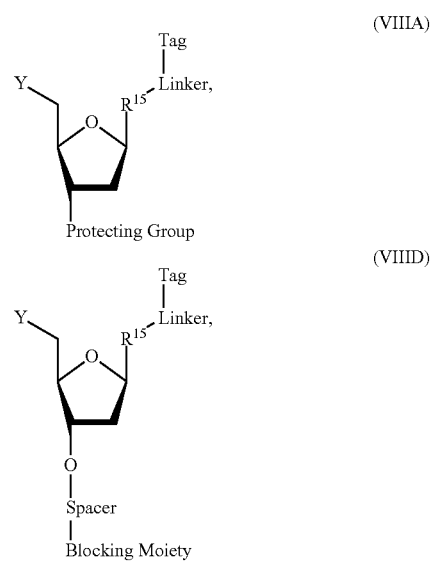

or wherein $R^{15}$ is a nucleobase;

Y is $-O-P(O)(OH)-[O-P(O)(OH)]_z-OH$ or $-O-P(O)(OH)-[O-P(O)(OH)]_z-O$-oligonucleotide, where z is 0 or an integer ranging from 1 to 5;

'Protecting Group' has the structure:

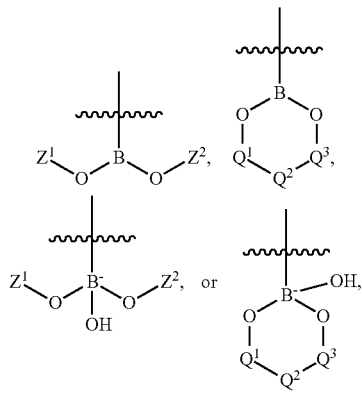

'Linker is a straight chain or branched, substituted or unsubstituted, saturated or unsaturated, aliphatic or aromatic group having between 1 and 50 carbon atoms and optionally substituted with one or more heteroatoms;

'Tag' is a detectable species;

'Spacer' is a straight chain or branched, substituted or unsubstituted, saturated or unsaturated, aliphatic or aromatic group having between 1 and 16 carbon atoms and optionally substituted with one or more heteroatoms;

'Blocking Moiety' is a straight chain or branched, substituted or unsubstituted, saturated or unsaturated, aliphatic or aromatic group having between 1 and 20 carbon atoms, and optionally substituted with one or more heteroatoms, and provided that the 'Blocking Moiety' includes an azide group, an isonitrile group, a 5- to 8-membered heterocycloalkyl group having at least one heteroatom selected from O, N, S, or Se, a moiety derived from a substituted or unsubstituted 1,4-epoxy-1,4-dihydronaphthalene, or a group having the structure:

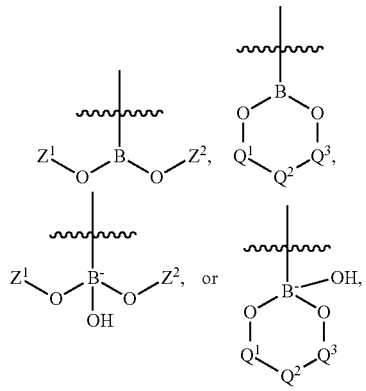

$Z^1$ and $Z^2$ are independently H, a $C_1$-$C_4$ alkyl group, a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2; and $R^e$ and $R^f$ are independently H, methyl, ethyl, isopropyl, or a substituted or unsubstituted 5- or 6-membered aryl group;

provided that when the 'Blocking Moiety' is —$N_3$, the 'Spacer' is not —$CH_2$—.

14. The nucleotide of claim 13, wherein the 'Linker' comprises a cleavable group.

15. The nucleotide of claim 14, wherein the cleavable group comprises a disulfide moiety, diazobenzene group, an ester group, a 1,2-diol group, a boronic acid group, or an p-alkoxybenzyl group.

16. The nucleotide of claim 13, wherein the 'Tag' comprises a PEG-based polymer, an oligonucleotide, a polypeptide, or a fluorescent moiety.

17. The nucleotide of claim 13, wherein the 'Blocking Moiety' comprises —B(O$Z^1$)(O$Z^2$).

18. The nucleotide of claim 17, wherein $Z^1$ and $Z^2$ are independently selected from the group consisting of H, methyl, and ethyl.

19. The nucleotide of claim 13, wherein the 'Blocking Moiety' comprises —B(O$Z^1$)(OH).

20. The nucleotide of claim 19, wherein $Z^1$ is selected from the group consisting of H, methyl, and ethyl.

21. The nucleotide of claim 13, wherein the 'Blocking Moiety' comprises —B(OH)$_2$ or —B(OH)$_3^-$.

22. A nucleotide or a salt thereof of Formula (IIIA):

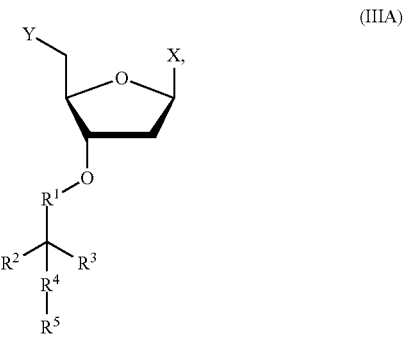

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are independently H, a saturated or unsaturated $C_1$-$C_6$ alkyl group, a $C_5$-$C_6$ aryl or heteroaryl group, a halogen, —[C($R^a$)($R^b$))$_p$—O]$_q$ ($R^a$), —C(O)—O$R^a$, —C(O)—N($R^a$)($R^b$), —(C($R^a$)($R^b$))$_n$—N$^+$C$^-$, —CN, or —NO$_2$;

$R^4$ is a substituted or unsubstituted 5- to 7-membered aryl group, —CH═CH—, a substituted or unsubstituted 5- or 6-membered heterocycloalkyl group, or —O—C(O)-aryl-;

$R^5$ is —(C($R^a$)($R^b$))$_n$—N$_3$, —(C($R^a$)($R^b$))$_n$—N$^+$C$^-$, —(C($R^a$)($R^b$))$_n$—CN, a 5- to 8-membered cycloalkyl group comprising two sulfur atoms positioned 1, 3 relative to each other, or a group having the structure:

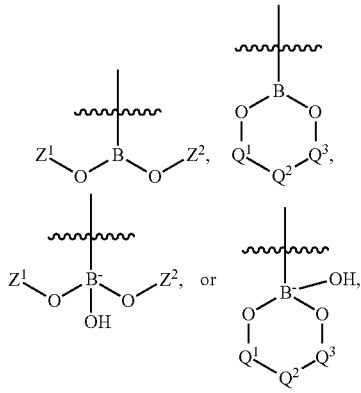

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C($R^e$)($R^f$)—, or —C(O)—;

$Q^2$ is a bond, o-phenylene, or —[C($R^e$)($R^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide.

23. A nucleotide or a salt thereof of Formula (IIIA):

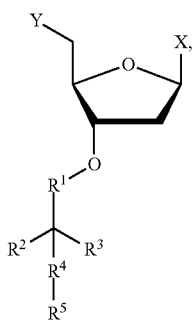

(IIIA)

wherein

X is a nucleobase or a tagged nucleobase;

Y is —O—P(O)(OH)—[O—P(O)(OH)]$_z$—OH or —O—P(O)(OH)—[O—P(O)(OH)]$_z$—O-oligonucleotide, where z is 0 or an integer ranging from 1 to 5;

$R^1$ is a bond, —CH$_2$—, —C(O)—O—, —C(O)—NR$^a$—, or —C(O)—R$^x$—;

$R^2$ and $R^3$ are each independently H, a saturated or unsaturated $C_1$-$C_6$ alkyl group, a $C_5$-$C_6$ aryl or heteroaryl group, a halogen, —[(C(R$^a$)(R$^b$))$_p$—O]$_q$ (R$^a$), —C(O)—OR$^a$, —C(O)—N(R$^a$)(R$^b$), —(C(R$^a$)(R$^b$))$_n$—N$^+$C$^-$, —CN, or —NO$_2$;

$R^4$ is a bond, a substituted or unsubstituted 5- to 7-membered aryl group, —CH=CH—, a substituted or unsubstituted 5- or 6-membered heterocycloalkyl group, or —O—C(O)-aryl-;

$R^5$ is

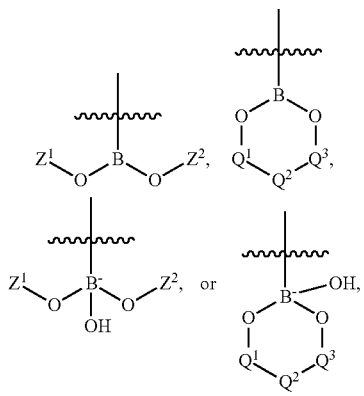

$Z^1$ and $Z^2$ are independently H, a $C_1$-$C_4$ alkyl group, or a 5- to 6-membered aryl group optionally substituted with one or more hydroxyl groups;

$Q^1$ and $Q^3$ are each independently a bond, —C(R$^e$)(R$^f$)—, or —C(O)—;

$Q^2$ is a bond, o-phenylene, or —[C(R$^e$)(R$^f$)]$_w$—, where w is 1 or 2;

$R^a$ and $R^b$ are each independently H or a saturated $C_1$-$C_6$ alkyl group;

$R^e$ and $R^f$ are independently H, methyl, ethyl, isopropyl, or a substituted or unsubstituted 5- or 6-membered aryl group;

$R^x$ is a substituted or unsubstituted 5- or 6-membered aromatic group or heteroaromatic group;

n is 0 or an integer ranging from 1 to 3; and p and q are each independently zero or an integer ranging from 1 to 3;

provided that when $R^1$ and $R^4$ are both bonds and when $R^2$ and $R^3$ are both H, then $R^5$ is not an azide.

* * * * *